United States Patent
Ishii et al.

(10) Patent No.: US 12,319,727 B2
(45) Date of Patent: **\*Jun. 3, 2025**

(54) EXOSOME-TARGETED DNA VACCINE

(71) Applicant: EXORPHIA, INC., Tokyo (JP)

(72) Inventors: Ken Ishii, Tokyo (JP); Kouji Kobiyama, Ibaraki (JP); Tomohiro Kanuma, Ibaraki (JP)

(73) Assignee: EXORPHIA, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/448,713

(22) Filed: Aug. 11, 2023

(65) Prior Publication Data

US 2024/0018214 A1    Jan. 18, 2024

Related U.S. Application Data

(60) Continuation of application No. 17/587,925, filed on Jan. 28, 2022, now Pat. No. 12,209,115, which is a division of application No. 16/091,073, filed as application No. PCT/JP2016/001900 on Apr. 4, 2016.

(51) Int. Cl.

| | |
|---|---|
| *C07K 14/705* | (2006.01) |
| *A61K 31/713* | (2006.01) |
| *A61K 39/00* | (2006.01) |
| *A61K 48/00* | (2006.01) |
| *A61P 35/00* | (2006.01) |
| *C07K 14/47* | (2006.01) |
| *C07K 14/77* | (2006.01) |
| *C12N 15/09* | (2006.01) |

(52) U.S. Cl.
CPC ...... *C07K 14/70596* (2013.01); *A61K 31/713* (2013.01); *A61K 39/00* (2013.01); *A61K 39/0011* (2013.01); *A61K 48/00* (2013.01); *A61P 35/00* (2018.01); *C07K 14/47* (2013.01); *C07K 14/77* (2013.01); *C12N 15/09* (2013.01); *A61K 2039/53* (2013.01); *A61K 2039/572* (2013.01); *A61K 2039/575* (2013.01); *A61K 2039/6031* (2013.01); *C07K 2319/00* (2013.01); *C07K 2319/43* (2013.01)

(58) Field of Classification Search
CPC .. C07K 14/70596; C07K 14/47; C07K 14/77; C07K 2319/00; C07K 2319/43; A61K 31/713; A61K 39/00; A61K 39/0011; A61K 48/00; A61K 2039/53; A61K 2039/572; A61K 2039/575; A61K 2039/6031; A61P 35/00; C12N 15/09

See application file for complete search history.

(56) References Cited

U.S. PATENT DOCUMENTS

| 10,233,445 B2 * | 3/2019 | Seow | C07K 14/705 |
| 2017/0274062 A1 * | 9/2017 | Romero Ramos | A61K 39/02 |

FOREIGN PATENT DOCUMENTS

| AU | 2000010514 A1 | 7/2000 |
| JP | 2002-529074 A | 9/2002 |
| JP | 2015-500825 A | 1/2015 |
| WO | 00/28001 A1 | 5/2000 |
| WO | 2013/084000 A2 | 6/2013 |

OTHER PUBLICATIONS

Maecker (BMC immunology 4.1 (2003): 1-14) (Year: 2003).*
Kalluri et al., "The biology, function, and biomedical applications of exosomes," *Science* 367: eaau6977, Feb. 2020.
Hartman et al., "Increasing vaccine potency through exosome antigen targeting," *Vaccine* 29:9361-9367, 2011.
Kanuma et al., "Antigen specific CD8 T cell response by exosome targeting DNA vaccine," *The Japanese Society for Vaccinology Gakujutsu Shukai Program Shorokushu* 19:116, 2015, 4 pages.
Kanuma et al., "Exosome targeting DNA vaccination enhances antigen-specific CD8 T cell responses," Abstract 3D-W37-8-0/P, Oct. 30, 2015, 1 page.
Zeelenberg et al., "Targeting Tumor Antigens to Secreted Membrane Vesicles In vivo Induces Efficient Antitumor Immune Responses," *Cancer Res* 68(4):1228-1235, 2008.

\* cited by examiner

*Primary Examiner* — Celine X Qian
*Assistant Examiner* — Kyle T Rega
(74) *Attorney, Agent, or Firm* — Seed IP Law Group LLP

(57) ABSTRACT

In order to further increase antigenicity to provide a DNA vaccine which is clinically usable in humans, the inventors of the present invention focused on exosomes, which are garnering attention as tools for DDS, and discovered that an exosome expressing a fusion antigen of an exosome (extracellular microparticle)-constituent protein and a vaccine antigen has excellent cytotoxic T-cell inducibility. Consequently, the present invention provides a nucleic acid constituent including a nucleic acid sequence coding for an exosome marker protein and a nucleic acid sequence coding for a vaccine antigen.

20 Claims, 25 Drawing Sheets
Specification includes a Sequence Listing.

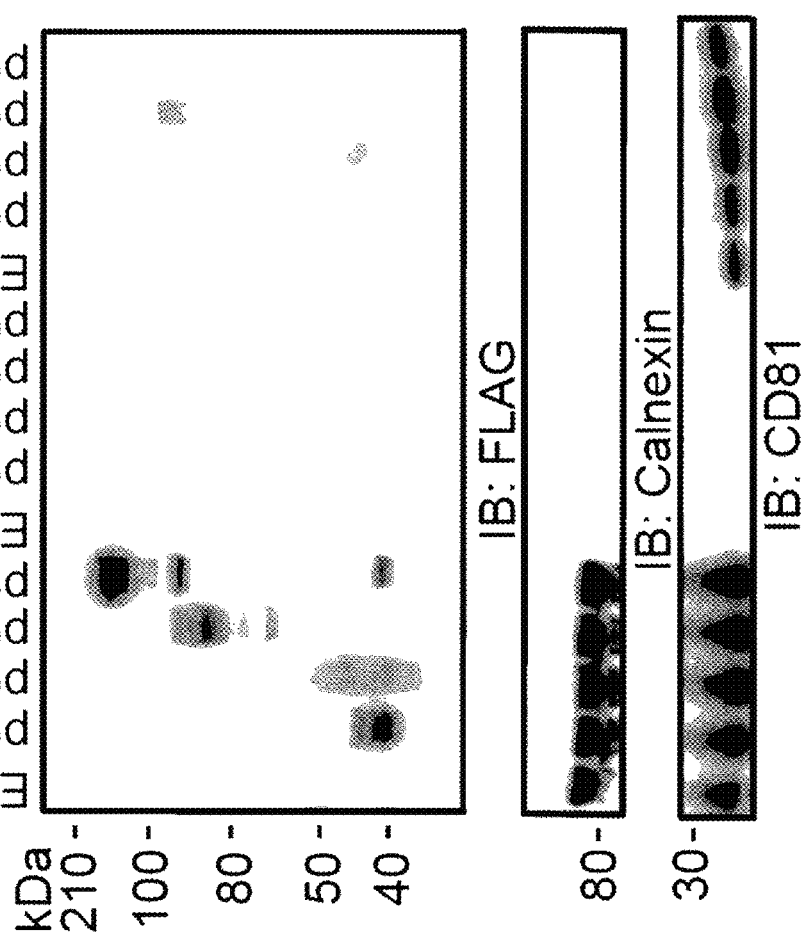

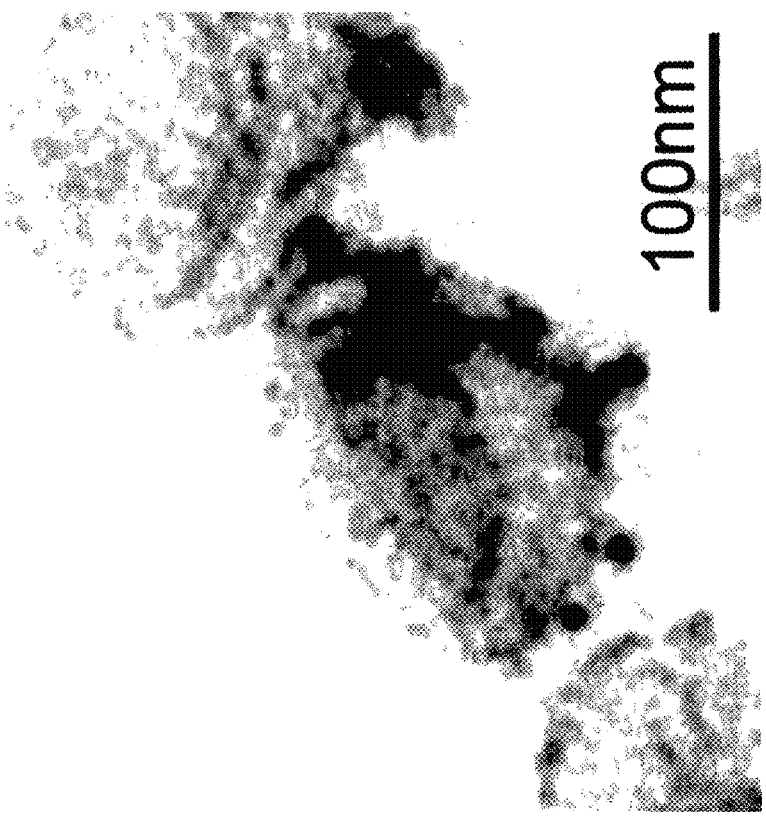
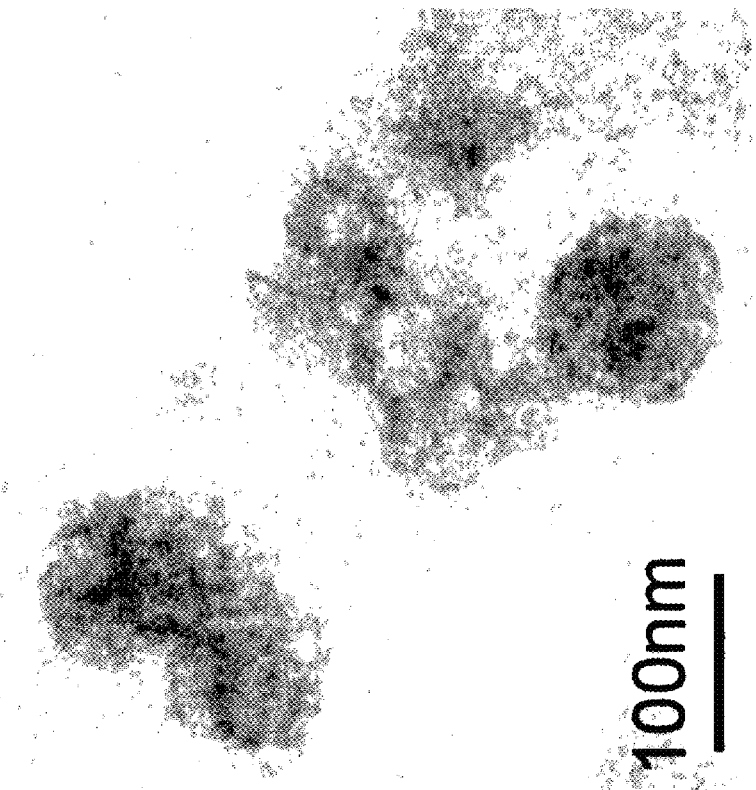
Fig. 1C

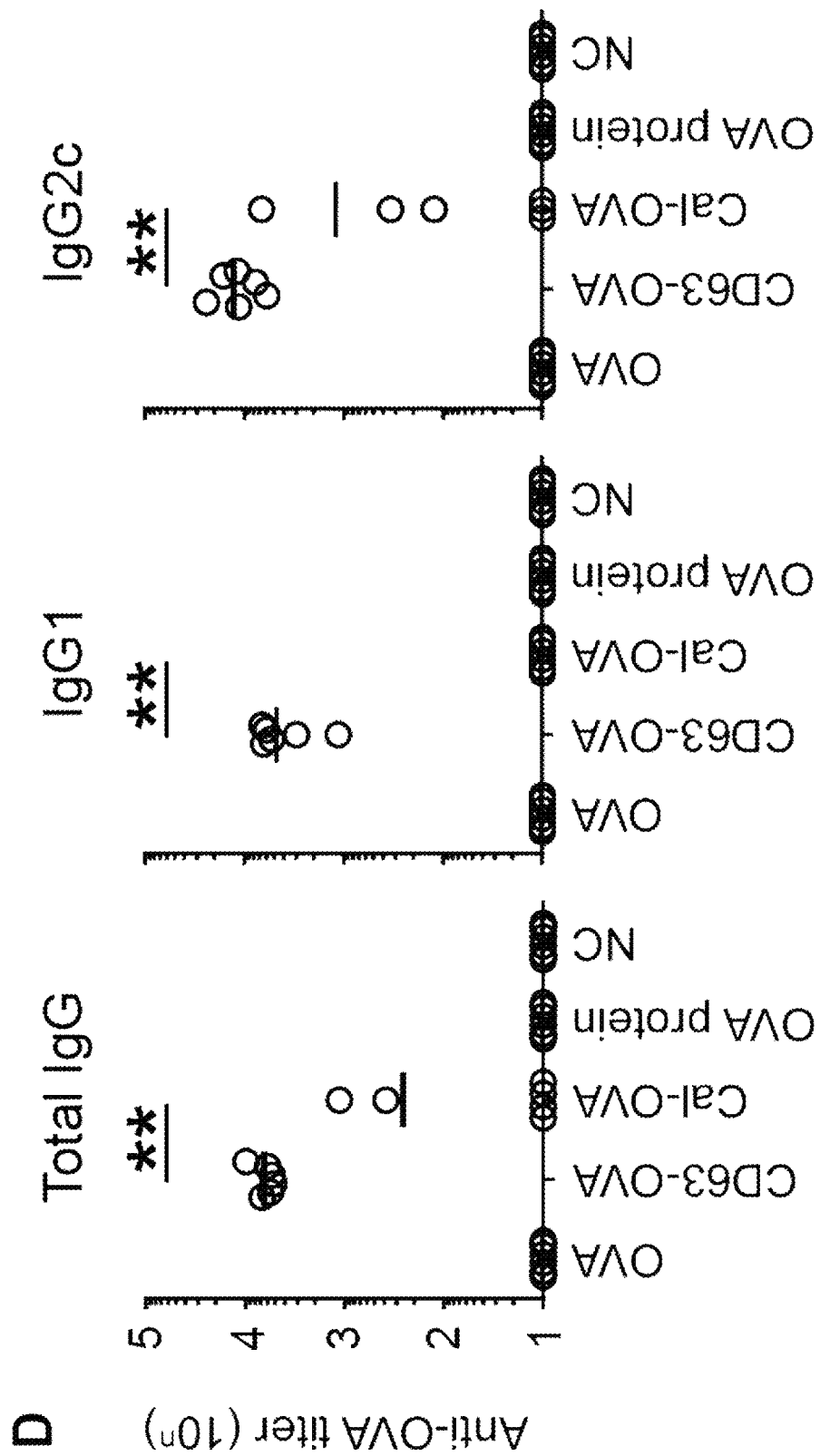

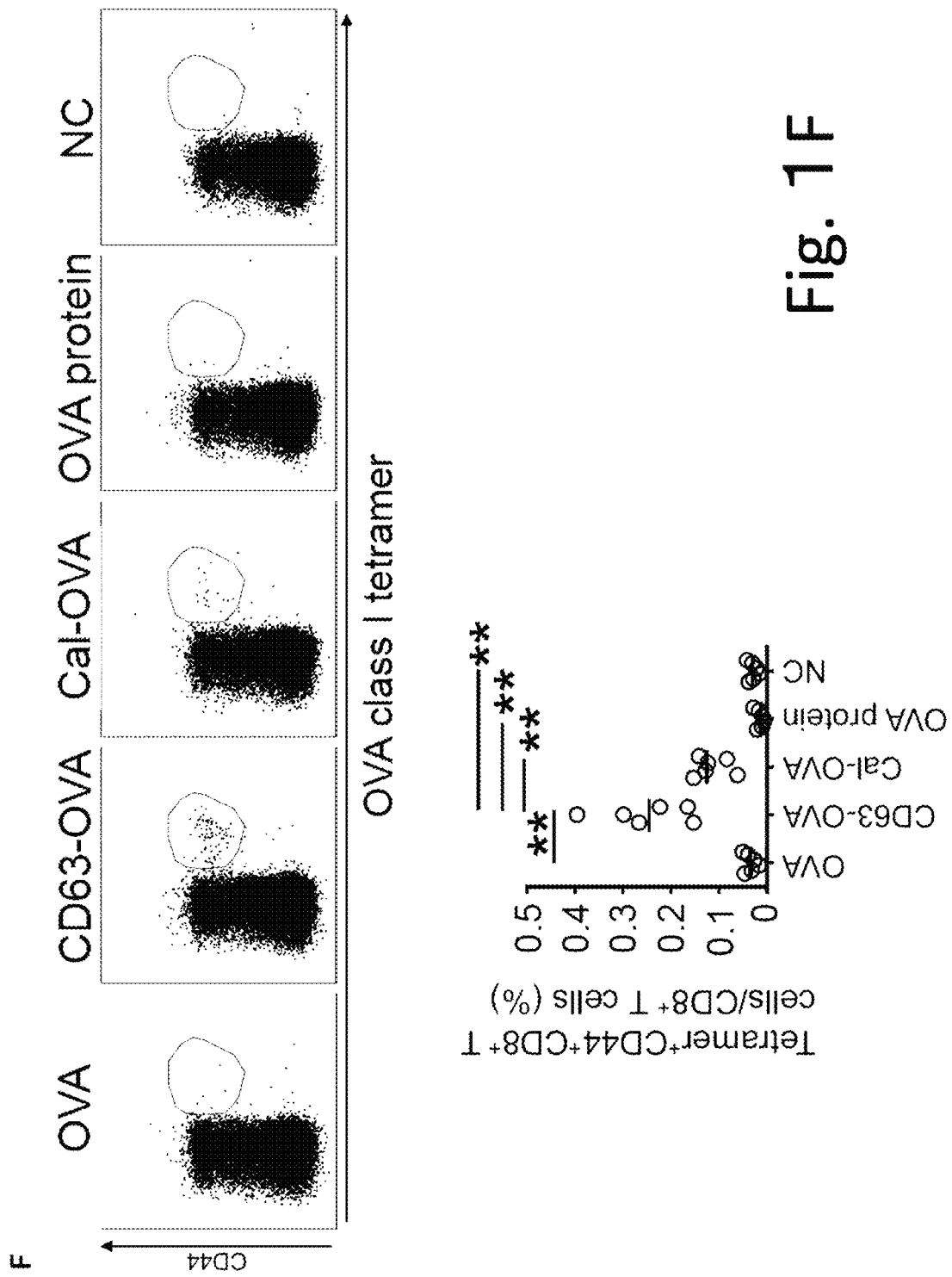

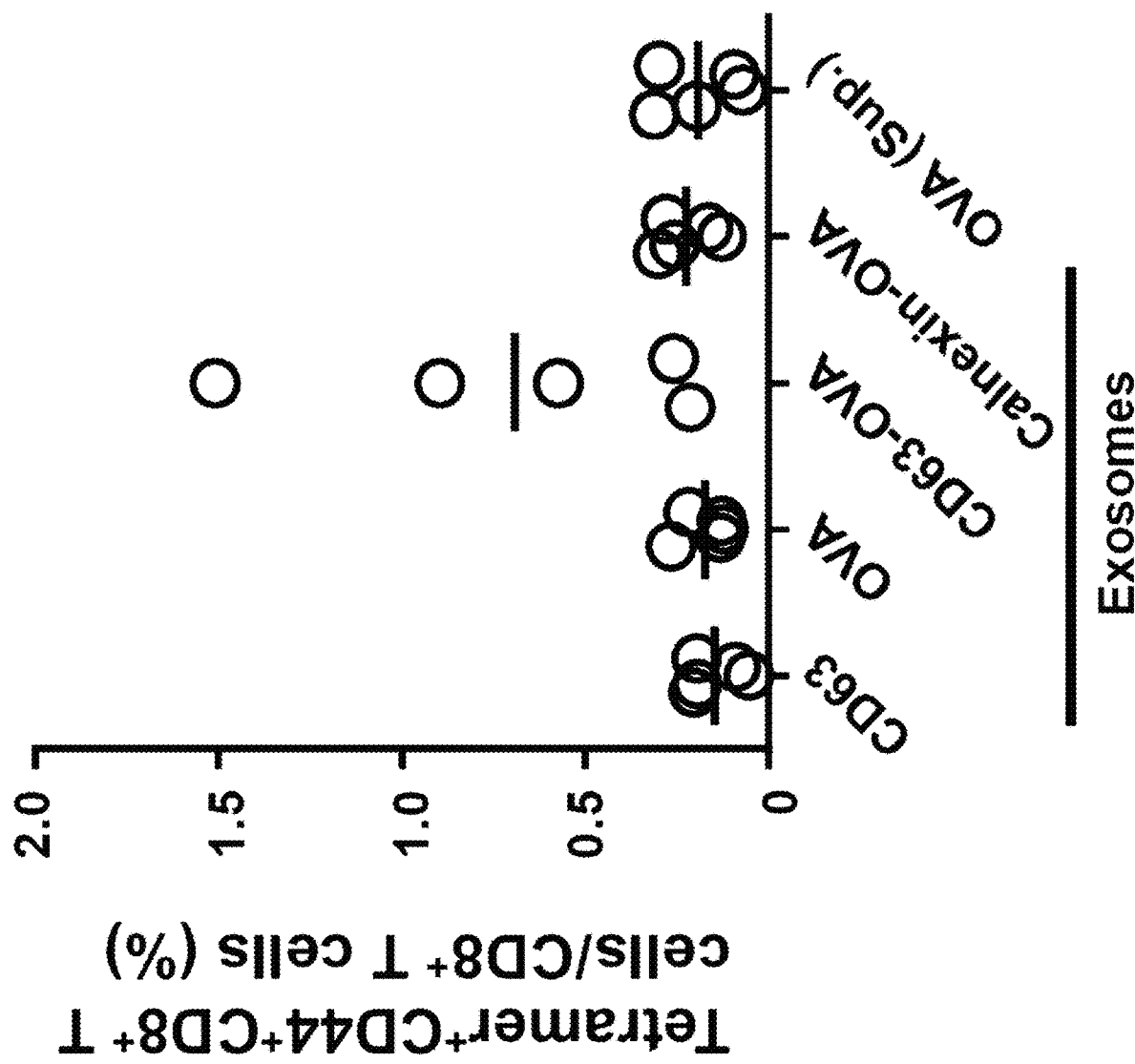

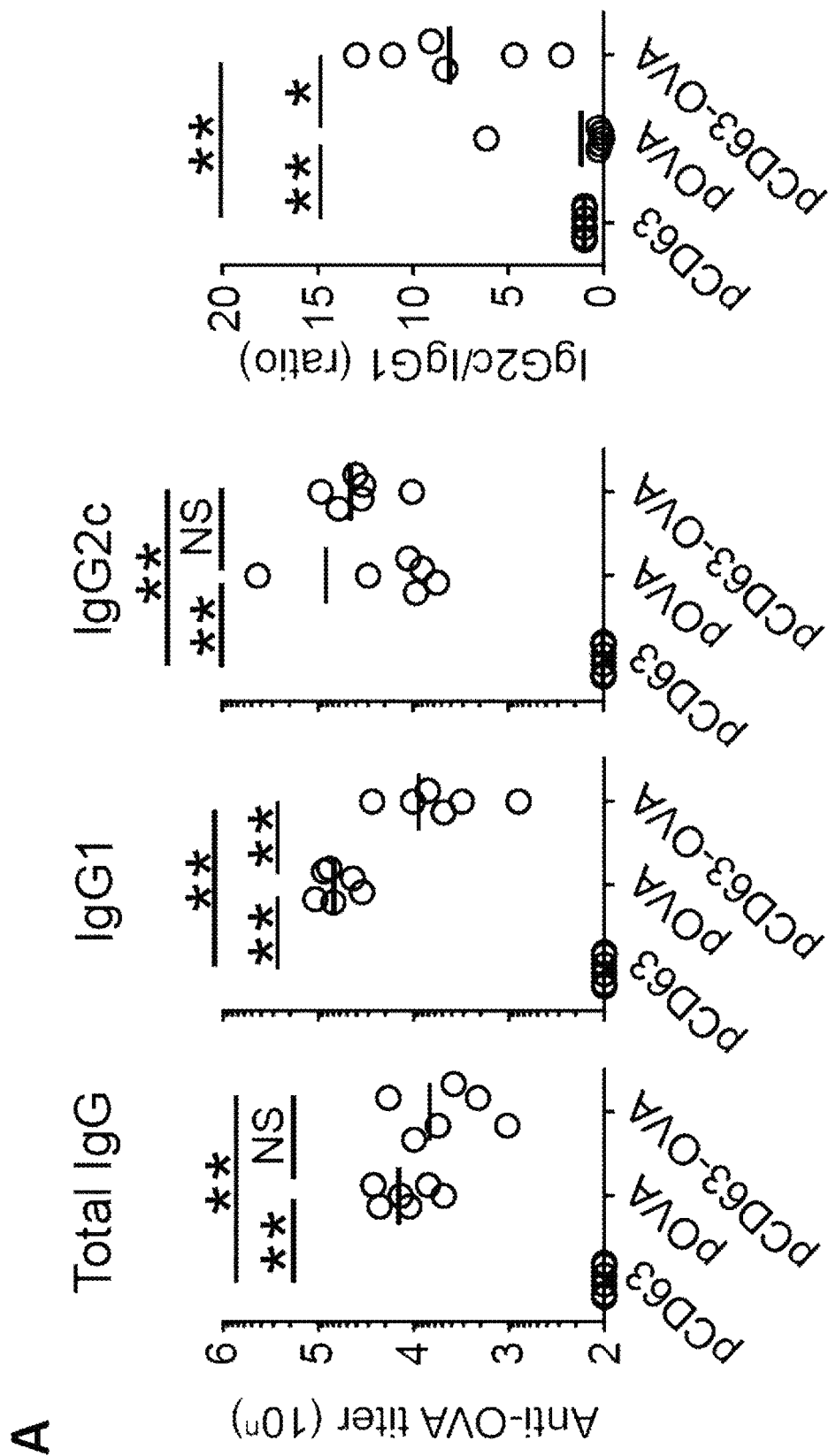

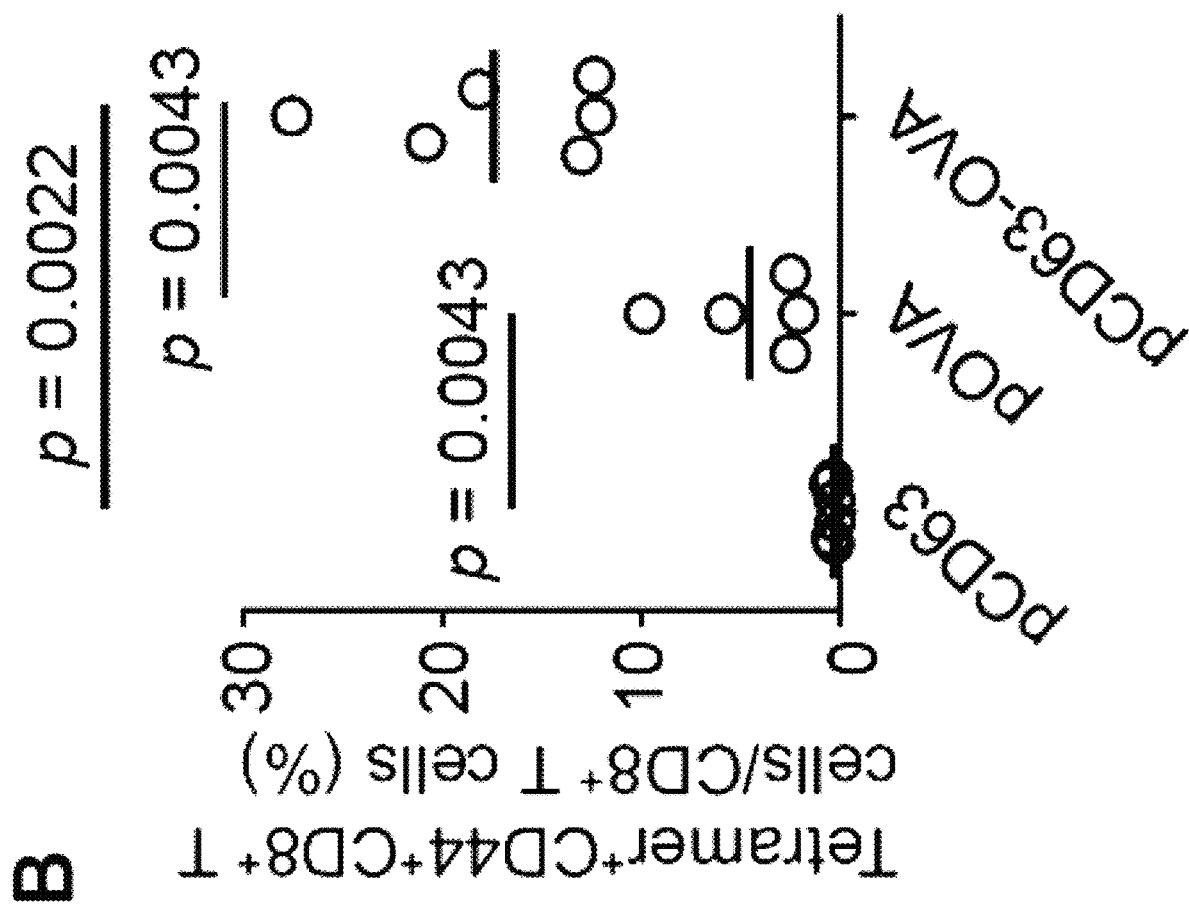

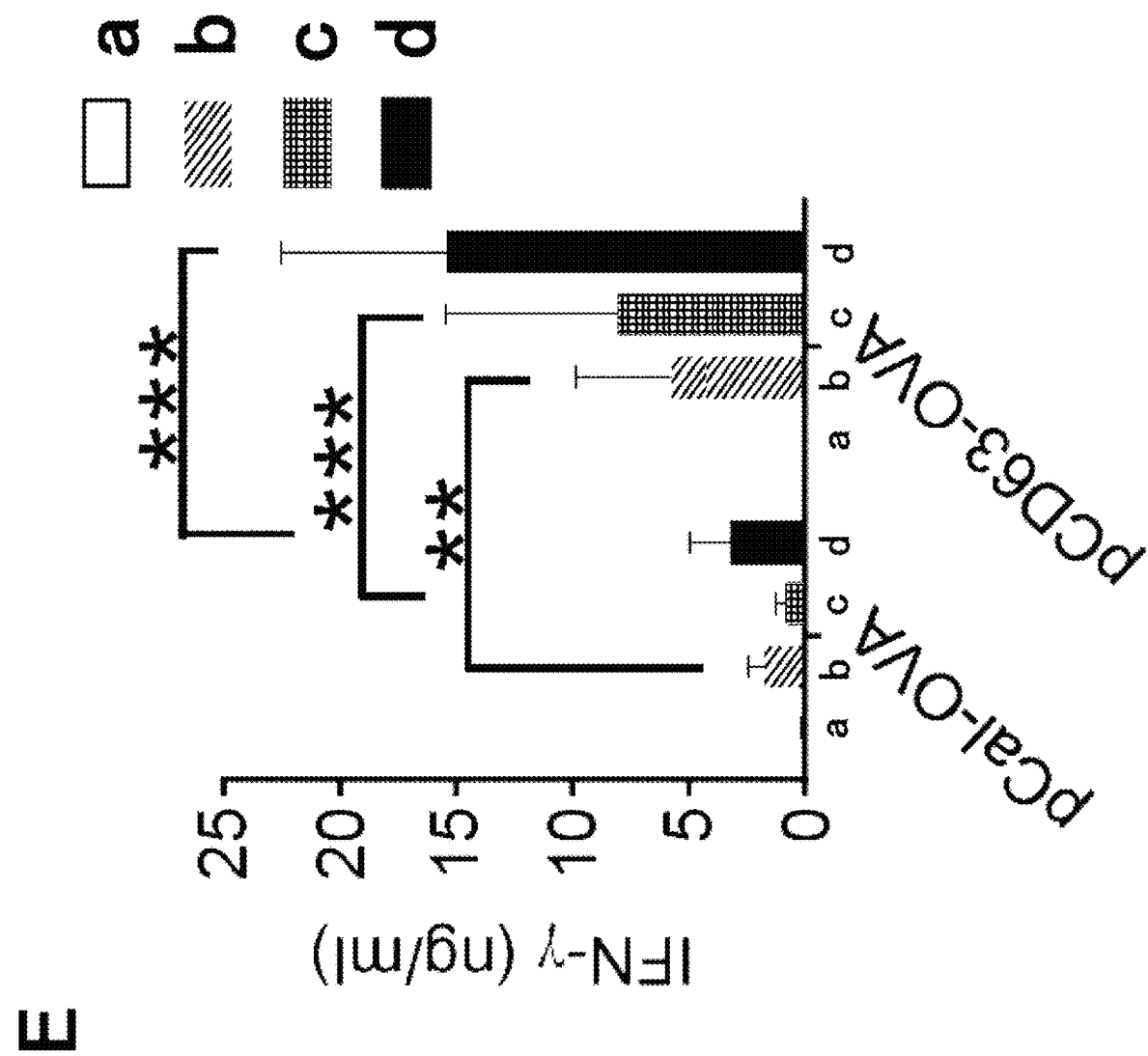

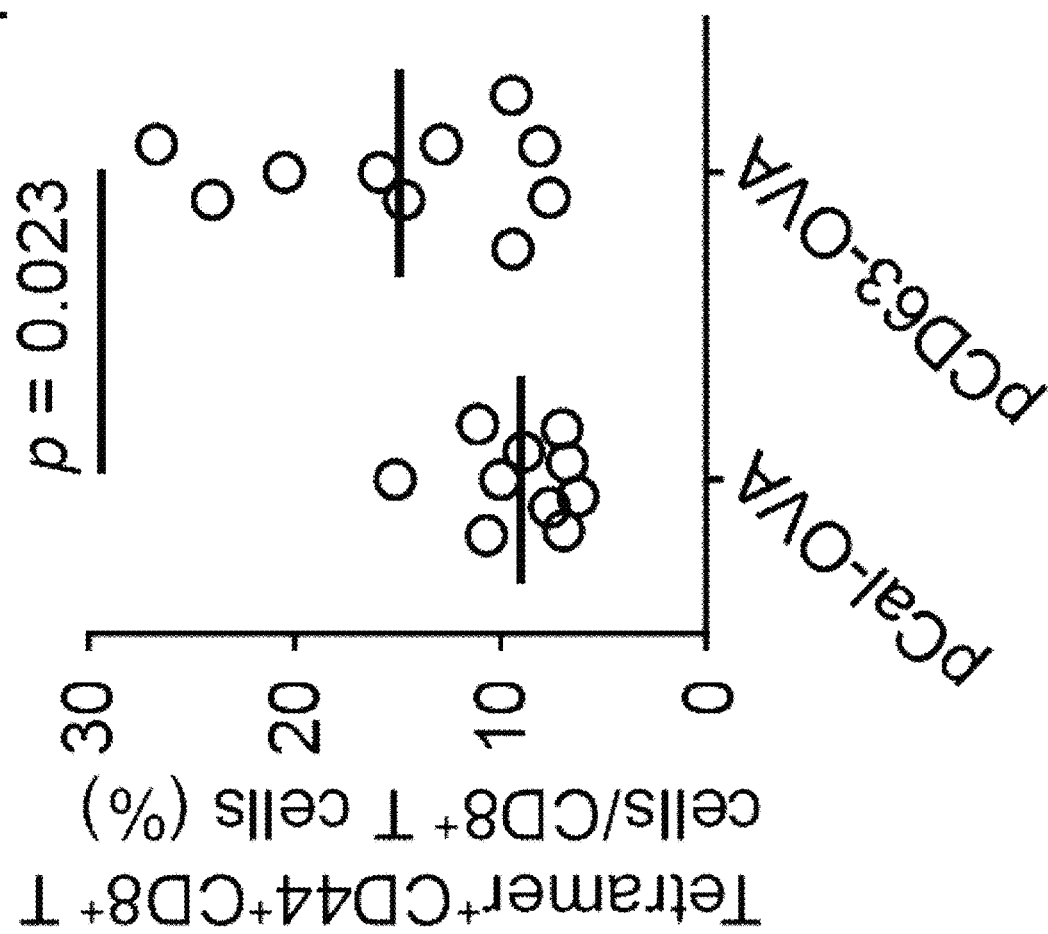

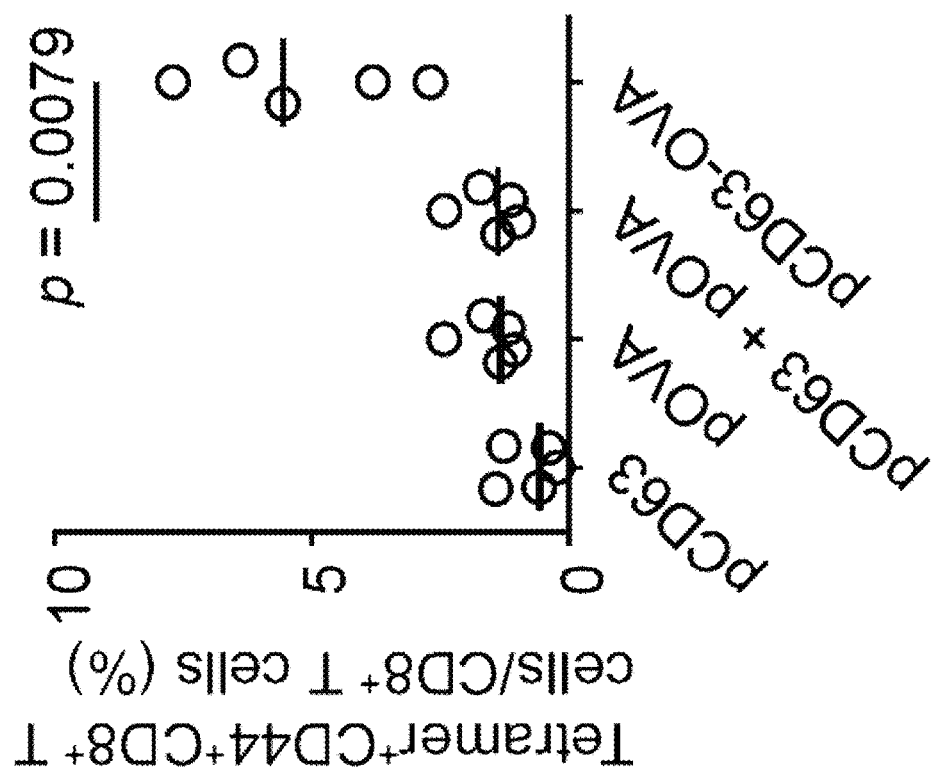

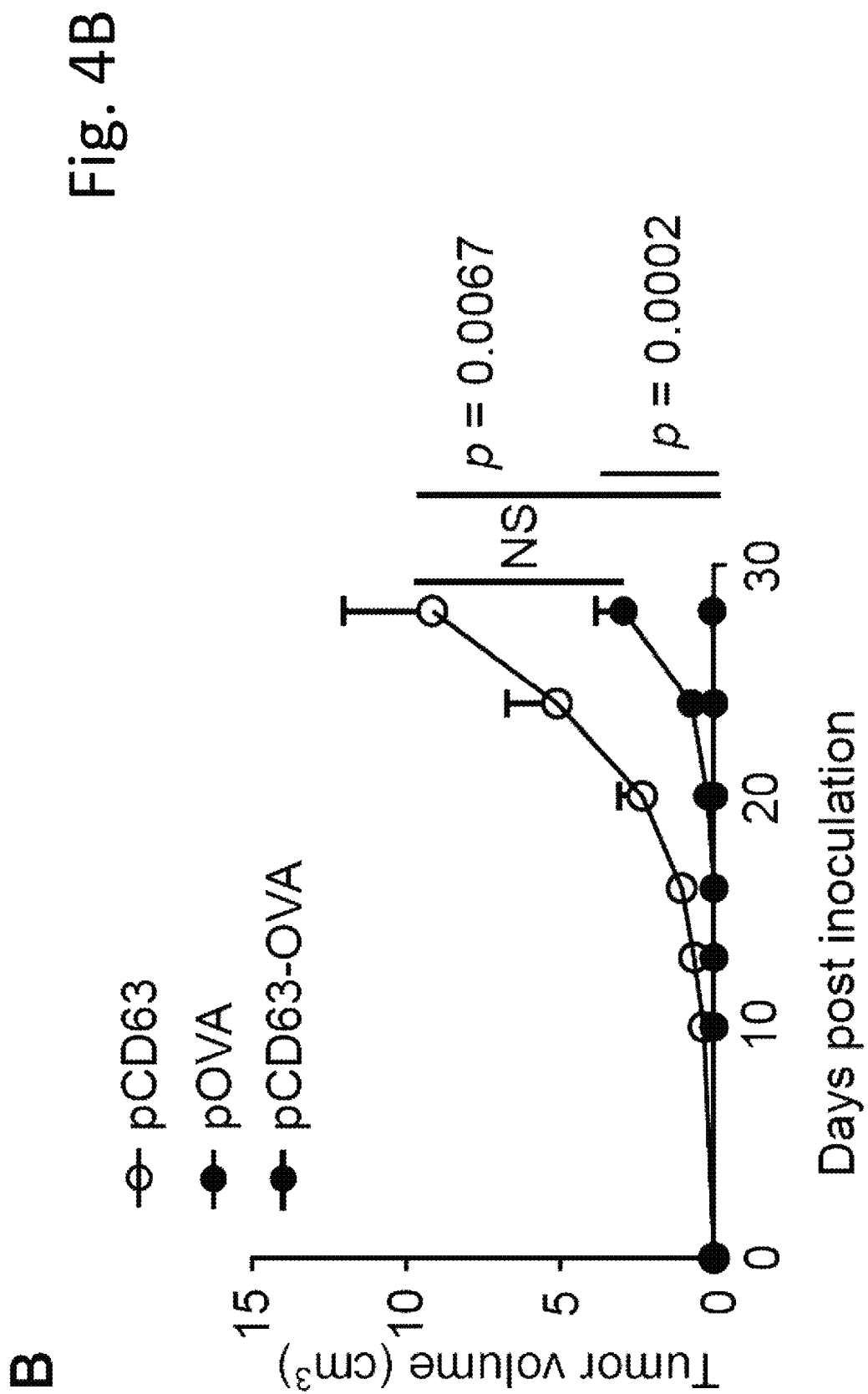

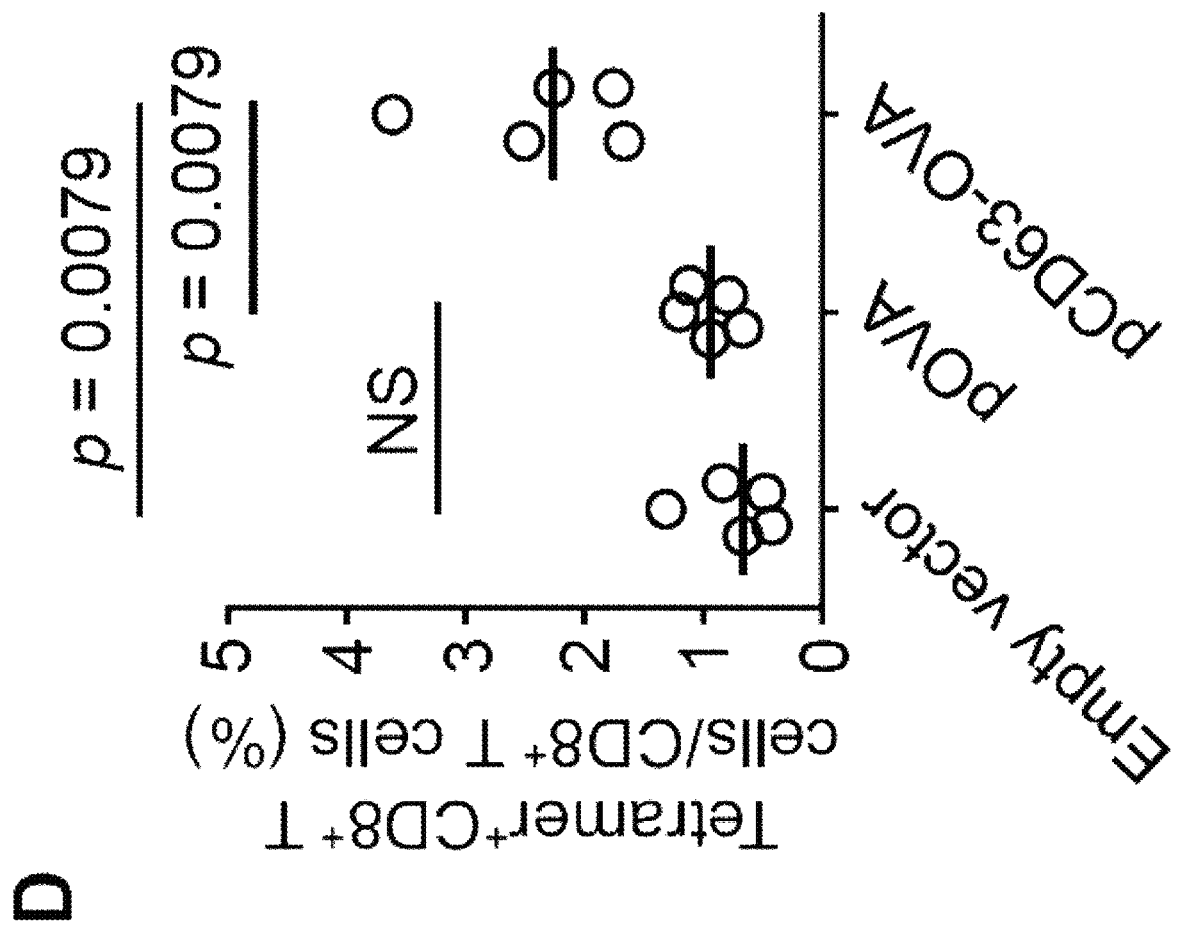

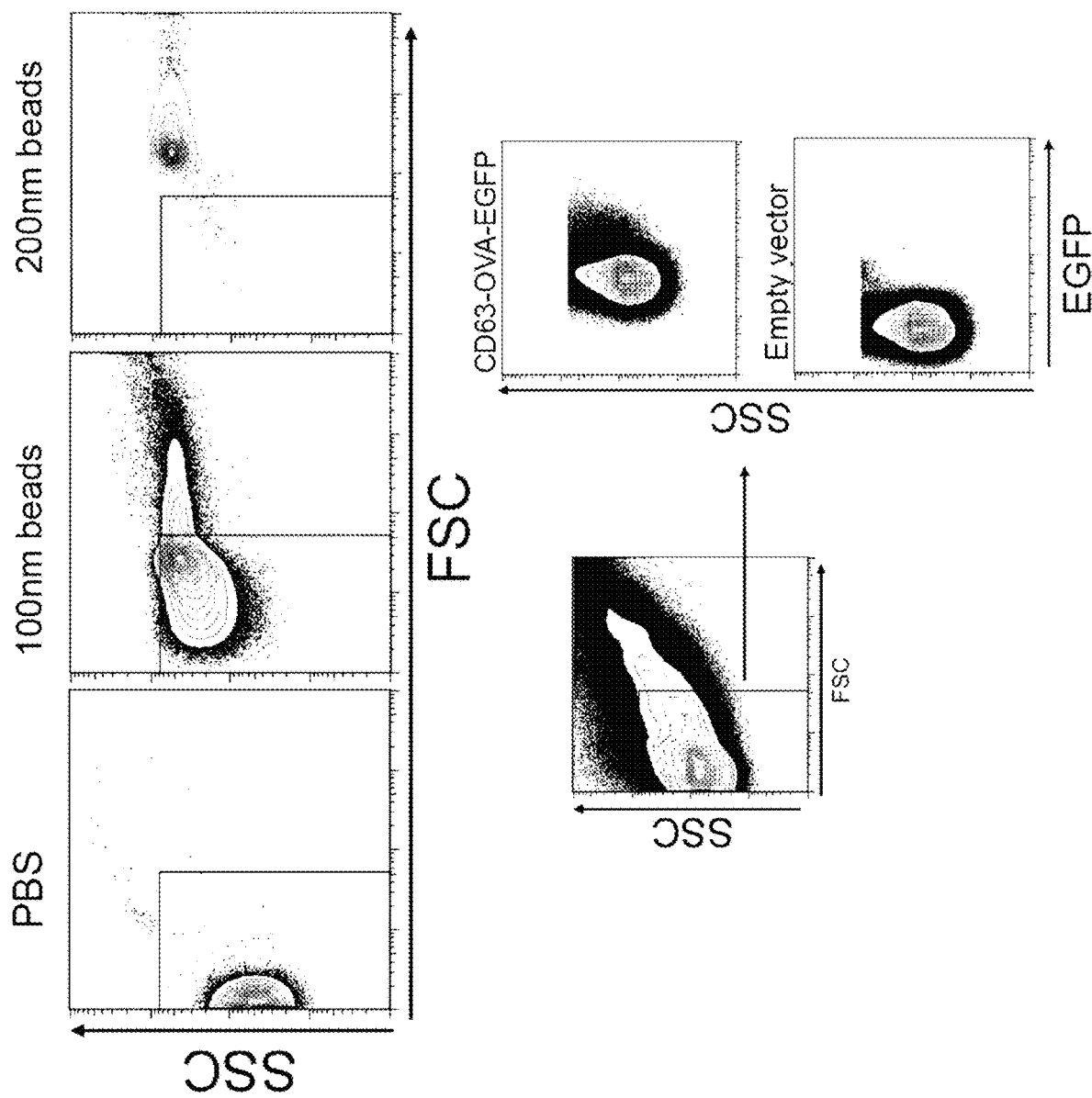

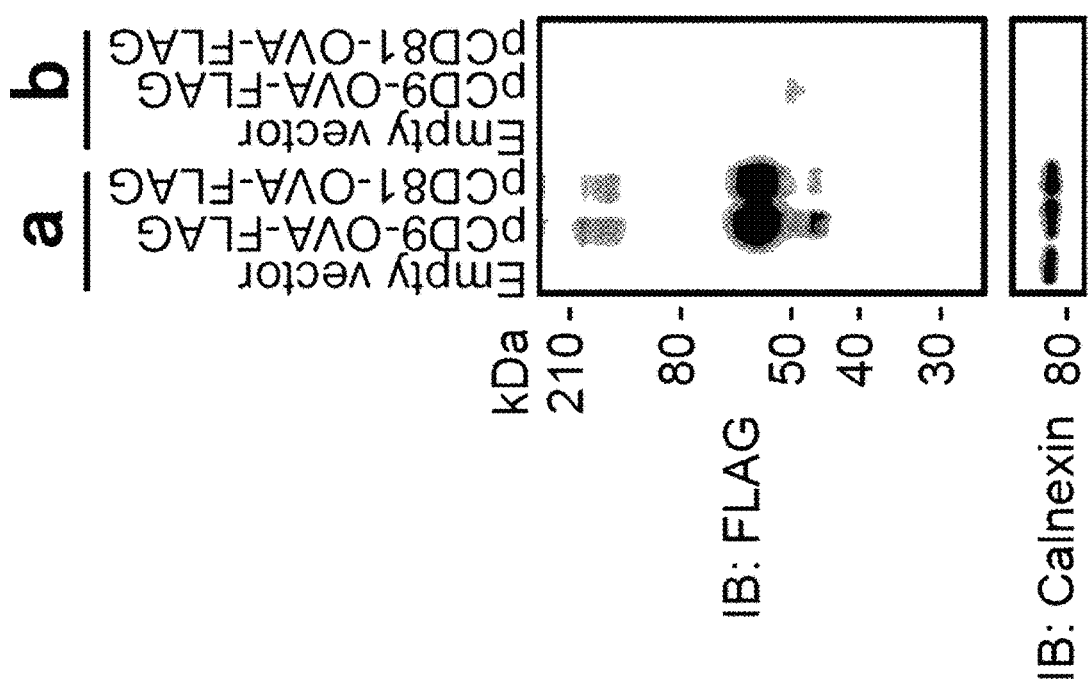

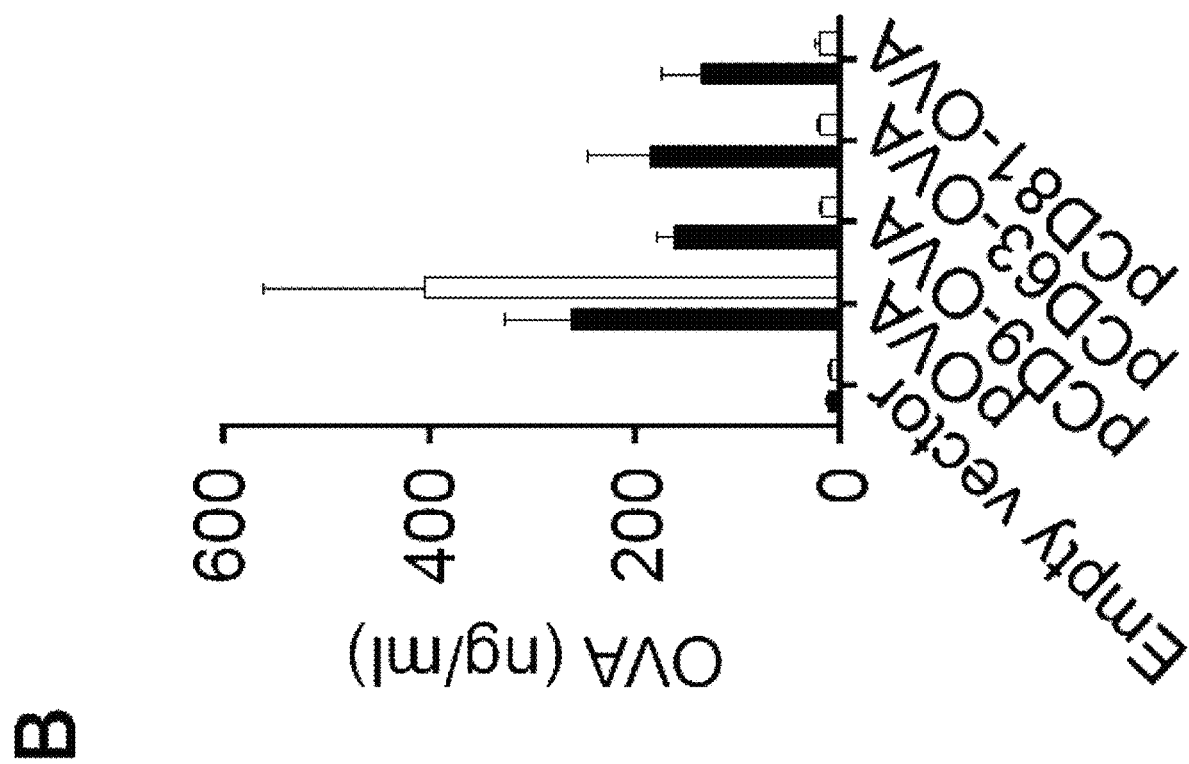

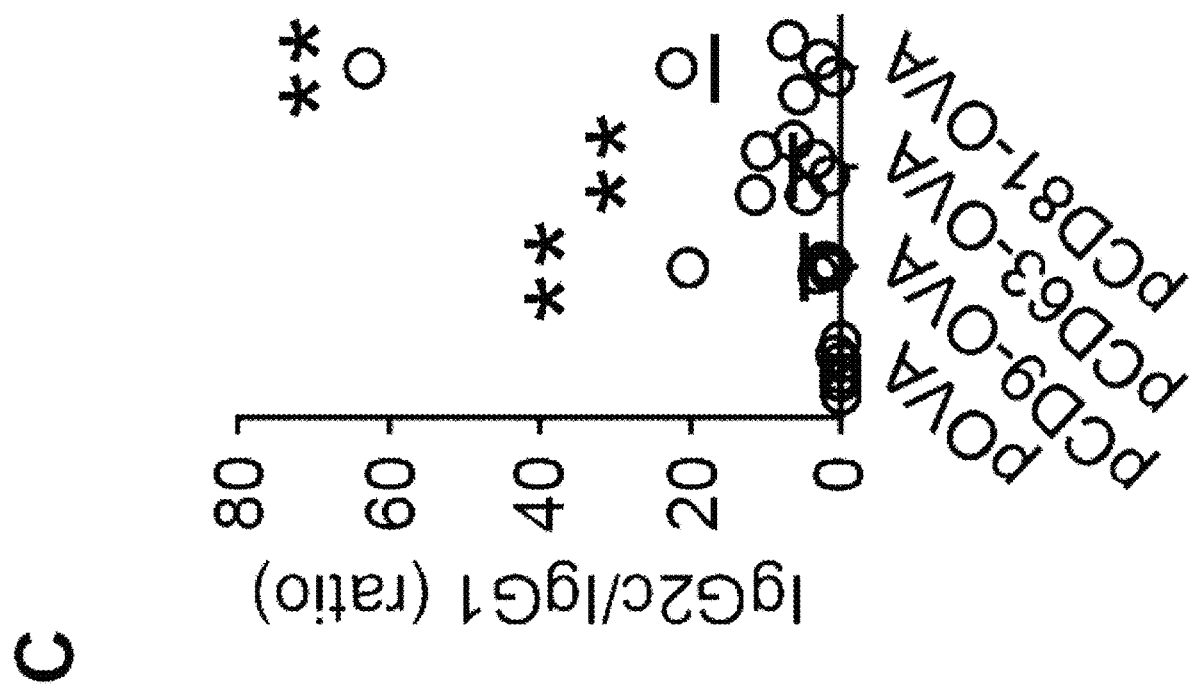

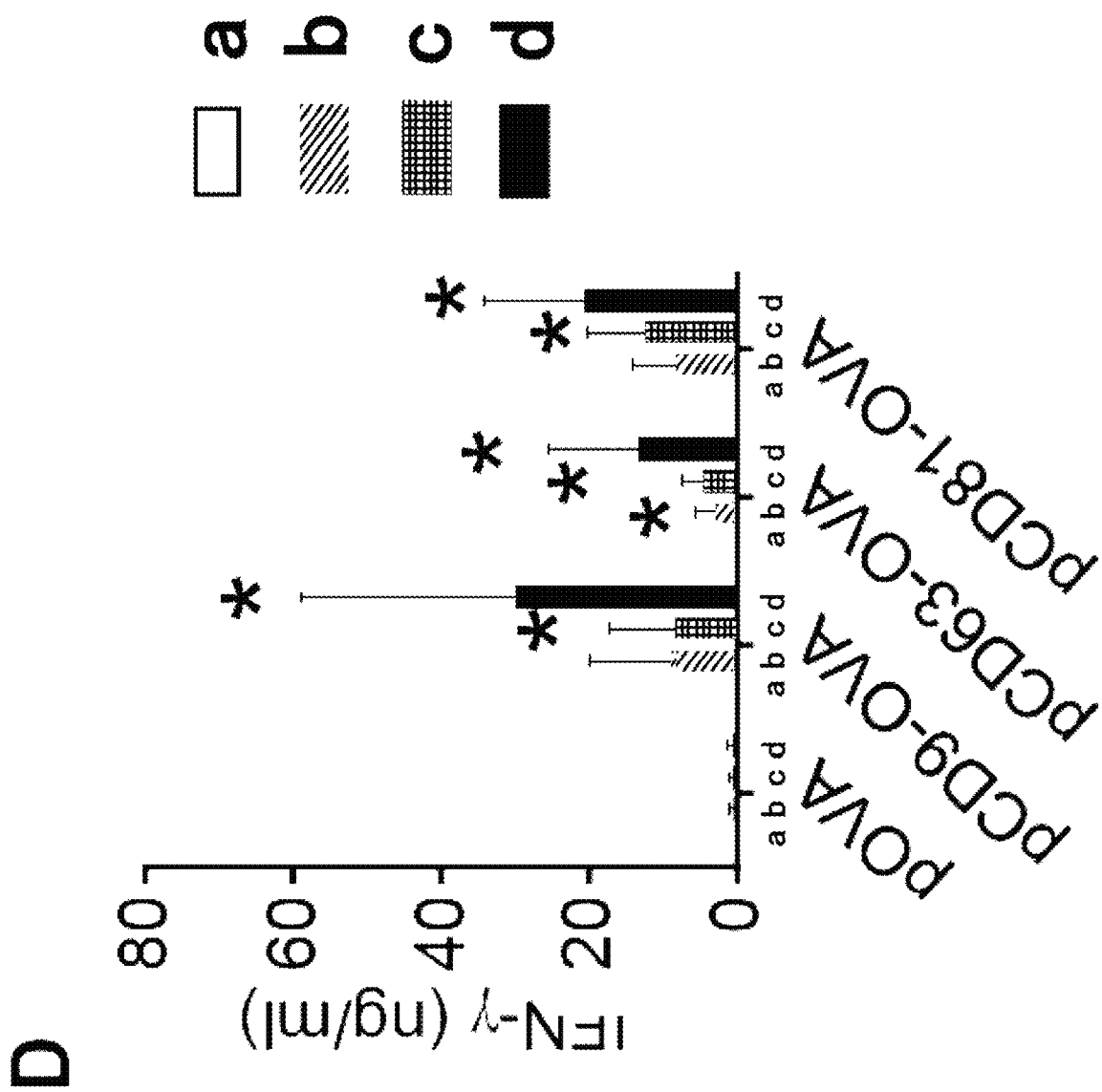

```
                              SEQUENCE LISTING

Sequence total quantity: 16
SEQ ID NO: 1              moltype = DNA  length = 1025
FEATURE                   Location/Qualifiers
source                    1..1025
                          mol_type = other DNA
                          organism = Homo sapiens
CDS                       186..896
SEQUENCE: 1
cagctgttac cgcgtcacat gaggaggcc ggcggccact cggcggggga ggggaccgtg   60
gctggagccc ggggcgggc cgcgcggcag gcggggcggg agccggggg cgcagctaga  120
gagccccgga gccgcggcgg gagaggaacg cgcagccagc cttgggaagc ccaggcccgg  180
cagccatggc ggtggaagga ggaatgaaat gtgtgaagtt cttgctctac gtcctcctgc  240
tggccttttg cgcctgtgca gtgggactga ttgccgtggg tgtcgggcaa cagcttgtcc  300
tgagtcagac cataatccag ggggctaccc ctggctctct gttgccagtg gtcatcatcg  360
cagtgggtgt cttcctcttc ctggtggctt ttgtgggctg ctgcggggcc tgcaaggaga  420
actattgtct tatgatcacg tttgccatct ttctgtctct tatcatgttg gtggaggtgg  480
ccgcagccat tgctggctat gtgtttagag ataaggtgat gtcagagttt aataacaact  540
tccggcagca gatggagaat tacccgaaaa acaaccacac tgcttcgatc ctggacagga  600
tgcaggcaga ttttaagtgc tgtgggctg ctaactacac agattgggag aaaatcccctt  660
ccatgtcgaa gaaccgagtc cccgactcct gctgcattaa tgttactgtg ggctgtggga  720
ttaatttcaa cgagaaggcg atccataagg agggctgtgt ggagaagatt ggggctggcc  780
tgaggaaaaa tgtgctggtg gtagctgcag cagcccttgg aattgctttt gttttgggaa  840
ttgtctttgc ctgctgcctc gtgaagagta tcagaagtgg ctacgaggtg atgtaggggt  900
ctggtctcct cagcctcctc atctggggga gtggaatagt atcctccagg tttttcaatt  960
aaacggatta tttttcaga ccgaaagag atggtctgag tttgtcttag aaaaaaaaaa 1020
aaaaa                                                              1025

SEQ ID NO: 2              moltype = AA  length = 236
FEATURE                   Location/Qualifiers
source                    1..236
                          mol_type = protein
                          organism = Homo sapiens
SEQUENCE: 2
MAVEGGMKCV KFLLYVLLLA FCACAVGLIA VGVGAQLVLS QTIIQGATPG SLLPVVIIAV   60
GVFLFLVAFV GCCGACKENY CLMITFAIFL SLIMLVEVAA AIAGYVFRDK VMSEFNNNFR  120
QQMENYPKNN HTASILDRMQ ADFKCCGAAN YTDWEKIPSM SKNRVPDSCC INVTVGCGIN  180
FNEKAIHKEG CVEKIGGWLR KNVLVVAAAA LGIAFVLGIV FACCLVKSIR SGYEVM      236
```

-continued

```
SEQ ID NO: 3            moltype = DNA   length = 959
FEATURE                 Location/Qualifiers
source                  1..959
                        mol_type = other DNA
                        organism = Mus musculus
CDS                     146..862
SEQUENCE: 3
agtaagcaac tcaaggcaga aggagctgcg gagaaaagga caaagttcag gttaggagtg   60
taaggccggt cggtcctatc tgagcttttt acaacagttc cttctgtgaa ccaccagcag  120
cacacgggag aaaggcccaa cagccatggc ggtggaagga ggaatgaagt gtgtcaagtt  180
tttgctctac gttctcctgc tggccttctg cgcctgtgca gtgggattga tcgccattgg  240
tgtagcggtt caggttgtct tgaagcaggc cattacccat gagactactg ctggctcgct  300
gttgcctgtg gtcatcattg cagtgggtgc cttcctcttc ctggtggcct ttgtgggctg  360
ctgtgggggc tgcaaggaga actactgtct catgattaca tttgccatct tcctgtcctt  420
tatcatgctt gtggaggtgg ctgtggccat tgctggctat gtgtttagag accaggtgaa  480
gtcagagttt aataaaagct ccagcagca gatgcagaat acctaaaag acaacaaaac  540
agccactatt ttggacaaat gcagaaaga aaataactgc tgtggagctt ctaactacac  600
agactgggaa aacatccccg gcatggccaa ggacagagtc cccgattctt gctgcatcaa  660
cataactgtg ggctgtggga atgatttcaa ggaatccact atccatacc agggctgcgt  720
ggagactata gcaatatggc taaggaagaa catactgctg gtggctgcag cggccctggg  780
cattgctttt gtggaggtct tgggaattat cttctcctgc tgtctggtga agagtattcg  840
aagtggctat gaagtaatgt aggggtgggg ggcgtttggt cttttcatgg agtggattct  900
ccaggttttt caattaaacg gattattttt tcagacctaa aaaaaaaaa aaaaaaaa    959

SEQ ID NO: 4            moltype = AA   length = 238
FEATURE                 Location/Qualifiers
source                  1..238
                        mol_type = protein
                        organism = Mus musculus
SEQUENCE: 4
MAVEGGMKCV KFLLYVLLLA FCACAVGLIA IGVAVQVVLK QAITHETTAG SLLPVVIIAV   60
GAFLFLVAFV GCCGACKENY CLMITFAIFL SLIMLVEVAV AIAGYVFRDQ VKSEFNKSFQ  120
QQMQNYLKDN KTATILDKLQ KENNCCGASN YTDWENIPGM AKDRVPDSCC INITVGCGND  180
FKESTIHTQG CVETIAIWLR KNILLVAAAA LGIAFVEVLG IIFSCCLVKS IRSGYEVM    238

SEQ ID NO: 5            moltype = DNA   length = 1321
FEATURE                 Location/Qualifiers
source                  1..1321
                        mol_type = other DNA
                        organism = Homo sapiens
CDS                     185..871
SEQUENCE: 5
cttttcccgg cacatgcgca ccgcagcggg tcgcgcgccc taaggagtgg cacttttaa    60
aagtgcagcc ggagaccagc ctacagccgc ctgcatctgt atccagcgcc aggtccgcc   120
agtcccagct gcgcgcgccc cccagtcccg caccgttcg gcccaggcta agttagcct   180
caccatgccg gtcaaaggag gcaccaagtg catcaaatac tgctgttcg gatttaactt   240
catcttctgg cttgccggga ttgctgtcct tgccattgga ctatgccgtc gattcgactc   300
tcagaccaag agcatcttcg agcaagaaac taataataat aattccagct tctacacagg   360
agtctatatt ctgatcggag ccggcgcctc catgatgctg gtgggcttcc tgggctgctg   420
cggggctgtg caggagtccc agtgcatgct gggactgttc ttcggcttcc tcttggtgat   480
attccgcatt gaaatagctg cggccatctg gggatattcc acaaggatg aggtgattaa   540
ggaagtccag gagttttaca ggacaccta caacaagctg aaaaccaagg atgagcccca   600
gcgggaaacg ctgaaagcca tccactatgc gttgaactgc tgtgggttgg ctgggggcgt   660
ggaacagttt atctcagaca tctgcccaa gaaggacgta ctcgaaacct tcaccgtgaa   720
gtcctgtcct gatgccatca aagaggtctt cgacaatgaa ttccacatca tcggcgcagt   780
gggcatcggc attgccgtgg tcatgatatt tggcatgatc ttcagtatga tcttgtgctg   840
tgctatccgc aggaaccgcg agatggtcta gagtcagctt acatccctga caggaaagt   900
ttacccatga agattggtgg gatttttgtt ttgtttgttt tgttttgttt gttgtttgtt   960
gtttgttttt ttgccactaa ttttagtatt cattctgcat tgctagataa aagctgaagt  1020
tactttatgt ttgtctttta atgcttcatt caatattgac atttgtagtt gagcggggg   1080
tttggtttgc tttggtttat attttttcag ttgtttgttt ttgcttgtta tattaagcag  1140
aaatcctgca atgaaaggta ctatatttgc tagactctag acaagatatt gtacataaa   1200
gaattttttt gtctttaaat agatacaaat gtctatcaac tttaatcaag ttgtaactta  1260
tattgaagac aatttgatac ataataaaaa attatgacaa tgtcctggac tggtaaaaaa  1320
a                                                                  1321

SEQ ID NO: 6            moltype = AA   length = 228
FEATURE                 Location/Qualifiers
source                  1..228
                        mol_type = protein
                        organism = Homo sapiens
SEQUENCE: 6
MPVKGGTKCI KYLLFGFNFI FWLAGIAVLA IGLWLRFDSQ TKSIFEQETN NNNSSFYTGV   60
YILIGAGALM MLVGFLGCCG AVQESQCMLG LFFGFLLVIF AIEIAAAIWG YSHKDEVIKE  120
VQEFYKDTYN KLKTKDEPQR ETLKAIHYAL NCCGLAGGVE QFISDICPKK DVLETFTVKS  180
CPDAIKEVFD NKFHIIGAVG IGIAVVMIFG MIFSMILCCA IRRNREMV               228

SEQ ID NO: 7            moltype = DNA   length = 1306
FEATURE                 Location/Qualifiers
```

```
source                  1..1306
                        mol_type = other DNA
                        organism = Mus musculus
CDS                     117..797
SEQUENCE: 7
tttttaaaag tggagcctca ggccagcccc tagccgcagc gtgtctcagt cggttgtcga   60
gtcccttctg tcccagtcgt tcgtgcctct tgtcccacgc aactccagct tgtaccatgc  120
cggtcaaagg aggtagcaag tgcatcaaat acctgctctt cggatttaac ttcatcttct  180
ggctcgctgg cattgcagtg cttgctattg gactatggct ccgattcgac tctcagacca  240
agagcatctt cgagcaagag aataaccatt ccagtttcta cacaggagtg tacattctga  300
ttggagccgg ggccctcatg atgctggttg gtttcctggg ctgctgtgga gctgtacaag  360
agtcccagtg catgctggga ttgttcttcg ggttcctctt ggtgatattc gccattgaga  420
tagccgccgc cgtctgggc tatacccaca aggatgaggg gattaaagaa ctccaggagt  480
tttacaagga cacctaccaa aagttacgga gcaaggatga gaaccagcgg gaaacactca  540
aagccatcca tatggcgttg gactgctgtg gcatagctgg tccttgggag cagtttatct  600
cggacacctg cccaagaaa cagctttgg aaagtttcca ggttaagccc tgccctgaag  660
ccatcagtga ggtcttcaac aacaagttcc acatcattgg agcagtgggt atcggcatcg  720
ccgtggtgat gatcttcggc atgatcttca gcatgatcct gtgctgcgcc atccgcagga  780
gccgagaaat ggtctagagt ctgcccaacc ccgagcagga acaacggccc tgaagactgt  840
ccgggccatt tgggtttttt tgccactaa tattagtatt cattatgcat ttctaaataa  900
cagtcattcc gtttgtcttt ttaatgcttt attcattatt gacatttgta gttgagggat  960
ccgggggttc aatttatttt gatttttttt tttggttgtt tattttttgct tgttatgtta 1020
agcaaaaatc ctgcaatgaa aggtactata tttgccagac tctagacata agatattgta 1080
cataaagaga attttttttg cctttaaata gataaaagta tctatcagat aaaaatcagg 1140
ttgtaagtta tattgaagac aatttgatac ataataaaag attataacag tgaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaa                1306

SEQ ID NO: 8            moltype = AA   length = 226
FEATURE                 Location/Qualifiers
source                  1..226
                        mol_type = protein
                        organism = Mus musculus
SEQUENCE: 8
MPVKGGSKCI KYLLFGFNFI FWLAGIAVLA IGLWLRFDSQ TKSIFEQENN HSSFYTGVYI   60
LIGAGALMML VGFLGCCGAV QESQCMLGLF FGFLLVIFAI EIAAAVWGYT HKDEVIKELQ  120
EFYKDTYQKL RSKDEPQRET LKAIHMALDC CGIAGPLEQF ISDTCPKKQL LESFQVKPCP  180
EAISEVFNNK FHIIGAVGIG IAVVMIFGMI FSMILCCAIR RSREMV                 226

SEQ ID NO: 9            moltype = DNA   length = 1379
FEATURE                 Location/Qualifiers
source                  1..1379
                        mol_type = other DNA
                        organism = Homo sapiens
CDS                     329..826
SEQUENCE: 9
tttggttcct tgtggccaca tttccagtac ccagtagtca tctgtgccag ggggttatcc   60
aggtacagaa cattcccatc gttgcagaag gttctatcag ctagcactgg gttggacgac  120
acttgccaag acgagctggc tagaggatgg ttctccggac ctggtccac gtggttccca  180
gctggctgga ggcgtgatcc tgggtgtggc cctgtggctc cgccatgacc gcagaccac  240
caacctcctg tatctggagc tgggagacaa gcccgccgca aacaccttct atgtaggcat  300
ctacatcctc atcgctgtgg gcgctgtcat gatgttcgtt ggcttcctgg gctgctacgg  360
ggccatccag gaatcccagt gcctgctggg gacgttcttc acctgcctgg tcatcctgtt  420
tgcctgtgag gtggccgccg gcatctgggg ctttgtcaac aaggaccaga tcgccaagga  480
tgtgaagcag ttctatgacc aggccctaca gcaggccgtg gtggatgatg acgccaacaa  540
cgccaaggct gtggtgaaga ccttccacga gacgcttgac tgctgtggct ccagcacact  600
gactgctttg accacctcag tgctcaagaa caatttgtgt ccctcgggca gcaacatcat  660
cagcaacctc ttcaaggagg actgccacca gaagatcgat gacctcttct ccgggaagct  720
gtacctcatc ggcattgctg ccatcgtggt cgctgtgatc atgatcttcg agatgatcct  780
gagcatggtg ctgtgctgtg gcatccggaa cagctccgtg tactgaggcc ccgcagctct  840
ggccacaggg acctctgcag tgcccctaa gtgacccgga cacttccgag ggggccatca  900
ccgcctgtgt atataacgtt tccggtatta tctgctacta cgtagccttt ttactttgg  960
ggttttgttt ttgttctgaa cttcctgtt accttcag ggctgacgtc acatgtaggt 1020
ggcgtgtatg agtggagacg ggcctgggtc ttggggactg gagggcaggg gtccttctga 1080
cctggggtcc cagggtgctc tgcctgctca gccaggcctc tcctgggagc cactcgccca 1140
gagactcagc ttgccaact tggggggctg tgtccaccca gcccgccgt cctgtgggct 1200
gcacagctca ccttgttccc tcctgccccg gttcgagagc cgagtctgtg ggcactctct 1260
gccttcatgc acctgtcctt tctaaacacgt cgccttcaac tgtaatcaca acatcctgac 1320
tccgtcattt aataaagaag gaacatcagg catgctacca ggcctgtgca gtccctcag  1379

SEQ ID NO: 10           moltype = AA   length = 165
FEATURE                 Location/Qualifiers
source                  1..165
                        mol_type = protein
                        organism = Homo sapiens
SEQUENCE: 10
MMFVGFLGCY GAIQESQCLL GTFFTCLVIL FACEVAAGIW GFVNKDQIAK DVKQFYDQAL   60
QQAVDDDAN NAKAVVKTFH ETLDCCGSST LTALTTSVLK NNLCPSGSNI ISNLFKEDCH  120
QKIDDLFSGK LYLIGIAAIV VAVIMIFEMI LSMVLCCGIR NSSVY                 165
```

| SEQ ID NO: 11 | moltype = DNA length = 1534 |
|---|---|
| FEATURE | Location/Qualifiers |
| source | 1..1534 |
| | mol_type = other DNA |
| | organism = Mus musculus |
| CDS | 252..962 |

SEQUENCE: 11

```
gaggtctata aagagtgagg agctaggcgc gcgcgcccgg tccgagcgag cgcgtccttg   60
cttcaaagag atagtgactc tcgcgcctcc ggctaggcct ccagcccttc tctaccctac  120
gtctcattct ccgcaacgca gttctccggc ccgcaagcgc tccaggctat ctgccagtcc  180
cggaccccgg tactgcgtcc ccataccgcc cgctccagga ccaatccaag ctccgcaggc  240
cgcgcaccgc catgggggtg gagggctgca ccaaatgcat caaatacctg ctcttcgtct  300
tcaatttcgt cttctggctg gctgaggcg tgatcctagg tgtagctctg tggttgcgtc  360
atgatccaca daccaccagc ctgctgtacc tggaactggg aaacaaaccg gcacccaaca  420
ccttctacgt gggcatctac attctcattg ctgtgggagc tgtgatgatg tttgtaggct  480
tcctggggtg ctatggggcc atccaggagt cccagtgtct gctggggacg ttcttcacct  540
gccttgtgat cctgtttgcc tgtgaggtgg ctgcaggcat ctgggggttc gtaaacaaag  600
accagatcgc caaggatgtg aagcagttct atgaccagge ccttcagcaa gctgtgatgg  660
atgatgatgc caacaatgcc aaggctgtgg tgaagacttt ccatgagacg ctcaactgtt  720
gtggctccaa cgcactgacc acactgacta ccaccatact gaggaacagc ctgtgtccct  780
caggcggcaa catactcacc cccttactgc agcaagattg tcatcagaaa atcgatgagc  840
tcttctctgg gaagctgtac ctcattggaa ttgcagccat tgtggtagct gtcattatga  900
tctttgagat gattctgagc atggtgctgt gctgtggcat ccggaacagc tccgtgtact  960
gaggcccttt gcattgcacc agaggatccc tggagtgacc agaggccacc ttgggggaca 1020
tggcctgtgt atataatatt tctgtatcac tctgctacca ttagtctttt tacttttgag 1080
tttttttgttt tgttttgttt tgttttttgtt ttagttttttt ttttttgtcct gaacttttcc 1140
tgttacctttt tgggagctga catcacacat gggtggcata tgtgggatgt aggggtggag 1200
ctggccctgg cttgcagggc cctgtacgtc tgggacccct ggagagttct gcctgctgag 1260
ccaaacctcc tctacagcta cttgcccaga ggctttgtag cctagctaga gggccatgcc 1320
cacccactca acccactgtg ggtcacattg ctcacatctt tttaatcttt gttcctttcc 1380
tgcctccatt tcaagagctg ggtttgtaag ccctcttatg ccttcaatgc acttattctt 1440
tctaacgtgt caccttcaac tgtaattaaa tcttgaaaca gtcatttaat aaggaggaa  1500
aaaaatcagg catgctaaaa aaaaaaaaaa aaaa                              1534
```

| SEQ ID NO: 12 | moltype = AA length = 236 |
|---|---|
| FEATURE | Location/Qualifiers |
| source | 1..236 |
| | mol_type = protein |
| | organism = Mus musculus |

SEQUENCE: 12

```
MGVEGCTKCI KYLLFVFNFV FWLAGGVILG VALWLRHDPQ TTSLLYLELG NKPAPNTFYV   60
GIYILIAVGA VMMFVGFLGC YGAIQESQCL LGTFFTCLVI LFACEVAAGI WGFVNKDQIA  120
KDVKQFYDQA LQQAVMDDDA NNAKVVVKTF HETLNCCGSN ALTTLTTTIL RNSLCPSGGN  180
ILTPLLQQDC HQKIDELFSG KLYLIGIAAI VVAVIMIFEM ILSMVLCCGI RNSSVY      236
```

| SEQ ID NO: 13 | moltype = DNA length = 4288 |
|---|---|
| FEATURE | Location/Qualifiers |
| source | 1..4288 |
| | mol_type = other DNA |
| | organism = Mus musculus |
| CDS | 185..1960 |

SEQUENCE: 13

```
ggacgcgggg ttgggcttcg tgcggtgggg ctcgctcgcg cggcggccgt agccgaggcc   60
tcttagttct gcggcacgtg acggtcgggc cgcctctgcg gctgtctcca ctgcagcacg  120
gggccgggtg tgcgggtggg agaaggtgag ggagccgcca gtggtccccg ggaggctcga  180
gatcatggaa gggaagtggt tactgtgttt gctgctggtc cttggaactg cagctgttga  240
ggctcatgat ggacatgatg atgacgcgat tgatattgaa gatgatcttg atgatgttat  300
tgaagaggta gaagattcaa aatctaaatc agatgccagc actcctccat ctccaaaggt  360
cacctacaaa gctccagttc caacaggga ggtttatttt gctgactcct ttgcagagg  420
gtctctgtca gggtggattt tatctaaagc caaaaaagat gacactgatg atgaaattgc  480
caaatatgat ggaagtggg aagtagatga gatgaaggaa acaaagcttc caggggataa  540
aggacttgta ctgatgtctc gggccaagca tcatgccatc tctgctaaac tgaataagcc  600
cttcctgttt gataccaagc ctctcattgt tcagtatgag gttaattttc agaatgaagt  660
agaatgtggt ggtgcctatg tgaagctgct ttccaagacg gcagagctca gcctggatca  720
attccacgac aagactccct atactattat gtttggtcca gataagtgtg agaggacta  780
caaactgcat ttcatctttc gacacaaaaa tcccaagaca ggtgtatatg aagaaaaaca  840
tgctaagagg ccagatgcag atctgaagac tcatttcact gacaagaaaa cgcatcttta  900
tacattaatc ttgaatccag acaatagttt tgaaatatta gttgaccagt ctgttgtgaa  960
cagtggaaat ctgctaaatg acatgactcc tcctgtaaac ccttcacgtg aaattgaaga 1020
cccagaagac cggaagcctg aagatttggga tgaaaggccc aaaatagcag atccagatgc 1080
tgtcaagcca gatgactggg atgaagacgc cccttctaag atcccagatg aagaggccac 1140
caagcctgaa ggctggctag acgacgaacc tgagtatatt ccagccctg atgcagaaa 1200
gccagaagat tgggatgagg atatgacgg agaatgggaa gctcctcaga ttgccaaccc 1260
caagtgtgag tcagcccctg ggtgtggtgt ctggcagcga cctatgatg acaacccaa 1320
ttataagggc aaatgaagc ctccaatgat tgacaaccct aactaccagg aatctggaa 1380
accaaggaaa ataccaaatc cagatttctt tgaagaccta aaccttttta agatgactcc 1440
tttcagtgct attggtttgg agctctggtc catgacatcc gacatcttttt tgacaacttt 1500
tatcattagt ggtgaccgaa gagtagttga tgattgggcc aatgatgggt ggggcctgaa 1560
```

-continued

```
gaaagctgct gatggggctg ctgagccagg tgtagtgctg cagatgctgg aggcagctga   1620
agagcgtcca tggctttggg tggtctacat tttgactgta gctttgccag tgttccttgt   1680
gatcctcttc tgctgttctg gaaagaaaca gtccaatgct atggagtaca agaagacgga   1740
tgctccccag ccagatgtga aggatgaaga agggaaggaa gaagagaaga acaagaggga   1800
tgaagaggaa gaagaggaga agcttgaaga gaaacagaag agtgatgctg aagaagatgg   1860
tgttactggc agtcaagatg aggaagatag caagcctaaa gcagaggagg atgaaatttt   1920
gaacagatcg ccaagaaaca gaaagccacg aagagagtga aacaatcttt aagaacttga   1980
tctgtgattt cctctccctc cccttcccct gcaaatgtgg tcctaggaga gggcctggtg   2040
taccttaggt gggagctcaa aacctcaaga tgtcaccatc aacaggttcc agtgaatact   2100
agcctgtaat tttaaacatc tagcagtaaa taattgcagt tgtaatgtaa aggacccctgt  2160
ttctgtagaa aggaaacat ttaacataat ggttgtgaaa tgtaacatga agcaactaac    2220
tagtgttttg ttgttttttaa aattttccag gtttgtcttt ttttttttcc ttttcctttt   2280
ttttttttt ttagatacaa tgatagaatt tttgccagtt taaaatccttg gcttaattta    2340
atatattcat ttgttcatgc agaaataaca ccaacattag gaatgctagg gagaatgaat   2400
tgccgttttt ataataactt ttttaagttt ggtattaaag cattcatgtg tctgtcctaa    2460
aattgtaatc acgttcaagt gcagttattt gtggttataa atcttgtttt gtgtgcttcc    2520
attagttaat tcctctttaaa gacacaagag cgattggatg gaagcccaaa tttatatcaa   2580
agttccctt acattgtatt gaatagaccc aaaaagaact aaaaggagac tttgacttgg    2640
tcatttcaca tcagatcata aagtgcagtg ttctgttgcc ctagagactg ctccattcac    2700
aagcaccttt gaagagggaa ggagctggct tcatgtagca gttcatactg tacttcccac    2760
ataggaggtc tgacagctcg ggtcctctgg agcacaaggc ttttaagga atgctggtgg     2820
tgcctgggta gataattaca tcacttgttc cactgtgttg acactgtttt cctcatggat    2880
ctcctccatt cctagctttc tctgctatgc attttcttca cagcgcagct tgcggtccgt    2940
tgctgaaaat tataagctct gcatagtgtt ggctttactg tgatgacatg tttcttcttt    3000
tttagctggc ccacaccttt ctagggtcca actacaggat agattacaga cttttccatta  3060
gtgtctattt cttttactct gtgtagactt tagaaagtct aatcaatcca gagatgggcc    3120
aattcagaat tgactataat tgaacacctg ctaaaagtat ttatgggagg attgacacac   3180
agcatgagtt atttgacttt tgtaggatat ttaaaatctt catttgcagt tcatgtaaca    3240
gttgtgtctt aaaattcaca taataaagca gtcctgttca aaaaaaaat ttttttttg     3300
tggcttgtag aatttttaa aagtgtattt agggctttt gttttttgtt tgttttttg     3360
ttttgttttt catgtggaat gcagatgggt gctagaggag cctctcccac atcactatag   3420
tgtaatatta ttcaccaca ctgaaatgta ttcagaaaca gatgtttcaa tttcattctt     3480
tctccagagg tggtccagtt gtaccaatga tactattcct tgcactgaat atatataaac   3540
actcttcagt gtttatattg ggaaaatact gggaaagaaa tatatttgtt aaggatgaag   3600
gctgtatctg ttgtctttat aaacactggt tcatttcttt tgagggtgga atgcattttt    3660
cttcctgttc agtgctttat caccatctgt tgtttgtggt cacagtgacc atagctatgt   3720
agcggacgtt tccaaatgta tagagtgaaa taaacagtta ctagcaagaa atgaatacat    3780
gtctgcaggt ttctccttga agcaaacatg gggatgattg cttttctaga aatcggttta    3840
tctgtttcat cattctacat tgacattgtt ttgtgcctac tttatattca cccaggctgt    3900
acaatgacag gtttatttat gtcactggtg gtggtcattg ccttttttggg tccctcttcc   3960
tccctcaagg ttccattgaa gctccagcct ccttaaatac ctgactcgtt agtaaatgat    4020
cagcagtctt cagctcttaa aaaaagcgta gagggcaggt attgtagctg agtaggtaga    4080
actgctaagc gtgtgcaagg ttccgtgggt ctgattcctg gcactgaatt aagatagata    4140
aaggccctta tattctgatt ttctatgctg gactccttgt tgtaaaatgt ccatgccagt    4200
agtactcttc tattgtccac ttttcagatt gtcacactgc taaatgacat tatattaaag    4260
cccgtgttaa atatctgtat cataaaaa                                        4288

SEQ ID NO: 14          moltype = AA   length = 591
FEATURE                Location/Qualifiers
source                 1..591
                       mol_type = protein
                       organism = Mus musculus
SEQUENCE: 14
MEGKWLLCLL LVLGTAAVEA HDGHDDDAID IEDDLDDVIE EVEDSKSKSD ASTPPSPKVT   60
YKAPVPTGEV YFADSFDRGS LSGWILSKAK KDDTDDEIAK YDGKWEVDEM KETKLPGDKG   120
LVLMSRAKHH AISAKLNKPF LFDTKPLIVQ YEVNFQNGIE CGGAYVKLLS KTAELSLDQF   180
HDKTPYTIMF GPDKCGEDYK LHFIFRHKNP KTGVYEEKHA KRPDADLKTY FTDKKTHLYT   240
LILNPDNSFE ILVDQSVVNS GNLLNDMTPP VNPSREIEDP EDRKPEDWDE RPKIADPDAV   300
KPDDWDEDAP SKIPDEEATK PEGWLDDEPE YIPDPDAEKP EDWDEDMDGE WEAPQIANPK   360
CESAPGCGVW QRPMIDNPNY KGKWKPPMID NPNYQGIWKP RKIPNPDFFE DLEPFKMTPF   420
SAIGLELWSM TSDIFFDNFI ISGDRRVVDD WANDGWGLKK AADGAAEPGV VLQMLEAAEE   480
RPWLWVVYIL TVALPVFLVI LFCCSGKKQS NAMEYKKTDA PQPDVKDEEG KEEEKNKRDE   540
EEEEEKLEEK QKSDAEEDGV TGSQDEEDSK PKAEEDEILN RSPRNRKPRR E            591

SEQ ID NO: 15          moltype = DNA   length = 1873
FEATURE                Location/Qualifiers
source                 1..1873
                       mol_type = other DNA
                       organism = Gallus gallus
CDS                    66..1226
SEQUENCE: 15
gacatacagc tagaaagctg tattgccttt agcactcaag ctcaaaagac aactcagagt    60
tcaccatggg ctccatcggc gcagcaagca tggaattttg ttttgatgta ttcaaggagc   120
tcaaagtcca ccatgccaat gagaacatct tctactgcc cattgccatc atgtcagctc   180
tagccatggt ataccctggt gcaaaagaca gcaccaggac acagataaat aaggttgttc   240
gctttgataa acttccagga ttcggagaca gtattgaagc tcagtgtggc acatctgtaa   300
acgttcactc ttcacttaga gacatcctca accaaatcac caaaccaaat gatgtttatt   360
cgttcagcct tgccagtaga cttttatgctg aagagagata cccaatcctg ccagaatact   420
tgcagtgtgt gaaggaactg tatagaggag gcttggaacc tatcaacttt caaacagctg   480
```

```
cagatcaagc cagagagctc atcaattcct gggtagaaag tcagacaaat ggaattatca    540
gaaatgtcct tcagccaagc tccgtggatt ctcaaactgc aatggttctg gttaatgcca    600
ttgtcttcaa aggactgtgg gagaaaacat ttaaggatga agacacacaa gcaatgcctt    660
tcagagtgac tgagcaagaa agcaaacctg tgcagatgat gtaccagatt ggtttattta    720
gagtggcatc aatggcttct gagaaaatga agatcctgga gcttccattt gccagtggga    780
caatgagcat gttggtgctg ttgcctgatg aagtctcagg ccttgagcag cttgagagta    840
taatcaactt tgaaaaactg actgaatgga ccagttctaa tgttatggaa gagaggaaga    900
tcaaagtgta cttacctcgc atgaagatgg aggaaaaata caacctcaca tctgtcttaa    960
tggctatggg cattactgac gtgtttagct cttcagccaa tctgtctggc atctcctcag   1020
cagagagcct gaagatatct caagctgtcc atgcagcaca tgcagaaatc aatgaagcag   1080
gcagagaggt ggtagggtca gcagaggctg gagtggatgc tgcaagcgtc tctgaagaat   1140
ttagggctga ccatccattc ctcttctgta tcaagcacat cgcaaccaac gccgttctct   1200
tctttggcag atgtgtttcc ccttaaaaag aagaaagctg aaaaactctg tcccttccaa   1260
caagacccag agcactgtag tatcaggggt aaaatgaaaa gtatgttctc tgctgcatcc   1320
agacttcata aaagctggag cttaatctag aaaaaaaatc agaaagaaat tacactgtga   1380
gaacaggtgc aattcacttt tcctttacac agagtaatac tggtaactca tggatgaagg   1440
cttaaggaa tgaaattgga ctcacagtac tgagtcatca cactgaaaaa tgcaacctga    1500
tacatcagca gaaggtttat ggggaaaaa tgcagcctc caattaagcc agatatctgt     1560
atgaccaagc tgctccagaa ttagtcactc aaaatctctc agattaaatt atcaactgtc   1620
accaaccatt cctatgctga caaggcaatt gcttgttctc tgtgttcctg atactacaag   1680
gctcttcctg acttcctaaa gatgcattat aaaaatctta taattcacat ttctccctaa   1740
actttgactc aatcatggta tgttggcaaa tatggtatat tactattcaa attgttttcc   1800
ttgtacccat atgtaatggg tcttgtgaat gtgctctttt gttcctttaa tcataataaa   1860
aacatgttta agc                                                      1873

SEQ ID NO: 16          moltype = AA  length = 386
FEATURE                Location/Qualifiers
source                 1..386
                       mol_type = protein
                       organism = Gallus gallus
SEQUENCE: 16
MGSIGAASME FCFDVFKELK VHHANENIFY CPIAIMSALA MVYLGAKDST RTQINKVVRF     60
DKLPGFGDSI EAQCGTSVNV HSSLRDILNQ ITKPNDVYSF SLASRLYAEE RYPILPEYLQ    120
CVKELYRGGL EPINFQTAAD QARELINSWV ESQTNGIIRN VLQPSSVDSQ TAMVLVNAIV    180
FKGLWEKTFK DEDTQAMPFR VTEQESKPVQ MMYQIGLFRV ASMASEKMKI LELPFASGTM    240
SMLVLLPDEV SGLEQLESII NFEKLTEWTS SNVMEERKIK VYLPRMKMEE KYNLTSVLMA    300
MGITDVFSSS ANLSGISSAE SLKISQAVHA AHAEINEAGR EVVGSAEAGV DAASVSEEFR    360
ADHPFLFCIK HIATNAVLFF GRCVSP                                         386
```

EXOSOME-TARGETED DNA VACCINE

The contents of the electronic sequence listing 692188_408D2_SEQUENCE_LISTING.xml; 32, 768 bytes and date of creation: Aug. 10, 2023 is herein incorporated by reference in its entirety.

TECHNICAL FIELD

The present invention relates to a novel DNA vaccine. More specifically, the present invention relates to an exosome targeting DNA vaccine and a technology of a novel DNA vaccine with excellent ability to induce cytotoxic T cells for expressing a fusion antigen of an exosome (extracellular microparticle) constituting protein and a vaccine antigen.

BACKGROUND ART

DNA vaccines were developed about 20 years ago, but they still have not been in clinical use on humans. The reasons therefor include: expected immunogenicity cannot be attained; risk of integration into the genome and the associated risk of oncogenesis; risk of inducing an autoimmune disease against the genome after administration of a DNA vaccine; and risk of acquiring drug resistance after administrating a DNA vaccine with a plasmid to which a sequence of an antibiotics is incorporated. Improvement of DNA vaccines is ongoing worldwide.

Non Patent Literature 1 discloses that an antigen is encapsulated into an exosome and the exosome is administered to a mouse to induce a Th1-type T cell response.

Patent Literature 1 discloses a technology related to a complex comprising an exosome and drug delivery.

Non Patent Literature 2 discloses that virus like particles (extracellular microparticles) are released from cells after administration of a DNA vaccine with a plasmid, in which an (OVA) is fused with an HIV-1 Gag protein.

CITATION LIST

Patent Literature

[PTL 1] International Publication No. WO 2014054588 A1

Non Patent Literature

[NPL 1] Blood, 19 Mar. 2009, vol. 113, num. 12, 2673-2683.
[NPL 2] Journal of Extracellular Vesicles, 2014, 3:24646.

SUMMARY OF INVENTION

Solution to Problem

In order to provide a DNA vaccine that can be used clinically on humans and to further enhance antigenicity, the inventors focused on exosomes, which have drawn attention as a tool for DDS, to find that such a DNA vaccine has excellent ability to induce cytotoxic T cells inducing capability for expressing a fusion antigen of an exosome (extracellular microparticle) constituting protein and a vaccine antigen.

Specifically, a plasmid DNA that expresses an antigen made by fusing an antigen (OVA: ovalbumin) and CD63, which is a tetraspanin family protein that is commonly known and used as a marker for exosomes, was prepared. When a mouse was immunized with this plasmid DNA, enhancement in T cell responses was observed in a DNA vaccine administration group expressing a fusion antigen of CD63, relative to a DNA vaccine administration group expressing OVA alone. An increase in the antigen specific CTL (cytotoxic T cells) count was also observed. Furthermore, tumor cells expressing OVA were transplanted into a mouse, and the prepared plasmid DNA was administered once after 7 days from the transplantation. As a result, tumor growth was significantly suppressed compared to an expression vector administration group. In view of the above, a DNA vaccine expressing a fusion antigen of an exosome marker protein CD63 and a vaccine antigen was found to be useful as a novel prophylactic/therapeutic technology that enhances the ability to induce antigen specific CTLs.

(1) A nucleic acid construct comprising a nucleic acid sequence encoding an exosome marker protein and a nucleic acid sequence encoding a vaccine antigen.
(2) The nucleic acid construct of item 1, wherein the exosome marker protein is a protein that is present in a membrane of an exosome.
(3) The nucleic acid construct of item 1 or 2, wherein the exosome marker protein belongs to the tetraspanin family.
(4) The nucleic acid construct of any one of items 1 to 3, wherein the exosome marker protein is selected from the group consisting of CD63, CD81, CD9, CD31, HLA-G, TSG101, Rab5b, and ALIX.
(5) The nucleic acid construct of any one of items 1 to 4, wherein the exosome marker protein is selected from the group consisting of CD63, CD81, and CD9.
(6) The nucleic acid construct of any one of items 1 to 5, wherein the antigen is selected from a cancer antigen and a viral antigen.
(7) The nucleic acid construct of any one of items 1 to 6, which is a plasmid DNA.
(8) A DNA vaccine comprising the nucleic acid construct of any one of items 1 to 7.
(9) The DNA vaccine of item 8 for improving Th1-type immunity induction.
(10) The DNA vaccine of item 8 or 9, characterized in targeting cancer or a viral disease.
(11) A protein in a form of a vaccine antigen protein fused with an exosome marker protein.
(11A) The protein of item 11, further comprising one or more features of the preceding items.
(12) An exosome comprising a vaccine antigen protein and an exosome marker protein in a fused form.
(12A) The exosome of item 12, further comprising one or more features of the preceding items.
(13) An immune response enhancer comprising the nucleic acid construct of any one of items 1 to 7, the DNA vaccine of items 8 to 10, the protein of item 11 or 11A, or the exosome of item 12 or 12A.
(14) A composition for enhancing a T cell response comprising the nucleic acid construct of any one of items 1 to 7, the DNA vaccine of items 8 to 10, the protein of item 11 or 11A, or the exosome of item 12 or 12A.
(15) A cytotoxic agent comprising the nucleic acid construct of any one of items 1 to 7, the DNA vaccine of items 8 to 10, the protein of item 11 or 11A, or the exosome of item 12 or 12A.
(16) A medicament comprising the nucleic acid construct of any one of items 1 to 7, the DNA vaccine of items 8 to 10, the protein of item 11 or 11A, or the exosome of item 12 or 12A.

(17) A medicament for treating or preventing cancer comprising the nucleic acid construct of any one of items 1 to 9, the DNA vaccine of items 10, the protein of item 11 or 11A, or the exosome of item 12 or 12A.

(18) A method of enhancing an immune response in a subject, comprising administering to the subject an effective amount of the nucleic acid construct of any one of items 1 to 7, the DNA vaccine of items 8 to 10, the protein of item 11 or 11A, or the exosome of item 12 or 12A.

(19) A method of enhancing a T cell response, comprising administering to a subject an effective amount of the nucleic acid construct of any one of items 1 to 7, the DNA vaccine of items 8 to 10, the protein of item 11 or 11A, or the exosome of item 12 or 12A.

(20) A method of treating or preventing cancer, comprising administering to a subject an effective amount of the nucleic acid construct of any one of items 1 to 7, the DNA vaccine of items 8 to 10, the protein of item 11 or 11A, or the exosome of item 12 or 12A.

(21) A composition for improving immunogenicity of a vaccine DNA, comprising a nucleic acid sequence encoding an exosome marker protein.

(22) The composition of item 21, wherein the exosome marker protein is a protein that is present in a membrane of an exosome.

(23) The composition of item 21 or 22, wherein the exosome marker protein belongs to the tetraspanin family.

(24) The composition of any one of items 21 to 23, wherein the exosome marker protein is selected from the group consisting of CD63, CD81, CD9, CD31, HLA-G, TSG101, Rab5b, and ALIX.

(25) The composition of any one of items 21 to 24, wherein the exosome marker protein is selected from the group consisting of CD63, CD81, and CD9.

(26) The composition of any one of items 21 to 25, wherein an antigen contained in the vaccine DNA is selected from a cancer antigen and a viral antigen.

(27) The composition of any one of items 21 to 26, wherein the vaccine DNA is a plasmid DNA.

(27A) The composition of any one of items 21 to 27, further comprising one or more features of items 1 to 11, 11A, 12, 12A, and 13 to 20.

The present invention is intended so that one or more of the above features can be provided as the explicitly disclosed combinations as well as other combinations thereof. Additional embodiments and advantages of the present invention are recognized by those skilled in the art by reading and understanding the following detailed explanation, as needed.

Advantageous Effects of Invention

The present invention achieves an effect of providing a clinically-applicable DNA vaccine, which was not previously attainable. For example, administration of the DNA vaccine of the invention induces a strong antigen specific T cell response such as an antigen specific $CD8^+$ T cell response, which is stronger than administration of a conventional antigen-containing exosome itself. Further, stronger cytotoxic activity is observed from administration of the DNA vaccine of the invention. A high therapeutic effect on tumor is also observed from administration of the DNA vaccine of the invention. It has been elucidated from the above that the immunogenicity of a DNA vaccine can be improved by targeting an antigen of a DNA vaccine to an exosome.

The present invention shows that expression of IgG2 (c) increases more than IgG1 by using a protein of the tetraspanin family, and Th1-type immune responses, i.e., cellular immunity (especially $CD8^+$ T cell responses) are enhanced for a DNA vaccine, as shown in the Examples.

The result achieved by the present invention shows that a clinically applicable DNA vaccine, which can strongly induce an antigen specific $CD8^+$ T cell, can be provided by targeting an antigen of the DNA vaccine to an exosome. As demonstrated in the Examples, immunization with a purified OVA-containing exosome can elicit induction of OVA-specific $CD4^+$ and $CD8^+$ T cells in naïve mice. Meanwhile, this was not elicited by immunization with an exosome purified from cells transfected with a control plasmid encoding a calnexin-OVA fusion protein targeting vesicles or only OVA proteins. Vaccination of a mouse with pCD63-OVA induced a potent antigen specific T cell response, especially $CD8^+$ T cell response. In addition, exosome targeting with CD63 resulted in a better $CD8^+$ T cell response than ER targeting with calnexin. As demonstrated in the Examples, vaccination with exosome targeting DNA significantly inhibited tumor growth compared to control DNA vaccine inoculation when the inventors used a mouse tumor transplantation model for evaluating pCD63-OVA as a therapeutic vaccine. The results of the present invention show that antigen targeting to an exosome with DNA vaccine inoculation can be a tool for eliciting a potent $CD8^+$ T cell response to an encoded antigen and can be useful as a cancer vaccine. The same effect with CD63 was also confirmed for tetraspanins CD9 and CD81.

The present invention can be advantageous in terms of better actual immunization method or the like. Although not wishing to be bound by any theory, DNA vaccines are more advantageous than the exosome itself because autologous (e.g., patients' own) exosome may need to be collected and administered in clinical practice, but MHC class I or class II is expressed.

The present invention, in a form of a DNA vaccine, can be readily prepared and administered to basically anyone, which is one of the advantages over single exosome administration. Furthermore, the effect attained by the present invention is higher than the level that can be achieved by conventional art in view of the amount of DNA plasmid used or the like. Further, manufacture of an antigen containing exosome was in itself difficult with conventional methods when manufacturing exosomes, but one of the advantages of the present invention is that an antigen can be readily expressed in an exosome by using a DNA plasmid (vaccine). In this manner, this is superior to administration of exosome itself with respect to various points. Other notably advantages include when an autologous cell is used, an antigen can be readily expressed in an exosome with a DNA vaccine and this can be readily administered as a DNA vaccine, so that a different approach can be used and the applicable scope is broadened.

Since IgG2c increases and IgG1 decreases, this proves that cell-mediated immune response (Th1) is proven to be significant. Thus, it is understood that the present invention can be more advantageously used in treating an infection, cancer, or the like requiring induction of a Th1-type immune response.

BRIEF DESCRIPTION OF DRAWINGS

FIG. 1A Evaluation of antigen expressing exosomes as a CTL inducing immunogen. (A, B) An empty vector, pOVA, pCD63, pCD63-OVA, or pCal-OVA was transiently transfected into 293-F cells and 293T cells. After 48 hours from transfection, the supernatant was separated from the cells, and the exosome fraction was purified. (A) The cell, supernatant, and exosome fractions were analyzed by immunoblotting. (B) ELISA was used on the cells and supernatant to analyze the OVA protein concentration. The error bar represents the SD. The labels a, b, and c indicate cell, supernatant, and exosome fractions, respectively.

FIG. 1C Evaluation of antigen expressing exosomes as a CTL inducing immunogen. (C) Detection of exosomes with a scanning electron microscope. The left scanning electron microscope image shows an empty vector transfected 293F cell derived exosome, which is a negative control. The right scanning electron microscope image shows a pCD63-OVA transfected 293F cell derived exosome. The scale bar indicates 100 nm.

FIG. 1D Evaluation of antigen expressing exosomes as a CTL inducing immunogen. C57BL/6J mice (n=6) were immunized by introducing an OVA protein or purified exosome isolated from pOVA transfected cells, pCD63-OVA transfected cells, or pCal-OVA transfected cells through a transdermal route. On day 14 after immunization on day 0 and day 7, the serum and the spleen were used to measure the OVA specific IgG titer, OVA specific serum IgG1 titer, and OVA specific serum IgG2c titer. The vertical axis indicates the respective logarithmic antibody titer. Data represents two independent experiments. The error bar represents the SD.** indicates p<0.005 (Mann-Whitney U test). As for the horizontal axis labels, OVA, CD63-OVA, and Cal-OVA indicate the use of a purified exosome isolated from, from the left, pOVA transfected cells, pCD63-OVA transfected cells, and pCal-OVA transfected cells, respectively. OVA protein indicates the use of an OVA protein, and NC indicates a negative control.

FIG. 1F Evaluation of antigen expressing exosomes as a CTL inducing immunogen. C57BL/6J mice (n=6) were immunized by introducing an OVA protein or purified exosome isolated from pOVA transfected cells, pCD63-OVA transfected cells, or pCal-OVA transfected cells through a transdermal route. On day 14 after immunization on day 0 and day 7, the serum and the spleen were used to measure the ratio of $CD8^+$ T cells recognized by an $OVA_{257-264}$ specific tetramer. The top diagram shows results of FACS analysis on CD44 and OVA class I tetramer, and the bottom diagram shows the ratio of cells in the encircled region in the top diagram. Data represents two independent experiments. ** indicates p<0.005 (Mann-Whitney U test). As for the bar labels, a, b, c, and d indicate medium, $OVA_{257-264}$, $OVA_{323-339}$, and OVA, respectively. As for the horizontal axis labels, OVA, CD63-OVA, and Cal-OVA indicate the use of a purified exosome isolated from, from the left, pOVA transfected cells, pCD63-OVA transfected cells, and pCal-OVA transfected cells, respectively. OVA protein indicates the use of an OVA protein, and NC indicates a negative control.

FIG. 1G C57BL/6J mice (n=5) were immunized by introducing an OVA protein or purified exosome isolated from pCD63 transfected cells, pOVA transfected cells, pCD63-OVA transfected cells, or pCalnexin-OVA transfected cells through a transdermal route. On day 35 after immunization on day 0, day 14, and day 28, the spleen was used to measure the ratio of $CD8^+$ T cells recognized by an $OVA_{257-264}$ specific tetramer. As for the horizontal axis labels, OVA, CD63-OVA, and Calnexin-OVA indicate the use of a purified exosome isolated from, from the left, pCD63 transfected cells, pOVA transfected cells, pCD63-OVA transfected cells, and pCalnexin-OVA transfected cells, respectively.

FIG. 2A The effect of antigen targeting to an exosome on immunogenicity of a DNA vaccine. (A-C) C57BL/6J mice (n=6) were immunized by introducing pOVA, pCD63, or pCD63-OVA by intramuscular electroporation (50 μg/mouse). On day 21 after immunization with these plasmids on day 0 and day 14, OVA specific IgG titer, OVA specific serum IgG1 titer and OVA specific serum IgG2c titer were measured to monitor the ratio of OVA specific serum IgG2c to OVA specific serum IgG1. Data represents two independent experiments. * indicates p<0.05, and ** indicates p<0.005 (Mann-Whitney U test).

FIG. 2B The effect of antigen targeting to an exosome on immunogenicity of a DNA vaccine. C57BL/6J mice (n=6) were immunized by introducing pOVA, pCD63, or pCD63-OVA by intramuscular electroporation (50 μg/mouse). On day 21 after immunization with these plasmids on day 0 and day 14, the ratio of $CD8^+$ T cells recognized by an $OVA_{257-264}$ specific tetramer (B), and IFN-γ level induced in splenocytes by OVA, $OVA_{257-264}$, $OVA_{323-339}$, or a medium were monitored. Data represents two independent experiments. The error bar represents the SD. * indicates p<0.05 and ** indicates p<0.005 (Mann-Whitney U test).

Figure 1B:
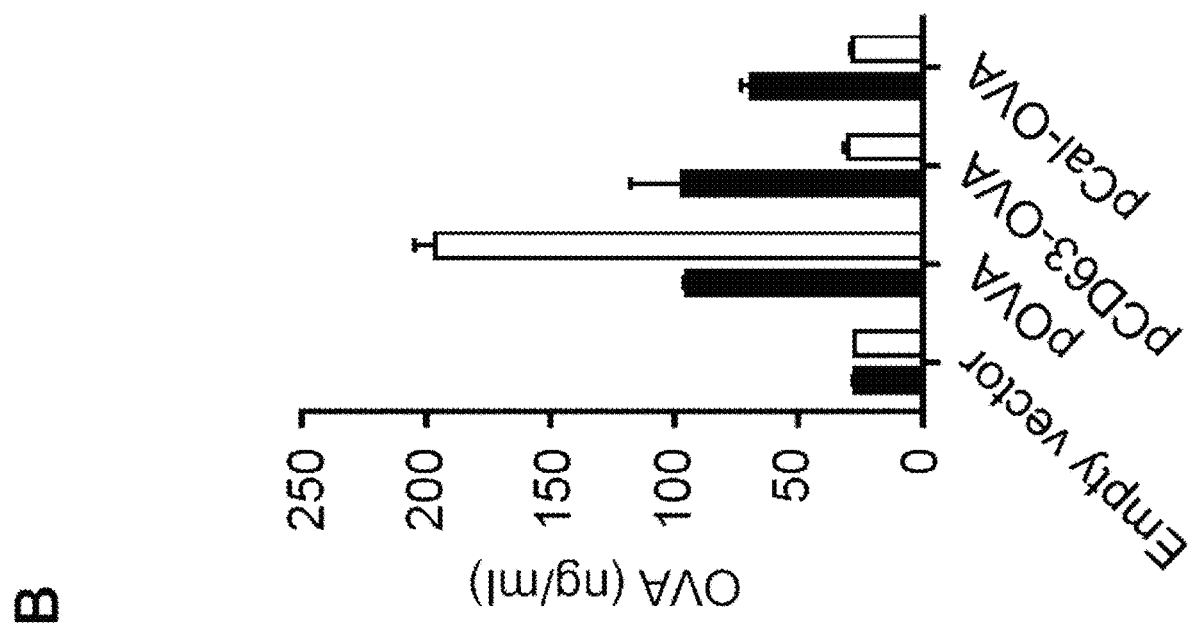
FIG. 1B Evaluation of antigen expressing exosomes as a CTL inducing immunogen. (A, B) An empty vector, pOVA, pCD63, pCD63-OVA, or pCal-OVA was transiently transfected into 293-F cells and 293T cells. After 48 hours from transfection, the supernatant was separated from the cells, and the exosome fraction was purified. (A) The cell, supernatant, and exosome fractions were analyzed by immunoblotting. (B) ELISA was used on the cells and supernatant to analyze the OVA protein concentration. The error bar represents the SD. The black bars indicate cells, and white bars indicate supernatant.

were immunized by introducing pCal-OVA or pCD63-OVA by intramuscular electroporation (50 µg/mouse). On day 21 after immunization with these plasmids on day 0 and day 14, OVA specific IgG titer, OVA specific serum IgG1 titer, and OVA specific serum IgG2c titer were measured to monitor the ratio of OVA specific serum IgG2c to OVA specific serum IgG1. The leftmost graph shows the logarithmic OVA specific IgG titer (antibody OVA titer) for total IgG. Second and third graphs from the left show results of observing the same numerical value for IgG1 and IgG2c. The rightmost graph shows the ratio of OVA specific serum IgG2c to OVA specific serum IgG1 (IgG2c/IgG1). * indicates $p<0.05$ (Mann-Whitney U test). NS indicates that a statistically significant difference was not found.

FIG. 2E The effect of antigen targeting to an exosome on immunogenicity of a DNA vaccine. C57BL/6J mice (n=10) were immunized by introducing pCal-OVA or pCD63-OVA by intramuscular electroporation (50 µg/mouse). On day 21 after immunization with these plasmids on day 0 and day 14, the ratio of CD8$^+$ T cells recognized by an OVA$_{257-264}$ specific tetramer (F), and IFN-γ level induced in spenocytes by OVA, OVA$_{257-264}$, OVA$_{323-339}$, or a medium (E) were monitored. Data represents three independent experiments. The error bar represents the SD. * indicates $p<0.05$ and ** indicates $p<0.005$ (Mann-Whitney U test). For the bar labels, a, b, c, and d indicate medium, OVA$_{257-264}$, OVA$_{323-339}$, and OVA, respectively.

FIG. 2F The effect of antigen targeting to an exosome on immunogenicity of a DNA vaccine. C57BL/6J mice (n=10) were immunized by introducing pOVA, pCal-OVA, or pCD63-OVA by intramuscular electroporation (50 µg/mouse). On day 21 after immunization with these plasmids on day 0 and day 14, the ratio of CD8$^+$ T cells recognized by an OVA$_{257-264}$ specific tetramer (F), and IFN-γ level induced in splenocytes by OVA, OVA$_{257-264}$, OVA$_{323-339}$, or a medium (E) were monitored. Data represents three independent experiments. * indicates $p<0.05$ (Mann-Whitney U test) (the p value of pCD63-OVA with respect to pCal-OVA was 0.023).

Figure 3A:
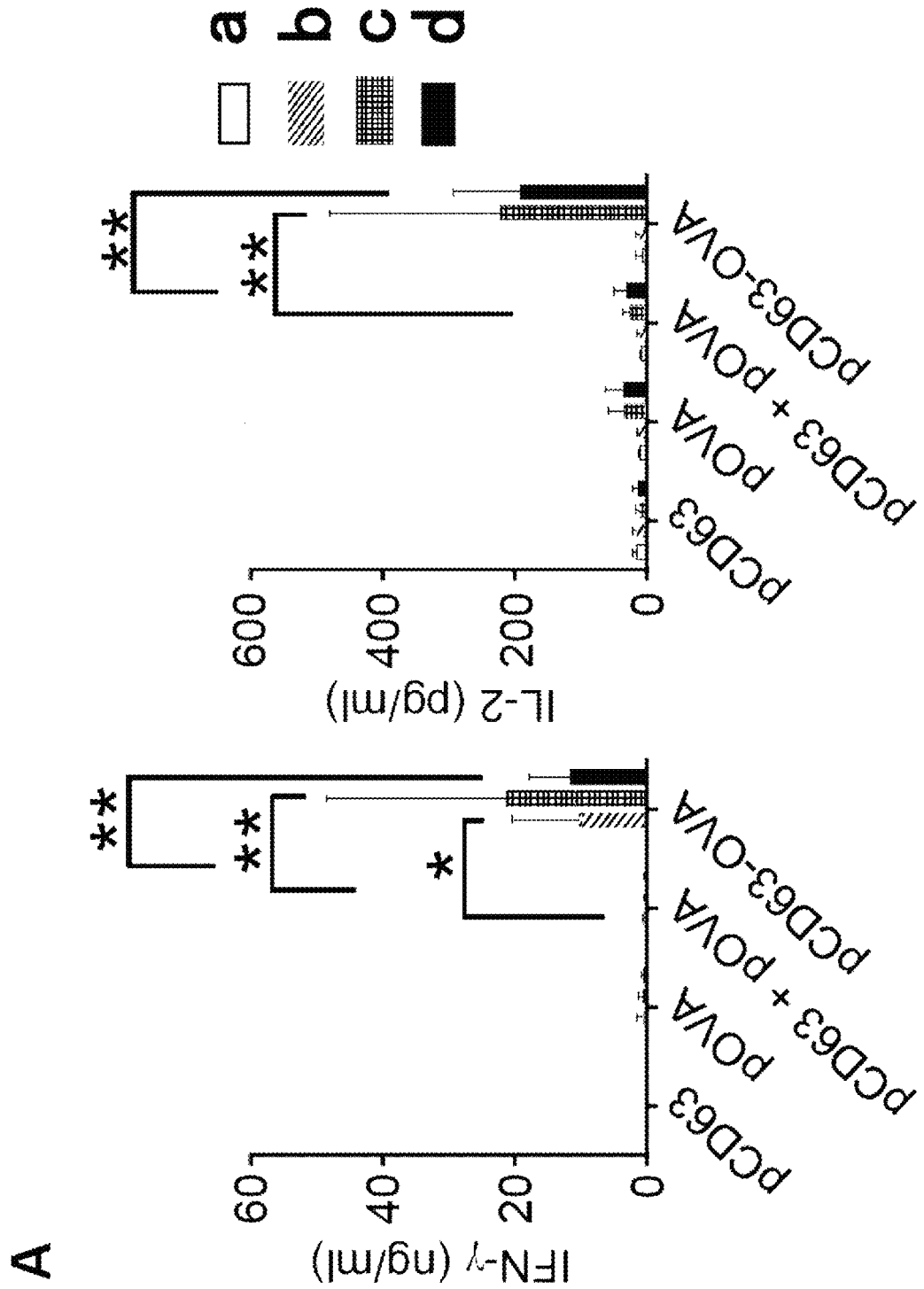

FIG. 3A Evaluation of CD63 expression plasmid as a gene adjuvant for a co-administered DNA vaccine. (A, B) C57BL/6J mice (n=5) were immunized by introducing pOVA, pCD63, pOVA+pCD63, or pCD63-OVA by intramuscular electroporation (50 µg/mouse). On day 21 after immunization with these plasmids on day 0 and day 14, IFN-γ or IL-2 level induced in splenocytes by OVA, OVA$_{257-264}$, OVA$_{323-339}$, or a medium (A) and the ratio of CD8$^+$ T cells recognized by an OVA$_{257-264}$ specific tetramer (B) were monitored. Data represents two independent experiments. The error bar represents the SD. * indicates $p<0.05$ and ** indicates $p<0.005$ (Mann-Whitney U test). For the bar labels, a, b, c, and d indicate medium, OVA$_{257-264}$, OVA$_{323-339}$, and OVA, respectively.

FIG. 3B Evaluation of CD63 expression plasmid as a gene adjuvant for a co-administered DNA vaccine. (A, B) C57BL/6J mice (n=5) were immunized by introducing pOVA, pCD63, pOVA+pCD63, or pCD63-OVA by intramuscular electroporation (50 µg/mouse). On day 21 after immunization with these plasmids on day 0 and day 14, IFN-γ or IL-2 level induced in splenocytes by OVA, OVA$_{257-264}$, OVA$_{323-339}$, or a medium (A) and the ratio of CD8$^+$ T cells recognized by an OVA$_{257-264}$ specific tetramer (B) were monitored. Data represents two independent experiments. The error bar represents the SD. * indicates $p<0.05$ and ** indicates $p<0.005$ (Mann-Whitney U test).

Figure 4A:
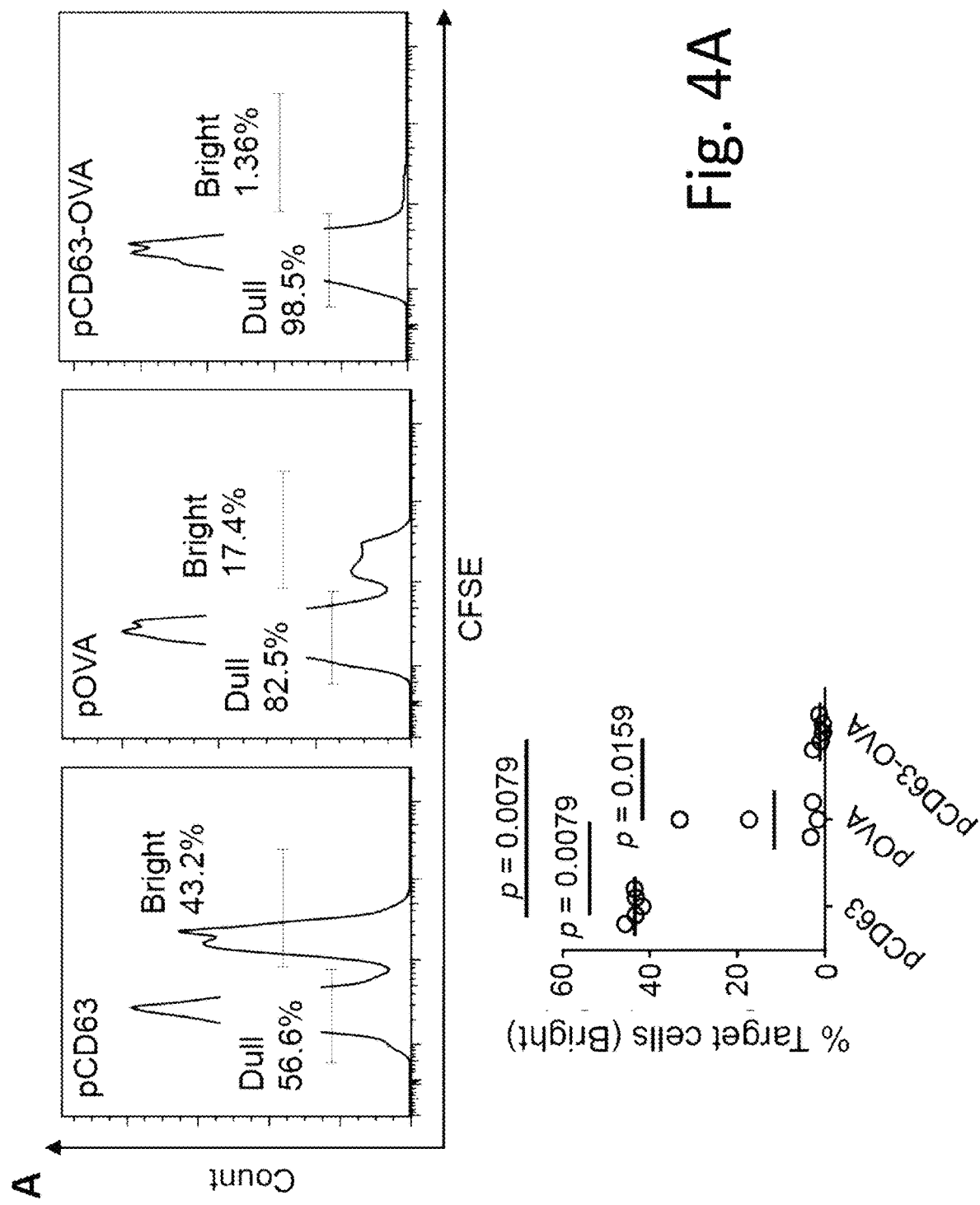

FIG. 4A The effect of antigen targeting to an exosome on prophylactic or therapeutic tumor vaccine. (A) An in vivo CTL assay was conducted after 7 days from DNA vaccine preparation using pOVA (n=5), pCD63-OVA (n=5), or pCD63 (n=5). Data represents two independent experiments. The horizontal axis of the top diagram depicts the logarithmic fluorescence intensity of CFSE, and the vertical axis indicates the cell count corresponding to the fluorescence intensity. In the bottom diagram, an experiment was conducted, where cells were stained with CFSE and cells with strong fluorescence intensity were killed by cytotoxic T cells to evaluate how much cytotoxic T cells are induced in mice by the ratio of killed cells. The bottom diagram shows the ratio of surviving cells with strong fluorescence intensity. The error bar represents the SD.

FIG. 4B (B) C57BL/6J mice (n=10) were immunized by introducing pOVA, pCD63, or pCD63-OVA by intramuscular electroporation (50 µg/mouse). 7 days after the last immunization, mice were inoculated with 1×10$^6$ E.G7 cells. Tumor growth was monitored thereafter for 28 days. Data represents two independent experiments. The error bar represents SEM.

Figure 4C:
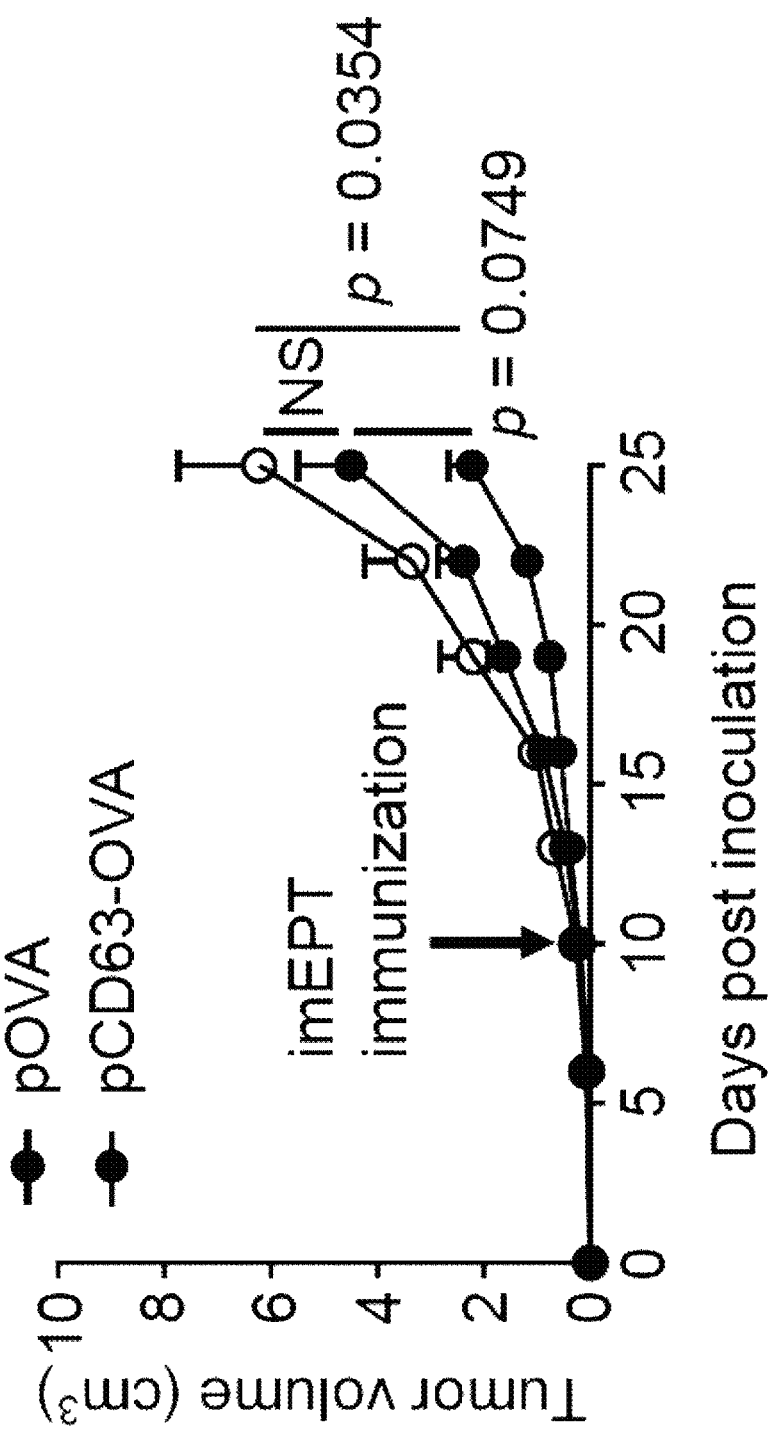

FIG. 4C (C) 10 days before the immunization, mice were inoculated with 1×10$^6$ E.G7 cells. 10 mice for each group were immunized with 50 µg of pOVA-FL antigen, pCD63-OVA-FL antigen, or an empty vector. Tumor growth was monitored thereafter for 25 days. Data represents three independent experiments. The error bar represents SEM.

FIG. 4D (D) The ratio of CD8$^+$ T cells recognized by T cells recognized by an OVA$_{257-264}$ specific tetramer was monitored on day 25 after inoculation of E.G7 cells. Data represents two independent experiments. The error bar represents the SD.

FIG. 5 CD63-OVA-EGFP (EGFP indicates enhanced GFP) in the exosome fraction. Either a pCD63-OVA-EGFP vector or an empty vector was transiently transfected into 293F cells. The supernatant of each culture was collected after 48 days from transfection. The gating strategy for determining an exosome fraction was based on SSC to FCS by using PBS, 100 nm beads, and 200 nm beads. The results of analysis by flow cytometry are shown. The top row shows cases of using, from the left, PBS, 100 nm beads, and 200 nm beads. The left side of the bottom row shows analysis of supernatant. The right side shows the exosome fraction after gating.

FIG. 6A Evaluation of immunological benefit of other exosome markers fused with OVA for DNA vaccine preparation. (A, B) An empty vector, pCD9-OVA-FL antigen, or CD81-OVA-FL antigen was transiently transfected into 293-F cells and 293T cells. Exosomes were purified from the cell supernatant after 48 days from transfection. (A) Cells and exosomes were analyzed by immunoblotting. (B) The OVA protein concentrations of the cells and supernatant were analyzed by ELISA. The labels a and b indicate the cell and exosome fractions, respectively.

FIG. 6B Evaluation of immunological benefit of other exosome markers fused with OVA for DNA vaccine preparation. (A, B) An empty vector, pCD9-OVA-FL antigen, or CD81-OVA-FL antigen was transiently transfected into 293-F cells and 293T cells. Exosomes were purified from the cell supernatant after 48 days from transfection. (A) Cells and exosomes were analyzed by immunoblotting. (B) The OVA protein concentrations of the cells and supernatant were analyzed by ELISA. The black bars indicate cells and the white bars indicate supernatant.

FIG. 6C C57BL/6J mice (n=6) were immunized by introducing pOVA, pCD9-OVA, pCD63-OVA, or CD81-OVA by intramuscular electroporation (50 µg/mouse). The ratio of OVA specific serum IgG2c to OVA specific serum IgG1 (C), the IFN-γ level (ng/ml) induced in splenocytes by OVA, $OVA_{257-264}$, $OVA_{323-339}$, or a medium (D), and the ratio of $CD8^+$ T cells recognized by an $OVA_{257-264}$ specific tetramer were monitored. * indicates p<0.05 and ** indicates p<0.005 (Mann-Whitney U test).

FIG. 6D C57BL/6J mice (n=6) were immunized by introducing pOVA, pCD9-OVA, pCD63-OVA, or CD81-OVA by intramuscular electroporation (50 μg/mouse). The ratio of OVA specific serum IgG2c to OVA specific serum IgG1 (C), the IFN-γ level (ng/ml) induced in splenocytes by OVA, $OVA_{257-264}$, $OVA_{323-339}$, or a medium (D), and the ratio of $CD8^+$ T cells recognized by an $OVA_{257-264}$ specific tetramer were monitored. * indicates p<0.05 and * * indicates p<0.005 (Mann-Whitney U test). The bar labels a, b, c, and d indicate the medium, $OVA_{257-264}$, $OVA_{323-339}$, and OVA, respectively.

Figure 6E:
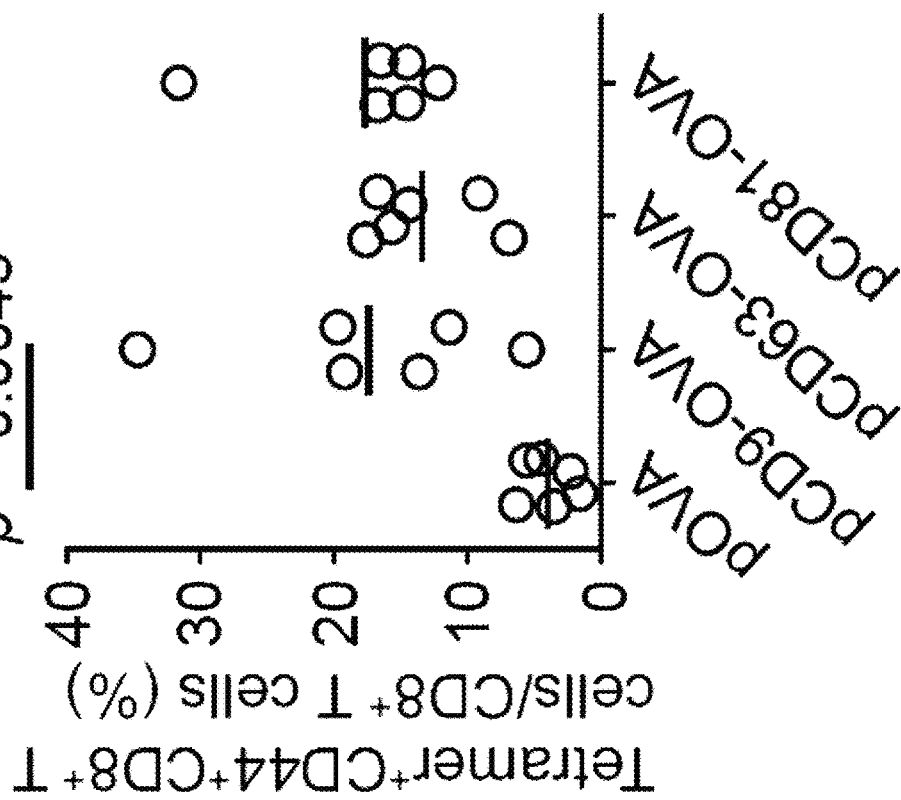

FIG. 6E C57BL/6J mice (n=6) were immunized by introducing pOVA, pCD9-OVA, pCD63-OVA, or CD81-OVA by intramuscular electroporation (50 μg/mouse). The ratio of OVA specific serum IgG2c to OVA specific serum IgG1 (C), the IFN-γ level (ng/ml) induced in splenocytes by OVA, $OVA_{257-264}$, $OVA_{323-339}$, or a medium (D), and the ratio of $CD8^+$ T cells recognized by an $OVA_{257-264}$ specific tetramer were monitored. * indicates p<0.05 and ** indicates p<0.005 (Mann-Whitney U test).

DESCRIPTION OF EMBODIMENTS

The present invention is explained hereinafter while describing the best mode of the invention. Throughout the specification, a singular expression should be entire understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

The definitions of the terms and/or the basic technical content that are particularly used herein are explained hereinafter as appropriate.

As used herein, "vaccine" refers to a substance which comprises or encodes an antigen that does not induce a disease, but provides active immunity against a substance comprising an antigen. As used herein, "DNA vaccine" refers to a nucleic acid encoding a vaccine antigen. Such a common name is used because DNA (especially plasmid DNA) is mainly used. It is understood that an embodiment using a nucleic acid includes an embodiment of a vaccine incorporating a viral vector or the like which is delivered into the body, in which case a vaccine can also be provided in a nucleic acid form other than DNA. In such a case, the vaccine is also called a "nucleic acid vaccine". DNA vaccines are generally in a form of a plasmid DNA. Meanwhile, if a DNA vaccine is subcutaneously administered in a form of a plasmid DNA, the plasmid DNA is incorporated into a subcutaneous cell and produces an antigen protein of interest in the cell.

DNA vaccine inoculation can be a prophylactic and/or therapeutic method for a human disease, which can be applied to not only infectious diseases but also on non-transmittable diseases. The clinical benefit of a DNA vaccine is the low cost, stability and high level of producibility, and the ease of modification of the antigen sequence thereof to be effective against a highly mutated pathogen. In the field of veterinary medicine, DNA vaccines are already approved for West Niles viruses in horses, infectious hematopoietic necrosis viruses in salmons, and melanoma in dogs. The results of early stage clinical trials in humans indicate that a DNA vaccine is safe and well tolerated, but the immunogenicity of a DNA vaccine is much lower than expected based on the results of animal experiments. For example, this has not been able to be solved by a change in use of a promotor or codon in an antigen sequence, insertion of a genetic adjuvant, addition of a boost vaccination, mixing of a vaccine with an external adjuvant, administration of a vaccine through improvement in the pathway or device, or the like.

"Plasmid DNA" is used in the meaning that is commonly used in the art. "Plasmid DNA" refers to a DNA molecule that is present outside the nucleus of bacteria such as E. coli or yeast and is inherited by a daughter cell through cell division. Since a plasmid DNA generally has a cyclic double stranded structure and replicates independently from a DNA of a chromosome, a plasmid DNA can be used as a vector in order to introduce a gene. Plasmids include those that play various roles, such as those with a gene of a protein exhibiting resistance to a drug and those that transform other bacteria by inducing cell conjugation called F plasmid. Plasmids can be appropriately selected and utilized in accordance with the objective in the present invention.

As used herein, "nucleic acid construct" refers to a construct comprising a nucleic acid. Nucleic acid constructs include those that are simple nucleic acid fragments as well as those in a form of a plasmid DNA, those with a function of a DNA vaccine, and the like.

As used herein, "antigen" (also referred to as Ag) refers to any substrate that can be specifically bound by an antibody molecule. As used herein, "immunogen" refers to an antigen that can initiate lymphocyte activation which leads to an antigen specific immune response. As used herein, "epitope" or "antigen determinant" refers to a site in an antigen molecule to which an antibody or a lymphocyte receptor binds. A method of determining an epitope is well known in the art. Such an epitope can be determined by those skilled in t a well-known and conventional technique when a primary sequence of an amino acid or a nucleic acid is provided. It is understood that not only the specific antibodies in the Examples, but also antibodies having different sequences can be similarly used as the antibody of the invention, as long as the epitope is the same.

As used herein, "vaccine antigen" refers to an antigen with an ability to induce a response from the immune system when administered to a human or an animal. Such a response from the immune system can induce production of antibodies or activation of a certain type of cells (particularly antigen presenting cells (e.g., dendritic cells), T lymphocytes, or B lymphocytes). In the present invention, examples thereof include, but are not limited to, cancer antigens for therapy targeting cancer. For example, an ovalbumin can be used as a model vaccine antigen. Anticancer activity can be tested with a test on a model animal. Such a test can be conducted by referring to Onishi M. et al., J Immunol 194:2673-2682, or the like. CTL activity or the like can be tested by referring to Kobiyama K. et al., Proc Natl Acad Sci USA 111:3086-3091. As used herein, "vaccine antigen" may be called a "vaccine antigen protein" when referring to only proteins.

"Exosome" is used in the meaning that is commonly used in the art. An exosome is a membrane vesicle that is secreted in a cell with a diameter of generally 30 nm to 150 nm and preferably about 30 to 100 nm. An exosome is a multiprotein complex which degrades various RNAs and is secreted from all types of cells through fusion with a plasma membrane of a multivesicular body. Exosomes are present in various bodily fluids such as the plasma, breast milk, semen, saliva, and urine. Interestingly, many of DNA, RNA, miRNA, protein, and lipids are contained inside an exosome. These vesicles were shown to mediate cell-cell communication and to be closely associated with immunomodulation (Poutsiaka, D. D., D. D. Taylor, E. M. Levy, and P. H. Black. 1985. J Immunol 134:145-150.) Both MHC class I and II and APC expressing a costimulation molecule that stimulates $CD4^+$ and $CD8^+$ T cells secret exosomes (Robbins, P. D., and A. E. Morelli. 2014. Nat Rev Immunol 14:195-208, Bobrie, A., M. Colombo, G. Raposo, and C. Thery. 2011. Traffic 12:1659-1668). In addition, mature dendritic cell (DC) derived exosomes can activate immature dendritic cells the and improve antigen presenting capability thereof (Montecalvo, A., et al., 2012. Blood 119:756-766.) An antigen containing exosome can also be used as a vaccine for cancer therapy (Raposo, G., et al., 1996. J Exp Med 183:1161-1172.) However, use of an exosome as a material for DNA vaccines is not suggested.

Tetraspanin family proteins are known as a surface marker of an exosome. While lipids are the main component exosomes comprise various proteins, lipids, of exosomes, and RNA (including miRNA). They are understood to induce a functional or physiological change by being transported to another cell. As used herein, a naturally-occurring exosome expressing the DNA vaccine of the invention is typically used, but an exosome may be further modified. It is understood that such a modification can be any modification, as long as the exosome can be used as a DNA vaccine. It is suggested that exosomes play a role in mediation of an adaptive immune response to infection pathogens or tumor, tissue repair, neurotransmission, transport of pathogenic proteins, and the like. Detailed descriptions can be found by referring to for example Trends Mol Med. 2015 Jul. 28. pii: S1471-49 14(15)00137-9, whose content is incorporated herein by reference.

As used herein, "exosome marker protein" refers to any protein contained in an exosome. Examples of such a protein include tetraspanin family proteins (e.g., CD9, CD63, CD81, and the like), Alix, Tsg101, Hsp70, other heat shock proteins, and the like (see for example Trends Mol Med. 2015 Jul. 28. pii: S1471-1491 4(15)00137-9. (Trends Mol Med. Volume 21, Issue 9, September 2015, Pages 533-542); J. Cell Biol. Vol. 200 No. 4, 373-383, and the like).

As used herein, "tetraspanin family" is a membrane protein family with a structure that penetrates the cell membrane four times. In humans, at least 33 types of members such as CD9, CD63, CD81, CD82, and CD151 are known. In summary, the function of tetraspanin is formation of a complex by binding to another membrane protein. For this reason, this is also called a molecular facilitator or molecular organizer. In the present invention, the same effect as CD63 is also confirmed in the Examples for tetraspanins CD9 and CD81. Thus, it is understood that any tetraspanin family protein can be advantageously used in a DNA vaccine.

CD63 is a member of the tetraspanin family. CD63 is also called LAMP-3, ME491, MLA1, OMA81H, or TSPAN30. The nucleic acid sequence and amino acid sequence of human CD63 are disclosed in NCBI accession numbers NM_001040034 (SEQ ID NO: 1) and NP_001244318 (SEQ ID NO: 2), respectively, and the nucleic acid sequence and the amino acid sequence of mice are disclosed in NM_001042580 (SEQ ID NO: 3) and NP_001036045 (SEQ ID NO: 4), respectively, which are also incorporated herein by reference. CD63 can be identified by the accession number OMIM: 155740 HomoloGene: 375267. When used for the purpose herein, it is understood that "CD63" refers to not only proteins with the amino acid sequence set forth in a specific sequence number or accession number (or nucleic acids encoding them), but also functionally active derivatives thereof, functionally active fragments thereof, homologs thereof, and mutants encoded by a nucleic acid that hybridizes with a nucleic acid encoding the protein under conditions with high or low stringency.

CD9 is a member of the tetraspanin family. CD9 is also called BTCC-1, DRAP-27, MIC3, MRP-1, TSPAN-29, or TSPAN29. The nucleic acid sequence and amino acid sequence of human CD9 are disclosed in NCBI accession numbers NM_001769 (SEQ ID NO: 5) and NP_001760 (SEQ ID NO: 6), respectively, and the nucleic acid sequence and the amino acid sequence of mice are disclosed in NM_007657 (SEQ ID NO: 7) and NP_031683 (SEQ ID NO: 8), respectively, which are also incorporated herein by reference. CD9 can be identified by the accession number OMIM: 143030 MGI: 88348 HomoloGene: 20420 GeneCards: CD9 Gene. When used for the purpose herein, it is understood that "CD9" refers to not only proteins with the amino acid sequence set forth in a specific sequence number or accession number (or nucleic acids encoding them), but also functionally active derivatives thereof, functionally active fragments thereof, homologs thereof, and mutants encoded by a nucleic acid that hybridizes with a nucleic acid encoding the protein under conditions with high or low stringency.

CD81 is a member of the tetraspanin family. CD81 is also called CVID6, S5.7, TAPA1, or TSPAN28. The nucleic acid sequence and amino acid sequence of human CD81 are disclosed in NCBI accession numbers NM_001297649 (SEQ ID NO: 9) and NP_001284578 (SEQ ID NO: 10), respectively, and the nucleic acid sequence and the amino acid sequence of mice are disclosed in NM_133655 (SEQ ID NO: 11) and NP_598416 (SEQ ID NO: 12), respectively, which are also incorporated herein by reference. CD81 can be identified by the accession number OMIM: 186845 MGI: 1096398 HomoloGene: 20915 ChEMBL: 1075180 GeneCards: CD81 Gene. When used for the purpose herein, it is understood that "CD81" refers to not only proteins with the amino acid sequence set forth in a specific sequence number or accession number (or nucleic acids encoding them), but also functionally active derivatives thereof, functionally active fragments thereof, homologs thereof, and mutants encoded by a nucleic acid that hybridizes with a nucleic acid encoding the protein under conditions with high or low stringency.

The same applies to all other proteins mentioned in the present invention. Therefore, the established name of a protein or nucleic acid not only refers to a protein or nucleic acid disclosed herein, explicitly but also functionally active derivatives, functionally active fragments thereof, homologs thereof, and mutants encoded by a nucleic acid that hybridizes with a nucleic acid encoding the protein under conditions with high or low stringency, preferably the aforementioned conditions. As used herein, "derivative", "analog of a constituent protein", or "mutant" preferably includes, without intending to be limiting, molecules comprising a substantially homologous region in a constituent protein. In various embodiments, such a molecule is at least 30%, 40%, 50%, 60%, 70%, 80%, 90%, 95%, or 99% identical compared to an amino acid sequence of the same size or a sequence aligned by a computer homology program known in the art, or a nucleic acid encoding such a molecule can hybridize with a sequence encoding a constituent protein under stringent conditions, moderately stringent conditions, or non-stringent conditions. This is a result of modifying a naturally-occurring protein by an amino acid substitution, deletion, and addition, and refers to a protein whose derivative still exhibits, although not necessarily to the same degree, the biological function of the naturally-occurring protein. For example, the biological function of such a protein can be found by a suitable and available in vitro assay that is described herein or known in the art.

As used herein, "functionally active" refers to a polypeptide, a fragment, or a derivative having a structural function, regulating function, or biochemical function of a protein such as biological activity in accordance with the embodiment associated with the polypeptide, fragment or derivative of the invention. In the present invention, a fragment of an exosome marker protein or a protein belonging to the tetraspanin family is a polypeptide comprising any region of the exosome marker protein or the protein belonging to the tetraspanin family, which does not need to have the biological function of naturally-occurring exosome marker protein or a protein belonging to the tetraspanin family as long as the objective of the present invention can be attained.

A typical nucleotide sequence of CD63 can be:
(a) a polynucleotide having the base sequence set forth in SEQ ID NO: 1 or 3 or a fragment sequence thereof;
(b) a polynucleotide encoding a polypeptide consisting of the amino acid sequence set forth in SEQ ID NO: 2 or 4 or a fragment thereof;
(c) a polynucleotide encoding a variant polypeptide or a fragment thereof having one or more amino acids with a mutation selected from the group consisting of substitution, addition, and deletion in the amino acid sequence set forth in SEQ ID NO: 2 or 4, wherein the variant polypeptide has biological activity;
(d) a polynucleotide, which is a splice mutant or allelic mutant of the base sequence set forth in SEQ ID NO: 1 or 3, or a fragment thereof;
(e) a polynucleotide encoding a species homolog of a polypeptide consisting of the amino acid sequence set forth in SEQ ID NO: 2 or 4 or a fragment thereof;
(f) a polynucleotide, which hybridizes with one of the polynucleotides of (a) to (e) under stringent conditions and encodes a polypeptide with biological activity; or
(g) a polynucleotide, which consists of a base sequence having at least 70% identity to one of the polynucleotides of (a) to (e) or a complementary sequence thereof and encodes a polypeptide having biological activity.

In this regard, biological activity typically refers to the activity of CD63.

The amino acid sequence of CD63 can be:
(a) a polypeptide consisting of the amino acid sequence set forth in SEQ ID NO: 2 or 4 or a fragment thereof;
(b) a polypeptide having one or more amino acids with a mutation selected from the group consisting of substitution, addition, and deletion in the amino acid sequence set forth in SEQ ID NO: 2 or 4, and having biological activity;
(c) a polypeptide encoded by a splice mutant or allelic mutant of the base sequence set forth in SEQ ID NO: 1 or 3;
(d) a polypeptide, which is a species homolog of the amino acid sequence set forth in SEQ ID NO: 2 or 4; or
(e) a polypeptide having an amino acid sequence with at least 70% identity to one of the polypeptides of (a) to (d) and having biological activity.

In this regard, biological activity typically refers to the activity of CD63.

A typical nucleotide sequence of CD9 can be:
(a) a polynucleotide having the base sequence set forth in SEQ ID NO: 5 or 7 or a fragment sequence thereof;
(b) a polynucleotide encoding a polypeptide consisting of the amino acid sequence set forth in SEQ ID NO: 6 or 8 or a fragment thereof;
(c) a polynucleotide encoding a variant polypeptide or a fragment thereof having one or more amino acids with a mutation selected from the group consisting of substitution, addition, and deletion in the amino acid sequence set forth in SEQ ID NO: 6 or 8, wherein the variant polypeptide has biological activity;
(d) a polynucleotide, which is a splice mutant or allelic mutant of the base sequence set forth in SEQ ID NO: 5 or 7, or a fragment thereof;
(e) a polynucleotide encoding a species homolog of a polypeptide consisting of the amino acid sequence set forth in SEQ ID NO: 6 or 8 or a fragment thereof;
(f) a polynucleotide, which hybridizes with one of the polynucleotides of (a) to (e) under stringent conditions and encodes a polypeptide with biological activity; or
(g) a polynucleotide, which consists of a base sequence having at least 70% identity to one of the polynucleotides of (a) to (e) or a complementary sequence thereof and encodes a polypeptide having biological activity.

In this regard, biological activity typically refers to the activity of CD9.

The amino acid sequence of CD9 can be:
(a) a polypeptide consisting of the amino acid sequence set forth in SEQ ID NO: 6 or 8 or a fragment thereof;
(b) a polypeptide having one or more amino acids with a mutation selected from the group consisting of substitution, addition, and deletion in the amino acid sequence set forth in SEQ ID NO: 6 or 8, and having biological activity;
(c) a polypeptide encoded by a splice mutant or allelic mutant of the base sequence set forth in SEQ ID NO: 5 or 7;
(d) a polypeptide, which is a species homolog of the amino acid sequence set forth in SEQ ID NO: 6 or 8; or
(e) a polypeptide having an amino acid sequence with at least 70% identity to one of the polypeptides of (a) to (d) and having biological activity.

In this regard, biological activity typically refers to the activity of CD9.

A typical nucleotide sequence of CD81 can be:
(a) a polynucleotide having the base sequence set forth in SEQ ID NO: 9 or 11 or a fragment sequence thereof;
(b) a polynucleotide encoding a polypeptide consisting of the amino acid sequence set forth in SEQ ID NO: 10 or 12 or a fragment thereof;
(c) a polynucleotide encoding a variant polypeptide or a fragment thereof having one or more amino acids with a mutation selected from the group consisting of substitution, addition, and deletion in the amino acid sequence set forth in SEQ ID NO: 10 or 12, wherein the variant polypeptide has biological activity;

(d) a polynucleotide, which is a splice mutant or allelic mutant of the base sequence set forth in SEQ ID NO: 9 or 11, or a fragment thereof;
(e) a polynucleotide encoding a species homolog of a polypeptide consisting of the amino acid sequence set forth in SEQ ID NO: 10 or 12 or a fragment thereof;
(f) a polynucleotide, which hybridizes with one of the polynucleotides of (a) to (e) under stringent conditions and encodes a polypeptide with biological activity; or
(g) a polynucleotide, which consists of a base sequence having at least 70% identity to one of the polynucleotides of (a) to (e) or a complementary sequence thereof and encodes a polypeptide having biological activity.

In this regard, biological activity typically refers to the activity of CD81.

The amino acid sequence of CD81 can be:
(a) a polypeptide consisting of the amino acid sequence set forth in SEQ ID NO: 10 or 12 or a fragment thereof;
(b) a polypeptide having one or more amino acids with a mutation selected from the group consisting of substitution, addition, and deletion in the amino acid sequence set forth in SEQ ID NO: 10 or 12, and having biological activity;
(c) a polypeptide encoded by a splice mutant or allelic mutant of the base sequence set forth in SEQ ID NO: 9 or 11;
(d) a polypeptide, which is a species homolog of the amino acid sequence set forth in SEQ ID NO: 10 or 12; or
(e) a polypeptide having an amino acid sequence with at least 70% identity to one of the polypeptides of (a) to (d) and having biological activity.

In this regard, biological activity typically refers to the activity of CD81.

Each of them can be identified using an approach that is known in the art. Examples of references that can be referred for such an approach include references that are mentioned elsewhere herein and the like.

As used herein, "protein", "polypeptide", "oligopeptide" and "peptide" are used in the same meaning, referring to a polymer of amino acids of any length. Such a polymer may be linear, branched, or cyclic. Amino acids may be naturally-occurring, non-naturally occurring, or altered amino acids. These terms may also encompass those assembled into a complex of multiple polypeptide chains. These term also encompass naturally or artificially-altered amino acid polymers. Examples of such an alteration include disulfide bond formation, glycosylation, lipidation, acetylation, phosphorylation, and any other manipulation or alteration (e.g., conjugation with a label component). This definition also encompasses, for example, polypeptides comprising one or more analogs of amino acids (e.g., including non-naturally-occurring amino acids or the like), peptide-like compounds (e.g., peptoid), and other alterations known in the art. As use herein, "amino acid" may be naturally occurring or non-naturally occurring, as long as the objective of the present invention is met.

As used herein, "polynucleotide", "oligonucleotide", and "nucleic acid" are used in the same meaning, referring to a polymer of nucleotides of any length. These terms also encompass "oligonucleotide derivative" and "polynucleotide derivative". The "oligonucleotide derivative" and "polynucleotide derivative" are interchangeably used and refer to an oligonucleotide or polynucleotide which comprises a derivative a nucleotide of or an oligonucleotide or polynucleotide with a bond between nucleotides that is different from normal bonds. It is understood that these derivatives or the like can be any derivative or the like, as long as they can be used as a DNA vaccine. Specific examples of such oligonucleotides include: 2'-O-methyl-ribonucleotide; oligonucleotide derivatives with a phosphodiester bond in an oligonucleotide converted into phosphorothioate bond; oligonucleotide derivatives with a phosphodiester bond in an oligonucleotide converted into an N3'-P5' phosphoramidate bond; oligonucleotide derivatives with a ribose and a phosphodiester bond in an oligonucleotide converted into a peptide nucleic acid bond; oligonucleotide derivatives with a uracil in an oligonucleotide substituted with a C-5 propynyl uracil; oligonucleotide derivatives with uracil in an oligonucleotide substituted with a C-5 thiazole uracil; oligonucleotide derivatives with a cytosine in an oligonucleotide substituted with a C-5 propynyl cytosine; oligonucleotide derivatives with a cytosine in an oligonucleotide substituted with a phenoxazine-modified cytosine; oligonucleotide derivatives with a ribose in DNA substituted with a 2'-O-propylribose; oligonucleotide derivatives with a ribose in an oligonucleotide substituted with a 2'-methoxyethoxy ribose, and the like. Unless noted otherwise, specific nucleic acid sequences are intended to encompass sequences that are explicitly set forth, as well as their conservatively altered variants (e.g., degenerate codon substitutes) and complementary sequences. Specifically, a degenerate codon substitute can be achieved by making a sequence in which the third position of one or more selected (or all) codons is substituted with mixed base and/or deoxyinosine residue (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). As used herein, "nucleic acid" is also interchangeably used with gene, CDNA, mRNA, oligonucleotide, and polynucleotide. As used herein, "nucleotide" may be naturally occurring or non-naturally-occurring.

As used herein, "gene" refers to an agent that defines a genetic trait. A "gene" may refer to a "polynucleotide", "oligonucleotide", or "nucleic acid".

As used herein, "homology" of genes refers to identity of two or more genetic sequences with respect to one another, and having "homology" generally refers to having a high degree of identity or similarity. Therefore, the identity or similarity of sequences is higher when homology of two genes is high. Whether two types of genes have homology can be found by direction comparison of sequences or by a hybridization method under stringent conditions for nucleic acids. When two genetic sequences are directly compared, the genes are homologous when DNA sequences are typically at least 50% identical, preferably at least 70% identical, and more preferably at least 80%, 90%, 95%, 96%, 97%, 98%, or 99% identical between the genetic sequences. Thus, as used herein, "homolog" or "homologous gene product" refers to a protein in another species, preferably mammal, exerting the same biological function as a protein constituent of a complex which will be further described herein. Such a homolog is also called "ortholog gene product". It is understood that such a homolog, homologous gene product, ortholog gene product or the like can also be used, as long as they are in alignment with the objective of the invention.

Amino acids may be mentioned herein by either their commonly known three letter symbols or their one character symbols recommended by the IUPAC-IUB Biochemical Nomenclature Commission. Similarly, nucleotides may be mentioned by their commonly recognized one character codes. Comparison of similarity, identity and homology of an amino acid sequence and a base sequence is calculated herein by using a default parameter using a sequence analysis tool, BLAST. For example, identity can be searched using BLAST 2.2.28 (published on Apr. 2, 2013) of the NCBI. Herein, values for identity generally refer to a value obtained when aligned under the default conditions using BLAST. However, when a higher value is obtained by changing a parameter, the highest value is considered the value of identity. When identity is evaluated in a plurality of regions, the highest value thereamong is considered the value of identity. Similarity is a value calculated by taking into consideration a similar amino acid in addition to identity.

In one embodiment of the present invention, "several" may be, for example, 10, 8, 6, 5, 4, 3 or 2, or a value less than any one of the values. It is known that a polypeptide with one or several amino acid residue deletions, additions, insertions, or substitutions by other amino acids maintains its biological activity (Mark et al., Proc Natl Acad Sci USA. 1984 September; 81(18):5662-5666. , Zoller et al., Nucleic Acids Res. 1982 Oct, 25; 10(20):6487-6500. , Wang et al., Science. 1984 Jun. 29; 224(4656):1431-1433.) An antibody with a deletion or the like can be made, for example, by site-directed mutagenesis, random mutagenesis, biopanning using an antibody phage library, or the like. For example, KOD-Plus-Mutagenesis Kit (TOYOBO CO., LTD.) can be used for site-directed mutagenesis. An antibody with the same activity as the wild-type can be selected from mutant antibodies introduced with a deletion or the like by performing various characterizations such as FACS analysis and ELISA.

In one embodiment of the present invention, "90% or greater" may be, for example, 90, 95, 96, 97, 98, 99 or 100% or greater or within the range of any two such values. For the "homology", the percentage of the number of homologous amino acids in two or a plurality of amino acid sequences may be calculated in accordance with a known method in the art. Before calculating the percentage, amino acid sequences in a group of amino acid sequences to be compared are aligned. A space is introduced in a portion of amino acid sequences when necessary to maximize the percentage of the same amino acids. An alignment method, method of calculating the percentage, comparison method, and computer programs associated therewith have been well known in the art (e.g., BLAST, GENETYX, and the like). As used herein, "homology" can be represented by a value measured with BLAST of the NCBI, unless specifically noted otherwise. Blastp can be used in the default setting for an algorithm for comparing amino acid sequences with BLAST. Results of measurement are expressed in a numerical form as Positives or Identities.

As used herein, "polynucleotide which hybridizes under a stringent condition" refers to commonly used, well-known conditions in the art. Such a polynucleotide can be obtained by using a method such as colony hybridization, plaque hybridization, or southern blot hybridization while using a polynucleotide selected from the polynucleotides of the inventions as a probe. Specifically, the polynucleotide refers to a polynucleotide that can be identified by using a filter with immobilized DNA from a colony or plaque and performing hybridization at 65° C. in the presence of 0.7 to 1.0 M NaCl and then using an SSC (saline-sodium citrate) solution with 0.1 to 2 times concentration (composition of an SSC solution with 1 time concentration is 150 mM sodium chloride and 15 mM sodium citrate) to wash the filter under the condition of 65° C. For "stringent condition", the following are examples of conditions that can be used. (1) low ionic strength and a high temperature are used for washing (e.g., 0.015 M sodium chloride/0.0015 M sodium citrate/0.1% sodium dodecyl sulfate at 50° C.), (2) a denaturing agent such as formamide is used in hybridization (e.g., 50% (v/v) formamide, 0.1% bovine serum albumin/0.1% ficoll/0.1% polyvinyl pyrrolidone/50 mM sodium phosphate buffer with a pH of 6.5, 750 mM sodium chloride, and 75 mM sodium citrate at 42° C.), or (3) a solution comprising 20% formamide, 5×SSC, 50 mM sodium phosphate (pH 7.6), 5×Denhardt's solution, 10% dextran sulfate, and 20 mg/ml denatured sheared salmon sperm DNA, is incubated overnight at 37° C. and then a filter is washed with 1×SSC at about 37 to 50° C. The formamide concentration may be 50% or greater. Washing time may be 5, 15, 30, 60, 120 minutes, or greater. A plurality of elements are considered to affect stringency in a hybridization reaction such as temperature, salt concentration, and the like. Ausubel et al., Current Protocols in Molecular Biology, Wiley Interscience Publishers, (1995) can be referred for details. "Highly stringent condition", for example, is 0.0015 M sodium chloride, 0.0015 M sodium citrate, and 65-68° C. or 0.015 M sodium chloride, 0.0015 M sodium citrate, 50% formamide, and 42° C. Hybridization can be performed in accordance with the method described in experimental publications such as Molecular Cloning 2nd ed., Current Protocols in Molecular Biology, Supplement 1-38, DNA Cloning 1: Core Techniques, A Practical Approach, Second Edition, Oxford University Press (1995). In this regard, a sequence comprising only an A sequence or only a T sequence is preferably excluded from a sequence that hybridizes under stringent conditions. A moderately stringent condition can be readily determined by those skilled in the art based on, for example, the length of a DNA and is shown in Sambrook et al., Molecular Cloning: A Laboratory Manual, Third Ed., Vol. 1, 7.42-7.45 Cold Spring Harbor Laboratory Press, 2001, including, for a nitrocellulose filters, use of hybridization conditions of a pre-wash solution of 1.0 mM EDTA (pH 8.0), 0.5% SDS, and 5×SSC, and about 50% formamide and 2×SSC-6×SSC at about 40-50° C. (or other similar hybridization solutions such as a Stark's solution in about 50% formamide at about 42° C.) and washing conditions of 0.5×SSC, 0.1% SDS at about 60° C. Thus, the polypeptides used in the invention encompass polypeptides encoded by a nucleic acid molecule that hybridizes under highly or moderately stringent conditions to a nucleic acid molecule encoding a polypeptide described in the present invention in particular.

As used herein, a "purified" substance or biological agent (e.g., DNA vaccine, nucleic acid construct, plasmid DNA, other nucleic acid, protein or the like) refers to a substance or a biological agent from which at least a part of an agent naturally accompanying the substance or biological agent has been removed. Thus, the purity of a biological agent in a purified biological agent is generally higher than the purity in the normal state of the biological agent (i.e., concentrated). The term "purified" as used herein refers to the presence of preferably at least 75% by weight, more preferably at least 85% by weight, still more preferably at least 95% by weight, and most preferably at least 98% by weight of a biological agent of the same type. The substance or biological agent used in the present invention is preferably a "purified" substance. An "isolated" substance or biological agent (e.g., nucleic acid, protein, or the like) as used herein refers to a substance or biological agent having agents that naturally accompany the substance or biological agent substantially removed. The term "isolated" as used herein varies depending on the objective. Thus, the term does not necessarily have to be represented by purity. However, when necessary, the term refers to the presence of preferably at least 75% by weight, more preferably at least 85% by weight, still more preferably at least 95% by weight, and most preferably at least 98% by weight of a biological agent of the same type. The substance used in the present invention is preferably an "isolated" substance or biological agent.

As used herein, a "corresponding" amino acid, nucleic acid, or moiety refers to an amino acid or a nucleotide which has or is expected to have, in a certain polypeptide molecule or polynucleotide molecule (e.g., CD63, CD81, CD9 or the like), similar action as a predetermined amino acid, nucleotide or moiety in a benchmark polypeptide or a polynucleotide for comparison, and, particularly in the case of enzyme molecules, refers to an amino acid which is present at a similar position in an active site and makes a similar contribution to catalytic activity and refers to a corresponding moiety in a complex molecule (e.g., heparan sulfate or the like). For example, for an antisense molecule, it can be a similar moiety in an ortholog corresponding to a specific moiety of the antisense molecule. A corresponding amino acid can be a specific amino acid subjected for to, example, cysteination, glutathionylation, S—S bond formation, oxidation (e.g., oxidation of methionine side chain), formylation, acetylation, phosphorylation, glycosylation, myristylation or the like. Alternatively, a corresponding amino acid can be an amino acid responsible for dimerization. Such a "corresponding" amino acid or nucleic acid may be a region or a domain over a certain range. Thus, it is referred herein as a "corresponding" region or domain in such a case. Such a corresponding region or domain is useful for designing a complex molecule in the present invention.

As used herein, a "corresponding" gene (e.g., polynucleotide sequence or molecule) refers to a gene (e.g., polynucleotide sequence or molecule) of a certain species which has or is expected to have similar action as a predetermined gene in a benchmark species for comparison. When there is a plurality of genes having such action, the corresponding gene refers to a gene having the same evolutionary origin. Hence, a gene corresponding to a certain gene may be an ortholog of such a gene. Thus, a tetraspanin family protein such as CD63 corresponding to a human tetraspanin family protein such as CD63 can be found in other animals (especially mammals). Such a corresponding gene can be identified by using a technique that is well known in the art. For example, a corresponding gene in a certain animal (e.g., mouse) can be found by searching a database comprising sequences of the animal from using the sequence of SEQ ID NO: 1, 2 or the like as a query sequence, as a benchmark gene of the corresponding gene (e.g., tetraspanin family protein such as CD63 or the like).

As used herein, "fragment" refers to a polypeptide or polynucleotide with a sequence length of 1 to n–1 with respect to the full length polypeptide or polynucleotide (with length n). The length of can a fragment be appropriately changed in accordance with the objective. Examples of the lower limit of such a length include 3, 4, 5, 6, 7, 8, 9, 10, 15, 20, 25, 30, 40, 50 and more amino acids for a polypeptide. Lengths represented by an integer that is not specifically listed herein (e.g., 11 and the like) also can be suitable as a lower limit. Further, examples of the length include 5, 6, 7, 8, 9, 10, 15, 20, 25, 30, 40, 50, 75, 100, and more nucleotides for a polynucleotide. Lengths represented by an integer that is not specifically listed herein (e.g., 11 and the like) also can be suitable as a lower limit. As used herein, such a fragment is understood to be within the scope of the present invention, for example, when a full length version functions as a marker or a target molecule, as long as the fragment itself also functions as a marker or a target molecule.

According to the present invention, the term "activity" as used herein refers to a function of a molecule in the broadest sense. Activity generally encompasses, but is not intended to be limited to, biological function, biochemical function, physical function, and chemical function of a molecule. Examples of activity include enzymatic activity, ability to interact with another molecule, ability to activate, promote, stabilize, inhibit, suppress, or destabilize a function of another molecule, stability, and ability to localize at a specific position in a cell. When applicable, the term is also directed to a function of a protein complex in the broadest sense. As used herein, "biological function", with regard to a gene or a nucleic acid or polypeptide related thereto, refers to a specific function that the gene, nucleic acid, or polypeptide can have in a living body. Examples thereof include, but are not limited to, production of a specific antibody, enzymatic activity, impartation of resistance, and the like. As used herein, "biological activity" refers to activity that a certain agent (e.g., polynucleotide, protein, or the like) can have in a living body, including activity exerting a variety of functions (e.g., transcription promoting activity) such as the activity of activating or deactivating a molecule from interaction with another molecule. When two agents interact, the biological activity thereof can be thought of as the bond between the two molecules and the biological change resulting therefrom, e.g., the two molecules are bound when precipitation of one of the molecules with an antibody results in co-precipitation of the other molecule. Thus, one method of determination includes observing such co-precipitation. When an agent is for instance an enzyme, the biological activity thereof encompasses the enzymatic activity thereof. Another example includes binding of a ligand to a corresponding receptor when an agent is a ligand. Such biological activity can be measured by a well-known technique in the art. Thus, "activity" refers to various measurable indicators that indicate or reveal the bond (either directly or indirectly) or affects a response (i.e., having a measurable effect in response to some exposure or stimulation). Examples thereof include the affinity of a compound that directly binds to the polypeptide or polynucleotide of the invention, the amount of proteins upstream or downstream after some stimulation or event, and a dimension of another similar function.

As used herein, "expression" of a gene, a polynucleotide, a polypeptide, or the like refers to the gene or the like being subjected to a certain action in vivo to be converted into another form. Preferably, expression refers a gene, a polynucleotide, or the like being transcribed and translated form into a of a polypeptide. However, transcription to make an mRNA is also one embodiment of expression. Thus, "expression product" as used herein encompasses such a polypeptide and protein, and mRNA. More preferably, such a polypeptide form can be a form which has undergone post-translation processing. Preferably, this acts as an antigen, so that a polypeptide or protein form is preferably as an expression product. For example, the expression level of a tetraspanin family protein such as CD63 or the like can be determined by any method. Specifically, the expression level of a tetraspanin family protein such as CD63 or the like can be found by evaluating the amount of mRNA of tetraspanin family protein such as CD63 or the like, the amount of protein of a tetraspanin family protein such as CD63 or the like, and the biological activity of the tetraspanin family protein such as CD63 or the like. Such a measurement value can be used in companion diagnosis. The amount of protein or mRNA of a tetraspanin family protein such as CD63 or the like can be determined by the method described in detail in other parts of the specification or a method known in the art.

As used herein, "functional equivalent" refers to any entity having the same function of interest but a different structure relative to the original target entity. Thus, it is understood that a functional equivalent of "tetraspanin family protein such as CD63 or the like" or an antibody thereof encompasses mutants and variants (e.g., amino acid sequence variant or the like) of the tetraspanin family protein such as CD63 or the like or antibody thereof that are not the tetraspanin family protein such as CD63 or the like or antibody thereof itself, which have the biological action of the tetraspanin family protein such as CD63 or the like or antibody thereof or can change, upon action, into the tetraspanin family protein such as CD63 or the like or the antibody thereof itself or a mutant or variant of the tetraspanin family protein such as CD63 or the like or the antibody thereof (e.g., including nucleic acids encoding a tetraspanin family protein such as CD63 or the like or an antibody thereof itself and mutants and variants of the tetraspanin family protein such as CD63 or the like or antibody thereof, and vector, cell and the like comprising such a nucleic acid). It is understood, even without specific mention, that a functional equivalent of a tetraspanin family protein such as CD63 or the like or an antibody thereof can be used in the same manner as the tetraspanin family protein such as CD63 or the like or antibody thereof. A functional equivalent can be found by searching a database or the like.

As used herein, "search" refers to utilizing a certain nucleic acid base sequence electronically, biologically, or by another method to find another nucleic acid base sequence having specific a function and/or property. Examples of electronic search include, but are not limited to, BLAST (Altschul et al., J. Mol. Biol. 215:403-410 (1990)), FASTA (Pearson & Lipman, Proc. Natl. Acad. Sci., USA 85:2444-2448 (1988)), Smith and Waterman method (Smith and Waterman, J. Mol. Biol. 147:195-197 (1981)), Needleman and Wunsch method (Needleman and Wunsch, J. Mol. Biol. 48:443-453 (1970)) and the like. Examples of biological search include, but are not limited to, stringent hybridization, a macroarray with a genomic DNA applied to a nylon membrane or the like or a microarray with a genomic DNA applied to a glass plate (microarray assay), PCR, in situ hybridization and the like. Herein, a gene used in the present invention is intended to include corresponding genes identified by such electronic search or biological search.

As a functional equivalent of the invention, it is possible to use an amino acid sequence with one or more amino acid insertions, substitutions, or deletions, or addition to one or both ends. As used herein, "one or more amino acid insertions, substitutions, or deletions, or addition to one or both ends in an amino acid sequence" refers to an alteration with a substitution of a plurality of amino acids or the like to the extent that can occur naturally by a well-known technical method such as site-directed mutagenesis or natural mutation. An altered amino acid sequence can have, for example, 1 to 30, preferably 1 to 20, more preferably 1 to 9, still more preferably 1 to 5, and especially preferably 1 to 2 amino acid insertions, substitutions, or deletions, or additions to one or both ends. Preferably, an altered amino acid sequence may be an amino acid sequence having one or more (preferably 1 or several, or 1, 2, 3 or 4) conservative substitutions in an the amino acid sequence of a tetraspanin family protein such as CD63 or the like. "Conservative substitution" refers herein to a substitution of one or more amino acid residues with other chemically similar amino acid residue so as not to substantially alter a function of a protein. Examples thereof include substitutions of a hydrophobic residue with another hydrophobic residue, substitutions of a polar residue with another polar residue having the same charge and the like. Functionally similar amino acids that can be substituted in this manner are known in the art for each amino acid. Specific examples include alanine, valine, isoleucine, leucine, proline, tryptophan, phenylalanine, methionine and the like for nonpolar (hydrophobic) amino acids, and glycine, serine, threonine, tyrosine, glutamine, asparagine, cysteine and the like for polar (neutral) amino acids. Examples of positively charged (basic) amino acids include arginine, histidine, lysine and the like. Further, examples of a negatively-charged (acidic) amino acid include aspartic acid, glutamic acid, and the like.

As used herein, an "antibody" includes a molecule capable of specifically bind to a specific epitope on an antigen or a population thereof. An antibody may be a polyclonal antibody or a monoclonal antibody. Antibodies can have various forms such as one or more forms selected consisting of full length antibodies from the group (antibodies with a Fab region and an Fc region), Fv antibodies, Fab antibodies, F(ab')$_2$ antibodies, Fab' antibodies, diabodies, single stranded antibodies (e.g., scFv), dsFv, multispecific antibodies (e.g., bispecific antibodies), peptides or polypeptides with an antigen binding property, chimeric antibodies (e.g., (mouse-human chimeric antibodies, chicken-human chimeric antibodies, and the like), mouse antibodies, chicken antibodies, humanized antibodies, human antibodies, or an equivalent thereof. Antibodies also encompass modified and unmodified antibodies. Modified antibodies may be formed by an antibody binding to various molecules such as polyethylene glycol. A chemical modification can be applied to a modified antibody using a known approach. Such an antibody can also be covalently bound, or fused by recombination, to an enzyme such as alkaline phosphatase, horseradish peroxidase, or α galactosidase. The antibodies or the like used in the present invention can be of any origin, type, shape, or the like as long as the antibodies bind to a target thereof. Specifically, known antibodies such as a non-human animal antibody (e.g., a mouse antibody, a rat antibody, or a camel antibody), a human antibody, a chimeric antibody, or a humanized antibody can be used. In the present invention, a monoclonal or polyclonal antibody can be utilized, but a monoclonal antibody is preferable. It is preferable that an antibody binds specifically to a target. Further, antibodies encompass modified and unmodified antibodies. Modified antibodies may be formed by an antibody binding to various molecules such as polyethylene glycol. A modified antibody can be obtained by applying a chemical modification to an antibody by using a known approach.

As used herein, "subject (person)" refers to a target subjected to prophylaxis, therapy, or the like of the invention, including humans and mammals excluding humans (e.g., one or more of mice, guinea pigs, hamsters, rats, rabbits, pigs, sheep, goats, cows, horses, cats, dogs, marmosets, monkeys, chimpanzees and the like).

As used herein, "agent" is broadly used interchangeably and may be any substance or other element (e.g., light, radiation, heat, electricity, and other forms of energy) as long as the intended objective can be achieved. Examples of such a substance include, but are not limited to, proteins, polypeptides, oligopeptides, peptides, polynucleotides, oligonucleotides, nucleotides, nucleic acids (including for example DNAs such as cDNAs and genomic DNAs and RNAs such as mRNAs), polysaccharides, oligosaccharides, lipids, organic small molecules (e.g., hormones, ligands, information transmitting substances, organic small molecules, molecules synthesized by combinatorial chemistry, small molecules that can be used as medicine (e.g., small molecule ligands and the like) and a composite molecules thereof. Typical examples of an agent specific to a polynucleotide include, but are not limited to, polynucleotides having complementarity with a certain sequence homology (e.g., 70% or greater sequence identity) to a sequence of the polynucleotide, polypeptides such as transcription factors that bind to a promoter region, and the like. Typical examples of an agent specific to a polypeptide include, but are not limited to, antibodies directed specifically to the polypeptide or a derivative or analog thereof (e.g., single chain antibody), specific ligands or receptors when the polypeptide is a receptor or ligand, substrates when the polypeptide is an enzyme, and the like.

Thus, an "agent" (or detection agent or the like) that "specifically" interacts (or binds) to a biological agent such as a polynucleotide or a polypeptide as used herein encompasses agents with affinity to the biological agent such as a polynucleotide or polypeptide that is typically the same or higher, preferably significantly (e.g., statistically significantly) higher, than the affinity to other unrelated polynucleotides or polypeptides (especially those with less than 30% identity). Such affinity can be measured, for example, by a hybridization assay, binding assay or the like.

As used herein, "therapy" refers to the prevention of exacerbation, preferably maintaining of the current condition, more preferably alleviation, and still more preferably disappearance of a disease or disorder (e.g., cerebral malaria) in case of such a condition, including being capable of exerting a prophylactic effect or an effect of improving a disease of a patient or one or more symptoms accompanying the disease. Preliminary diagnosis with suitable therapy may be referred to as "companion therapy" and a diagnostic agent therefor may be referred to as "companion diagnostic agent".

As used herein, "therapeutic drug (agent)" broadly refers to all agents capable of treating a condition of interest (e.g., disease such as cancer or the like), and refers to an inhibitor (e.g., antibody) provided by the present invention. In one embodiment of the present invention, "therapeutic drug" may be a pharmaceutical composition comprising an active ingredient and one or more pharmacologically acceptable carriers. A pharmaceutical composition can be manufactured, for example, by mixing an active ingredient with the carriers by any method known in the technical field of pharmaceuticals. Further, mode of usage of a therapeutic drug is not limited, as long as it is used for therapy. A therapeutic drug may be an active ingredient alone or a mixture of an active ingredient and any ingredient. Further, the shape of the carriers is not particularly limited. For example, the carrier may be a solid or liquid (e.g., buffer).

As used herein, "prevention" or "prophylaxis" refers to taking an action against a disease or disorder (e.g., cancer) from being in such a condition prior to being in such a condition. A prophylactic effect is also expected especially when used as a vaccine. For example, it is possible to use the agent of the invention to perform diagnosis, and optionally use the agent of the invention to prevent or take measures to prevent cancer or the like.

As used herein, "prophylactic drug (agent)" broadly refers to any agent capable of preventing a condition of interest (e.g., disease such as cancer or the like).

As used herein, "immune response enhancer" refers to any agent for enhancing at least one immune related response such as immune action or immune response. This is also called an immune enhancing drug or immunopotentiator. Enhancement of immune responses includes T cell growth, enhancement of T cell responses, enhancement of activity of macrophage, and the like. The enhancement also includes reactions for enhancing immune responses that are suppressed by viruses or cancer. Adjuvants used with an antigen to enhance normal immunocompetence are also encompassed in immune response enhancers by definition.

As used herein, "enhancement of T cell response" refers to enhancement of an immune response by T cells, which encompasses antitumor immune responses. This is also referred to as T cell activation. Enhancement of T cell responses produces or grows, for example, memory T cells or effector T cells. Alternatively, such enhancement adjusts the activity of regulatory T cells. Alternatively, such enhancement can induce cytokine secretion by T cells, expand clones, or the like. At the effector stage of responses, effector $CD4^+$ T cells respond to an antigen by producing a cytokine with various actions such as B cell activation or leukocyte mobilization or activation, and $CD8^+$ cytotoxic T lymphocytes kill other cells.

As used herein, "cytotoxic agent" refers to any agent that damages cells. For example, a cytotoxic agent acts on other cells such as cancer cells upon cell division to destroy cells. Therefore, cytotoxic agents can also be used as an anticancer agent.

As used herein, "cancer" refers to any cancer that can be treated or prevented with the DNA vaccine or medicament of the invention. Examples of cancer include, but are not limited to, hepatocellular carcinoma, esophageal squamous cell carcinoma, breast cancer, pancreatic cancer, head and neck squamous cell carcinoma or adenocarcinoma, colorectal cancer, renal cancer, cerebral cancer (tumor), prostate cancer, small cell and non-small cell lung cancer, bladder cancer, bone or joint cancer, uterine cancer, cervical cancer, multiple myeloma, hematopoietic malignancy, lymphoma, Hodgkin's disease, non-Hodgkin's lymphoma, skin cancer, melanoma, squamous cell carcinoma, leukemia, lung cancer, ovarian cancer, gastric cancer, Kaposi's sarcoma, cancer, laryngeal cancer, endocrine cancer, thyroid parathyroid cancer, pituitary cancer, adrenal cancer, bile duct cell cancer, endometriosis, esophageal cancer, liver cancer, NSCLC, osteosarcoma, pancreatic cancer, SCLC, soft tissue tumor, AML, and CML.

As used herein, the terms "cytotoxic T lymphocytes", "cytotoxic T cells", and "CTL" are interchangeable, and refer to a subgroup of T lymphocytes that can recognize non-self cells (e.g., tumor/cancer cells and virally infected cells) and can induce the death of such cells, unless specifically defined otherwise.

As used herein, "kit" refers to a unit providing portions to be provided (e.g., vaccine, testing agent, diagnostic agent, therapeutic agent, antibody, label, manual, and the like), generally in two or more separate sections. This form of a kit is preferred when intending to provide a composition that should not be provided in a mixed state but is preferably mixed immediately before use for safety reasons or the like. Such a kit advantageously comprises instructions or a manual preferably describing how the provided portions (e.g., testing agent, diagnostic agent, or therapeutic agent) should be used or how reagent should be handled. When the kit is used herein as a reagent kit, the kit generally comprises an instruction describing how to use a vaccine, testing agent, diagnostic agent, therapeutic agent, antibody, and the like.

As used herein, "instruction" is a document with an explanation of the method of use of the present invention for a physician or for other users. The instruction describes a detection method of the invention, how to use a diagnostic agent, or a description instructing administration of a medicament or the like. Further, an instruction may have a description instructing oral administration, or administration to the esophagus (e.g., by injection or the like) as the site of administration. The instruction is prepared in accordance with a format specified by a regulatory authority of the country in which the invention is practiced (e.g., Ministry of Health, Labour and Welfare in Japan, Food and Drug Administration (FDA) in the U.S., or the like), with an explicit description showing approval by the regulatory authority. The instruction is a so-called package insert, and is generally provided in, but not limited to, paper media. The instructions may also be provided in a form such as electronic media (e.g., web sites provided on the Internet or emails).

Preferred Embodiments

The preferred embodiments of the present invention are explained hereinafter. It is understood that the embodiments provided hereinafter are provided to better facilitate the understanding of the present invention, so that the scope of the present invention should not be limited by the following descriptions. Thus, it is apparent that those skilled in the art can refer to the descriptions herein to make appropriate modifications within the scope of the present invention. It is also understood that the following embodiments of the invention can be used individually or as a combination.

SUMMARY

A DNA vaccine is a potent dosage form that can elicit humoral or cell-mediated immune responses to an encoded antigen. However, immunogenicity needs to be improved in order to achieve an antigen specific $CD8^+$ T cell response.
(Exosome-Antigen Nucleic Acid Construct)

In one aspect, the present invention provides a nucleic acid construct (e.g., DNA construct) comprising a nucleic acid sequence encoding an exosome marker protein and a nucleic acid sequence encoding a vaccine antigen. A DNA vaccine, which is a representative embodiment of the nucleic acid construct of the invention, has expectation as a prophylactic vaccine for an infectious disease or cancer therapeutic vaccine because of the capability to strongly induce not only humoral immunity, but also cell-mediated immune response, especially cytotoxic T cells (CTL). Meanwhile, an expected effect was not attained in the past in clinical trials in view of the weak immunogenicity of DNA vaccines and safety issues in humans. As demonstrated in the Examples, the present invention provides a nucleic acid construct comprising a nucleic acid sequence encoding an exosome marker protein and a nucleic acid sequence encoding a vaccine antigen to reduce the immunogenicity of an exosome targeting DNA vaccine to a clinically applicable level. In addition, the clinical effect of an exosome vaccine with an antigen loaded in an exosome using this vaccine is confirmed. In view of the above, such a construct is noteworthy in terms of enabling clinical application of a DNA vaccine. For example, as described in the Examples, stronger CTL induction is confirmed relative to a group without expression of an antigen in an exosome, as a result of administering an exosome targeting DNA vaccine, which is a representative embodiment of the present invention, to a mouse by intramuscular vitro transfection electroporation. In this regard, in using a plasmid DNA (e.g., pCD63-OVA) encoding an OVA antigen which is fused with CD63, CD9, CD81, or the like used in the Examples resulted in transportation of OVA by the exosome. It has been revealed that strong CTL induction is attained as a result of not just localization to a membrane, but exosome targeting from comparison after making a plasmid DNA prepared by fusing CALNEXIN), which is a membrane protein of vesicles, to an ovalbumin (OVA) antigen. The superior effect of the present invention is demonstrated in the Examples and the like. Further, the inventors subcutaneously transplanted E.G-7, which is a type of thymus of mice expressing OVA, into mice using the DNA vaccine shown in the Examples, which are representative embodiments of the invention, and the mice were subsequently inoculated with the DNA vaccine. Consequently, tumor growth is confirmed to be strongly suppressed in a group inoculated with an exosome targeting DNA vaccine compared to a control group, thus demonstrating that a significant effect is also attained as an anticancer agent.

Any protein can be used as the exosome marker protein used in the present invention, as long as the objective of the invention, such as enhancement of the function of a DNA vaccine, can be achieved. Meanwhile in one embodiment, the exosome marker protein is preferably a protein that is present in a membrane of an exosome. Although not wishing to be bound by any theory, this is because use of a protein that is present in a membrane more advantageously achieves targeting to an exosome and advantageously achieve enhancement of a function as a DNA vaccine.

In a preferred embodiment, the exosome marker protein used in the nucleic acid construct of the invention is a protein that belongs to the tetraspanin family. The tetraspanin family is known as a surface marker for exosomes. Although not wishing to be bound by any theory, this is because it is understood that tetraspanin is involved in activation of cells or cell motility by forming a complex with integrin, growth factor receptor, or the like on a cellular membrane and repairing a function, thus targeting to an exosome is more advantageously achieved and enhancement of a function as a DNA vaccine is advantageously achieved.

In a specific embodiment, exosome marker proteins that can be used in the present invention include CD63, CD81, CD9, CD31, HLA-G, TSG101, Rab5b, ALIX, and the like, which are described in a database for exosomes (e.g., ExoCarta, http_colon_forward slash-forward slash_exocarta_dot_org_forward slash_browse_results? org_name=& cont_type=protein & tissue=&gene_symbol=or the like. Proteins described therein are proteins contained in exosomes. Nearly 10000 proteins are registered. In particular, CD63, CD81, CD9, CD31, and the like are known as representative tetraspanin. Since anticancer action and immune enhancing action are shown in experiments using CD63, CD9, or CD81, it is understood that members that are similarly present on another membrane, especially other members of tetraspanin, exhibit the same anticancer action and immune enhancing action. In one particularly preferred embodiment, such a protein is, but not limited to, CD63, CD9, or CD81, and more preferably CD63.

An antigen encoded by a nucleic acid contained in the nucleic acid construct of the invention can be any antigen, as long as the objective is functioning as a vaccine. Of course, an antigen is encoded as a nucleic acid, so that an antigen is a peptide, polypeptide, or a protein.

In a specific embodiment, the antigens used in the present invention include antigens of pathogens such as viral antigens, cancer antigen peptides, viral antigen peptides, virus derived proteins, and the like. Any antigen that can be used for diseases in which protect is expected against infections by CTL can be used.

In one embodiment, the nucleic acid construct of the invention can be a plasmid DNA. There can be an effect of facilitating administration to a subject or the like by using the construct in a form of a plasmid DNA.

In one aspect, the present invention provides a DNA vaccine comprising the nucleic acid construct of plasmid DNA of the invention. The nucleic acid construct or plasmid DNA contained in the DNA vaccine of the invention can comprise a combination of one or more features of the nucleic acid construct and plasmid of any embodiment explained herein as needed.

In another aspect, the present invention provides an exosome comprising a vaccine antigen protein and an exosome marker protein in a fused form. If the nucleic acid construct of the invention is used, this is generated in a form of an exosome marker protein fused with a vaccine antigen protein. An exosome comprising such a fusion protein can in itself be used as a medicament such as a vaccine. Thus, it is understood that the present invention also provides such an exosome itself. Such an exosome is different from a naturally-occurring exosome. This is called the exosome of the invention herein in some cases.

Therefore, the present invention also provides a protein in a form of a vaccine antigen protein fused with an exosome marker protein. As used herein, "fusion" refers to a state where a protein or a polypeptide is attached to another protein or a polypeptide, and mainly a state where two or more genes are integrally transcribed/expressed to form a single protein or a polypeptide in a protein or a polypeptide made artificially (by genetic engineering). In the present invention, fusion thus refers to a state where an exosome marker protein and a vaccine antigen are integrally transcribed/expressed to form a single protein or a polypeptide, which is also called the protein of the invention.

(Medicament or the Like)

In another aspect, the present invention also provides a medicament comprising the nucleic acid construct of the invention, the DNA vaccine of the invention, the protein of the invention, or the exosome of the invention. It is understood that the nucleic acid construct, DNA vaccine, protein, or exosome used in the medicament or the like of the invention can comprise any one or more additional features of the invention discussed in detail in the section of (Exosome-antigen nucleic acid construct) or the like.

In one embodiment, the present invention also provides an immune response enhancer comprising the nucleic acid construct of the invention, the DNA vaccine of the invention, the protein of the invention, or the exosome of the invention.

In another embodiment, the present invention provides a composition for enhancing a T cell response comprising the nucleic acid construct of the invention, the DNA vaccine of the invention, the protein of the invention, or the exosome of the invention.

In another embodiment, the present invention provides a cytotoxic agent comprising the nucleic acid construct of the invention, the DNA vaccine of the invention, the protein of the invention, or the exosome of the invention.

In yet another embodiment, the present invention is a medicament for treating or preventing cancer comprising the nucleic acid construct of the invention, the DNA vaccine of the invention, the protein of the invention, or the exosome of the invention.

In another embodiment, the present invention provides a method of enhancing an immune response in a subject, comprising administering to the subject an effective amount of the nucleic acid construct of the invention, the DNA vaccine of the invention, the protein of the invention, or the exosome of the invention. It is understood that the nucleic acid construct, DNA vaccine, protein, or exosome used in the method of the invention can comprise any one or more additional features of the invention discussed in detail in the section of (Exosome-antigen nucleic acid construct) or the like.

In one embodiment, the present invention provides a method of enhancing a T cell response, comprising administering to a subject an effective amount of the nucleic acid construct of the invention, the DNA vaccine of the invention, the protein of the invention, or the exosome of the invention.

In another embodiment, the present invention provides a method of treating or preventing cancer, comprising administering to a subject an effective amount of the nucleic acid construct of the invention, the DNA vaccine of the invention, the protein of the invention, or the exosome of the invention.

In this manner, the present invention is provided as a medicament (therapeutic drug or prophylactic drug) in various forms described above.

It is preferable that a route of administration of a therapeutic drug that is effective in therapy is used. For example, the route of administration may be intravenous, subcutaneous, intramuscular, intraperitoneal, or oral administration or the like. The dosage form may be, for example, injection, capsule, tablet, granule or the like. When a component of the invention is administered, use thereof as an injection is effective. An aqueous solution for injection may be stored, for example, in a vial or a stainless steel container. Further, an aqueous solution for injection may contain, for example, saline, saccharide (e.g., trehalose), NaCl, NaOH, or the like. Further, a therapeutic drug may contain a buffer (e.g., phosphate buffer), stabilizer, or the like. A dosage form that is suitable as a DNA vaccine is preferable.

The composition, medicament, therapeutic agent, prophylactic agent, and the like of the present invention generally comprise a therapeutically effective amount of therapeutic agent or ingredient a active and pharmaceutically acceptable carrier or excipient. As used herein, "pharmaceutically acceptable" means government regulatory agency-approved or Japanese Pharmacopoeia or other commonly recognized pharmacopoeia-listed for use in animals and more specifically in humans. As used herein, "carrier" refers to a diluent, adjuvant, excipient, or vehicle administered with a therapeutic agent. Such a carrier can be an aseptic liquid such as water or oil, including liquids derived from petroleum, animal, plant or synthesis, such as but not limited to peanut oil, soybean oil, mineral oil, sesame oil, and the like. When a medicament is orally administered, water is a preferred carrier. For intravenous administration of a pharmaceutical composition, saline and aqueous dextrose are preferred carriers. Preferably, aqueous saline solution and aqueous dextrose and glycerol solution are used as a liquid carrier of an injectable solution. Suitable excipients include light anhydrous silicic acid, crystalline cellulose, mannitol, starch, glucose, lactose, sucrose, gelatin, malt, rice, wheat flour, chalk, silica gel, sodium stearate, glyceryl monostearate, talc, sodium chloride, powdered skim milk, glycerol, propylene, glycol, water, ethanol, carmellose calcium, carmellose sodium, hydroxypropyl cellulose, hydroxypropyl methylcellulose, polyvinyl acetal diethylamino acetate, polyvinylpyrrolidone, gelatin, medium-chain fatty acid triglyceride, polyoxyethylene hydrogenated castor oil 60, saccharose, carboxymethylcellulose, corn starch, inorganic salt, and the like. When desired, the composition can contain a small amount of wetting agent or emulsifier or pH buffer. These compositions can be in a form of solution, suspension, emulsion, tablet, pill, capsule, powder, sustained release mixture, or the like. It is also possible to use traditional binding agents and carriers, such as tryglyceride, to prepare a composition as a suppository. Oral preparation can also comprise a standard carrier such as medicine grade mannitol, lactose, starch, magnesium stearate, sodium saccharin, cellulose, or magnesium carbonate. Examples of a suitable carrier are described in E. W. Martin, Remington's Pharmaceutical Sciences (Mark Publishing Company, Easton, composition contains a therapeutically effective amount of therapeutic agent, preferably in a purified form, together with a suitable amount of carrier, such that the composition is provided in a form suitable for administration to a patient. A preparation must be suitable for the administration format. In addition, the composition may comprise, for example, a surfactant, excipient, coloring agent, flavoring agent, preservative, stabilizer, buffer, suspension, isotonizing agent, binding agent, disintegrant, lubricant, fluidity improving agent, corrigent, or the like.

Examples of "salt" in one embodiment of the present invention include anionic salts formed with any acidic (e.g., carboxyl) group and cationic salts formed with any basic (e.g., amino) group. Salts include inorganic salts and organic salts, as salts described in, for example, Berge et al., J. Pharm. Sci., 1977, 66, 1-19. Further examples include metal salts, ammonium salts, salts with organic base, salts with inorganic acid, salts with organic acid, and the like. "Solvate" in one embodiment of the present invention is a compound formed with a solute and solvent. For example, J. Honig et al., The Van Nostrand Chemist's Dictionary P650 (1953) can be referred for solvates. When a solvent is water, a solvate formed is a hydrate. It is preferable that the solvent does not obstruct the biological activity of the solute. Examples of such a preferred solvent include, but not particularly limited to, water and various buffers. Examples of "chemical modification" in one embodiment of the present invention include modification with PEG or a derivative thereof, fluorescein modification, biotin modification, and the like.

When the present invention is administered as a medicament, various delivery systems are known, and such systems can be used to administer a therapeutic agent of the invention to a suitable site (e.g., esophagus). Such a system, for example, can use a recombinant cell that can express encapsulated therapeutic agent (e.g., polypeptide) in microcapsules, microparticles and liposomes, use endocytosis mediated by a receptor, construct a therapeutic nucleic acid as a part of a retrovirus vector or other vector, or the like. The method of introduction includes, but not limited to, intradermal, intramuscular, intraperitoneal, intravenous, subcutaneous, intranasal, epidural, and oral routes. A medicament can be administered by any suitable route, such as by injection, bolus injection, or by absorption through epithelial or mucocutaneous lining (e.g., oral cavity, rectum, intestinal mucosa, or the like). In addition, an inhaler or mistifier using an aerosolizing agent can be used as needed. Moreover, other biological activating agents can also be administered therewith. Administration can be systemic or local. The present invention, when used in cancer, may be administered through any suitable route such as direct injection into cancer (lesion) or the like.

In a preferred embodiment, a composition can be prepared as a pharmaceutical composition adapted to administration to humans in accordance with a known method. Such a composition can be administered by an injection. A composition for injection is typically a solution in an aseptic isotonic aqueous buffer. A composition can also comprise a local anesthetic such as lidocaine, which alleviates the pain at the site of injection, and a solubilizing agent as needed. Generally, components can be supplied individually or by mixing the components together in a unit dosage form, and supplied, for example, in a sealed container such as an ampoule or sachet showing the amount of active agent, or as a lyophilized powder or water-free concentrate. When a composition is to be administered by injection, the composition can be distributed using an injection bottle containing aseptic agent-grade water or saline. When a composition is to be administered by injection, an aseptic water or saline ampoule for injection can also be provided such that the ingredients can be mixed prior to administration.

The composition, medicament, therapeutic agent, and prophylactic agent of the invention can be prepared as a neutral or salt form or other prodrugs (e.g., ester or the like). Pharmaceutically acceptable include salts formed with a free carboxyl group, derived from hydrochloric acid, phosphoric acid, acetic acid, oxalic acid, tartaric acid, or the like, salts formed with a free amine group, derived from isopropylamine, triethylamine, 2-ethylaminoethanol, histidine, procaine, or the like, and salts derived from sodium, potassium, ammonium, calcium, ferric hydroxide, or the like.

The amount of therapeutic agent of the invention that is effective in therapy of a specific disorder or condition may vary depending on the properties of the disorder or condition. However, such an amount can be determined by those skilled in the art by a standard clinical technique based on the descriptions herein. Furthermore, an in vitro can assay be used some in cases to assist the identification of the optimal dosing range. The precise dose to be used in a preparation may also vary depending on the route of administration or the severity of the disease or disorder. Thus, the dose should be determined in accordance with the judgment of the attending physician or the condition of each patient. The dosage is not particularly limited, but may be 0.001, 0.01, 0.1, 1, 5, 10, 15, 100, or 1000 mg/kg body weight per dosage or within a range between any two values described above. The dosing interval is not particularly limited, but may be, for example, 1 or 2 administration every 1, 7, 14, 21, or 28 days or 1 or 2 administrations in the range of period between any two values described above. The dosage, dosing interval, and dosing method may be appropriately selected depending on the age, weight, symptom, target organ or the like of the patient. Further, it is preferable that a therapeutic drug contains a therapeutically effective amount, or an amount effective for exerting a desired effect, of active ingredients. If a malignant tumor marker significantly decreases after administration, the presence of a therapeutic effect may be acknowledged. The effective dose can be estimated from a dose-response curve obtained from in vitro or animal model testing systems.

An agent such as the medicament of the invention or a therapeutic agent or a prophylactic agent can be provided as a kit.

In a specific embodiment, the present invention provides an agent pack or kit comprising one or more containers filled with one or more components of the composition, medicament, or the like of the invention. Optionally, information indicating approval of manufacture, use, or sale for administration to humans by a government agency regulating the manufacture, use or sale of medicaments or biological products in a stipulated form can be appended to such a container.

In a specific embodiment, the medicament or the like comprising a component of the invention can be administered via liposomes, microparticles, or microcapsules. In various embodiments of the present invention, it may be useful to use such a composition to achieve sustained release of the component of the invention.

The formulation procedure for the therapeutic drug, prophylactic drug, or the like of the invention as a medicament or the like is known in the art. The procedure is described, for example, in the Japanese Pharmacopoeia, the United States Pharmacopeia, pharmacopeia of other countries, or the like. Thus, those skilled in the art can determine the embodiment, such as the amount to be used, without undue experimentation from the descriptions herein.

(Novel Application of Exosome Marker Protein and Nucleic Acid Sequence Encoding the Same)

In another aspect, the present invention provides a novel application of an exosome marker protein and a nucleic acid sequence encoding the same.

In one aspect, the present invention provides a composition for improving immunogenicity of a vaccine DNA, comprising a nucleic acid sequence encoding an exosome marker protein. In another aspect, the present invention provides a nucleic acid (or nucleic acid molecule comprising a nucleic acid sequence) encoding an exosome marker protein for improving immunogenicity of a vaccine DNA. It is understood that the composition or nucleic acid of the invention can comprise any one or more additional features of the invention discussed in detail in the section of (Exosome-antigen nucleic acid construct) or the like.

In one embodiment, the exosome marker protein is a protein that is present in a membrane of an exosome in the composition or nucleic acid of the invention.

In another embodiment, the exosome marker protein belongs to the tetraspanin family in the composition or nucleic acid of the invention.

In yet another embodiment, the exosome marker protein is selected from the group consisting of any protein described in a database such as ExoCarta, e.g., CD63, CD81, CD9, CD31, HLA-G, TSG101, Rab5b, and ALIX in the composition or nucleic acid of the invention. More preferably, the exosome marker protein is CD63, CD9, or CD81. DNA vaccine inoculation of not only CD63, but also pCD9-OVA or pCD81-OVA resulted in a higher anti-OVA IgG2c/G1 ratio than vaccination with a control pOVA. Furthermore, the antigen specific CD8$^+$ T cell response also increased, and the level thereof was equivalent to pCD63-OVA vaccination. Thus, it is understood that tetraspanin generally exerts an immunologically excellent effect in DNA vaccines.

In yet another embodiment, an antigen contained in the vaccine DNA in the composition or nucleic acid of the invention includes antigens of pathogens such as viral antigens, viral antigen peptides, virus derived proteins, and the like.

In yet another embodiment, the vaccine DNA is a plasmid DNA in the composition or nucleic acid of the invention.

General Techniques

Molecular biological approaches, biochemical approaches, and microbiological approaches used herein are well known and conventional approaches in the art that are described in, for example, Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Bessatsu Jikken Igaku [Experimental Medicine, Supplemental Volume], Idenshi Donyu Oyobi Hatsugen Kaiseki Jikken Ho [Experimental Methods for Transgenesis & Expression Analysis], Yodosha, 1997, and the like. The relevant portions (which can be the entire document) of the above documents are incorporated herein by reference.

DNA synthesis techniques and nucleic acid chemistry for making an artificially synthesized gene are described in, for example, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, and the like, the relevant portions of which are incorporated herein by reference.

For example, the oligonucleotide of the invention can also be synthesized herein by a standard method known in the art, such as using an automated DNA synthesizer (a synthesizer commercially available from Biosearch, Applied Biosystems, or the like). For example, a phosphorothioate-oligonucleotide can also be synthesized by the method of Stein et al. (Stein et al., 1988, Nucl. Acids Res. 16:3209), and a methyl phosphonate-oligonucleotide can also be prepared using a control pore glass polymer support (Sarin et al., 1988, Proc. Natl. Acad. Sci. USA 85:7448-7451).

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on Examples. The above explanation and the following Examples are not provided to limit the present invention, but for the sole purpose of exemplification. Thus, the scope of the present invention is not limited to the embodiments and Examples specifically described herein and is limited only by the scope of claims.

EXAMPLES

The Examples are described hereinafter. When necessary, animals used in the following Examples were handled in compliance with the institutional guidelines of the National Institute of Biomedical Innovation, based on the Declaration of Helsinki for all animal experiments. For reagents, the specific products described in the Examples were used. However, the reagents can be substituted with an equivalent product from another manufacturer (Sigma-Aldrich, Wako Pure Chemical, Nacalai Tesque, R & D Systems, USCN Life Science INC, or the like).

Example 1

In this Example, the inventors tested whether a DNA vaccine encoding an antigen fused with CD63 can target an exosome, and whether immunogenicity of the vaccine can be improved by focusing on CD63, which is a tetraspanin protein expressed on various plasma membranes including exosome as an example of an exosome marker protein. The inventors constructed a plasmid expressing an OVA antigen fused with CD63 and made an antigen target exosomes. The inventors also attempted to identify the type of immune responses induced or promoted by exosome targeting of a DNA vaccine via a CD63 fusion antigen. In addition, the usefulness as an anticancer vaccine was evaluated.

(Materials and Methods)

DNA Construct

The cDNA of full-length CD63 (aa 1-238; SEQ ID NO: 3 to 4), CD9 (aa 1 to 226; SEQ ID NOs: 7 to 8), CD81 (aa 1 to 236; SEQ ID NOs: 11 to 12), and calnexin (aa 1 to 591; mouse NM_001110499 and NP_001103969. SEQ ID NOs: 13 to 14 (each from mouse)) was amplified by PCR using a C57BL/6J derived mouse lung cDNA library as a template. A CDNA fragment was investigated by sequencing and then introduced into a pCI mammalian expression vector (Promega), pCIneo-FLAG (Promega), or pEGFP-N1 (Clontech) as described above (Jounai, N., K. Kobiyama, M. Shiina, K. Ogata, K. J. Ishii, and F. Takeshita. 2011. J Immunol 186:1646-1655.) cDNA (V00383.1; CAA23682.1 SEQ ID NOs: 15 to 16) encoding full length OVA (aa 1 to 386) was amplified by PCR from pCI OVA (pOVA) (Nagata, T., T. Higashi, T. Aoshi, M. Suzuki, M. Uchijima, and Y. Koide. 2001. Vaccine 20:105-114.). OVA cDNA fragments were investigated by sequencing and then introduced into pCIneo-FLAG. They were named pOVA-FLAG. The full length OVA protein was fused at the N-terminus position with CD63, CD9, CD81, or calnexin. A glycine hexamer (6×glycine) was inserted between the OVA and the fused gene as a linker. Fused genes were investigated by sequencing and then introduced into a pCI vector, pCIneo-FLAG vector, or a pEGFP-N1 vector. They were named pCD63-FLAG (pCD63), pCD63-6×Gly-OVA-FLAG (pCD63-OVA), pCD9-6×Gly-OVA-FLAG (pCD9-OVA), pCD81-6×Gly-OVA-FLAG (pCD81-OVA), pCalnexin-6×Gly-OVA-FLAG (pCal-OVA), or pCD63-6×Gly-OVA-EGFP (pCD63-OVA-EGFP). All plasmids were transformed into Escherichia coli DH5α and purified using Qiagen Plasmid Endo-free Maxiprep kits (Qiagen) in accordance with the manufacturer's protocol.

Cells 293T cells and E.G7-OVA cells (E.G7) cells were purchased from American Type Culture Collection. FreeStyle™ 293-F cells (293F cells) were purchased from Life Technologies. 293T cells were cultured at 37° C. under 5% $CO_2$ in a DMEM supplemented with 50 µg/ml of penicillin-streptomycin and 10% FCS. 293F cells were cultured at 37° C. under 8% $CO_2$ in a FreeStyle™ 293 Expression medium (Life Technologies) (free of animal serum derived exosomes). E.G7 cells were cultured at 37° C. under 5% $CO_2$ in RPMI-1640 (Life Technologies) supplemented with 10% FCS, 50 µg/ml of penicillin-streptomycin, 0.05 mM of 2-mercaptoethanol, 1 mM of sodium pyruvate, 10 mM of HEPES, and 1×nonessential amino acid.

Exosome Isolation from Cell Culture Medium

Serum (exosome) free 293F cells were transfected for 48 to 72 hours with various DNA constructs. The supernatant of the medium was then collected and centrifuged for 30 minutes at 2000×g. Total Exosome Isolation kit (Life Technologies) was used according to the manufacturer's protocol to isolate exosomes from the culture medium. In short, 1.5 ml of Total Exosome Isolation reagent was added to 3 ml of cell culture medium, and the medium was incubated overnight at 4° C. and then centrifuged for 1 hour at 10,000×g at 4° C. Exosome pellets were resuspended in 100 µl of PBS. The properties of the collected exosomes were qualitatively and quantitatively evaluated as described below by electron microscopy, Western blotting, and flow cytometry.

Cell Transfection and Western Blotting

Cells were transfected as described previously (Jounai, N., K. Kobiyama, M. Shiina, K. Ogata, K. J. Ishii, and F. Takeshita. 2011. J Immunol 186:1646-1655.) A transient transfection was performed with Lipofectamine 2000 (Life Technologies) according to the manufacturer's protocol. 293F cells (1×10⁶/ml) were transfected with their respective expression plasmids. The transfected cells were collected after 48 hours from transfection. The culture medium comprising the transfected cells were centrifuged for 30 minutes at 2000×g. The cells were dissolved in a RIPA buffer and incubated for 15 hours on ice. The supernatant and the isolated exosome samples were diluted with 3×SDS buffer (125 mM of Tris-HCl: pH 6.8, 4% SDS, 20% glycerol, and 0.01% bromophenol blue) and boiled for 5 minutes at 95° C. Immunoblotting analysis was performed as described above using an anti-CD63 Ab (R5G2, MEDICAL & BIOLOGICAL LABORATORIES CO., LTD), anti-calnexin Ab (ab22595, Abcam), or anti-FLAG M2-peroxidase (HRP) Ab (A8592, Sigma) (Jounai, N., K. Kobiyama, M. Shiina, K. Ogata, K. J. Ishii, and F. Takeshita. 2011. J Immunol 186:1646-1655.)

Immunogold Electron Microscopy

An immunogold electron microscope assay was conducted as described previously (Thery, C., S. Amigorena, G. Raposo, and A. Clayton. 2006. Current protocols in cell biology/editorial board, Juan S. Bonifacino . . . [et al.] Chapter 3: Unit 3.22.). The isolated exosomes were immunolabeled using mouse anti-FLAG Ab (Sigma) as the primary Ab and gold-labeled anti-mouse IgG (10 nm Gold) (Abcam) as the secondary Ab.

Flow Cytometry Analysis 293F cells (1×10⁶/ml) were transfected with pCD63-OVA-EGFP. The culture medium comprising the transfected cells was collected after 48 hours from transfection and centrifuged. The properties of the resulting supernatant were evaluated with INFLUX (BD Bioscience) (18). 100 nm beads and 200 nm beads (Polysciences, Inc.) were used to determine the suitable gating for the exosome fraction (FIG. 5).

Animal and Immunization 6 week old female C57BL/6J mice were purchased from CLEA Japan, Inc. The mice were immunized (50 µl/muscle) by intramuscular electroporation (imEPT) using a plasmid DNA (50 µg) encoding a control or fusion protein (OVA, CD63, CD63-OVA, CD9-OVA, CD81-OVA, or Cal-OVA) in nuclease free saline.

For exosome immunization, the mice were immunized twice at the tail base on day 7 after the first immunization with 600 µg of exosome protein (OVA 40 ng) or OVA protein (40 ng) (Hyglos Gmbh) (total volume: 100 µl/mouse) in PBS. The purified exosomes used for immunizing the mice were isolated from cells that were transfected with pOVA-, pCD63-OVA, or pCal-OVA. The concentrations of the purified exosome protein and cell culture supernatant were tested using RC DC Protein Assay (BIO-RAD) according to the manufacturer's protocol. After 1 week from the last vaccination, the mice were slaughtered to measure antigen specific immune responses of the mice.

All animal experiments were conducted in accordance with the institutional guidelines for the animal facility of the National Institutes of Biomedical Innovation, Health and Nutrition.

Evaluation of Cell-Mediated Immune Response

In order to evaluate the cell-mediated immune responses, splenocytes ($2 \times 10^6$/well) were prepared and incubated in a RPMI-1640 complete medium containing 20 µg/ml of OVA peptide ($OVA_{257-264}$, $H-2K^b$ restricted OVA class I epitope, or $OVA_{323-339}$, I-A (d)-restricted OVA class II epitope) or OVA antigen (Calbiochem). Cell-mediated immune responses were measured as described previously (Onishi, M., et al., 2015. J Immunol 194:2673-2682.)

ELISA 293T cells ($1 \times 10^6$/ml) were transfected with each expression plasmid. The cells were incubated for 48 hours after transfection, and the concentration of OVA expression in cell culture supernatant and cells was measured with ELISA (Institute of Tokyo Environmental Allergy) according to the manufacturer's protocol. The OVA specific serum Ab titer was measured as described previously (Onishi, M., et al., 2015. J Immunol 194:2673-2682.)

Tetramer Assay

A tetramer assay was conducted as described previously (Kobiyama, K., et al., 2014. Proc Natl Acad Sci USA 111:3086-3091.) In short, splenocytes were stained at room temperature for 20 minutes using a PE labeled $H-2K^b$ OVA tetramer (SIINFEKL) (MEDICAL & BIOLOGICAL LABORATORIES CO., LTD.). Next, the cells were stained with FITC labeled anti-CD8α (KT15, BioLegend), PC labeled anti-TCRβ chain (H57-597, BioLegend), Brilliant Violet 421™ labeled anti-CD62L (MEL-14, BioLegend), and APC/Cy7 labeled anti-CD44 (IM7, BioLegend) Ab in PBS. The OVA tetramer$^+$CD44$^+$CD8a$^+$TCRb$^+$ cell count was determined by flow cytometry.

In Vivo CTL Assay in vivo CTL assay was conducted as described previously (Kobiyama, K., et al., 2014. Proc Natl Acad Sci USA 111:3086-3091.) In short, 6 week old C57BL/6J mice were vaccinated with a DNA vaccine. On day 21, naïve C57BL/6J mouse derived splenocytes were labeled for 10 minutes at 37° C. with 2 or 0.2 µM of CFSE. The CFSE labeled cells were incubated for 90 minutes at 37° C. with $OVA_{257-264}$ (10 µg/ml) to subject to peptide pulsing. The cells were then washed and the same number from each treatment group was delivered to immunized mice through an intravascular route. Splenocytes were isolated after 24 hours from the delivery to analyze CFSE labeled cells by flow cytometry.

Tumor Challenge

The hair on the back of mice was shaved. $1 \times 10^6$ E.G7 cells in 100 µl of PBS were subcutaneously injected into the mice. When the average tumor volume reached 1 cm$^3$, the mice were subjected to primary immunization with pOVA, pCD63-OVA, pCal-OVA, or pCIneo-FLAG (as a negative control). In the tumor prevention experiment, mice were immunized with such plasmid DNA vaccines, and E.G7 cells were injected at $1 \times 10^6$ cells in 100 µl of PBS after 10 days. The tumor volume was measured at regular intervals using a digital caliper to calculate the length×width×height.

Statistical Analysis

The statistical significant of the difference among the groups was determined using Mann-Whitney U test.

(Results)

CD63 Fusion Antigens Captured in Exosomes Act as a Vaccine

It has been previously reported that antigen containing exosome vaccine inoculation induces Th1 responses and CTL activation (Wolfers, J., et al., 2001. Nat Med 7:297-303. , Qazi, K. R., et al., 2009. Blood 113:2673-2683). To find out whether expression of CD63 fused with an antigen in a cell induces highly efficient antigen secretion by simple expression of only antigens, the inventors constructed a plasmid DNA (pCD63-OVA) encoding a fusion protein of CD63 and OVA. The inventors have decided to target OVA antigens to exosomes via CD63 because CD63 is expressed on the exosome membrane and is already used as a common exosome marker (Pols, M. S., and J. Klumperman. 2009. Experimental cell research 315:1584-1592.) In addition, the inventors prepared aa control plasmid DNA (pCal-OVA) encoding a calnexin-OVA fusion protein as a control. pCal-OVA targets an encoded antigen to the membrane of endoplasmic reticulum (Baietti, M. F., Z. et al., 2012. Nat Cell Biol 14:677-685. ; Gross, J. C., V. Chaudhary, K. Bartscherer, and M. Boutros. 2012. Nat Cell Biol 14:1036-1045. ; Lasser, C., V. S. Alikhani, K. Ekstrom, M. Eldh, P. T. Paredes, A. Bossios, M. Sjostrand, S. Gabrielsson, J. Lotvall, and H. Valadi. 2011. J Transl Med 9:9.)

Serum (exogenous exosome) free 293-F cells were transfected with each of the aforementioned plasmid DNAs. The exosomes in the serum were collected and purified from a cell culture medium using an exosome isolation reagent. The inventors then used a Western blot assay to analyze the expression of a fusion protein encoded in the cell lysate, serum, and exosome fraction (FIGS. 1A and 1B). Exosome fractions in all groups contained CD81, which is another exosome marker, but not serum. Furthermore, only the cell fraction contained calnexin. In addition, the purity of each fraction was studied (FIG. 1A). Under these conditions, OVA proteins were also detected in the serum after pOVA transfection (FIGS. 1A and 1B). In contrast, neither CD63 nor CD63-OVA fusion protein were detected in the serum, but they were both detected from the cell lysate and exosome fractions (FIGS. 1A and 1B). An endoplasmic reticulum (ER) targeting calnexin-OVA fusion protein was detected in a cell lysate, but not in the exosome fraction (FIGS. 1A and 1B). The inventors then investigated whether a CD63-OVA protein is localized on/in an exosome. The inventors used a plasmid encoding an EGFP- or FLAG-fusion protein to analyze the CD63 expression by flow cytometry and electron microscopy. Results of both analyses suggest that CD63-OVA fusion proteins in fact target exosomes (FIGS. 1C and 5).

Figure 1E:
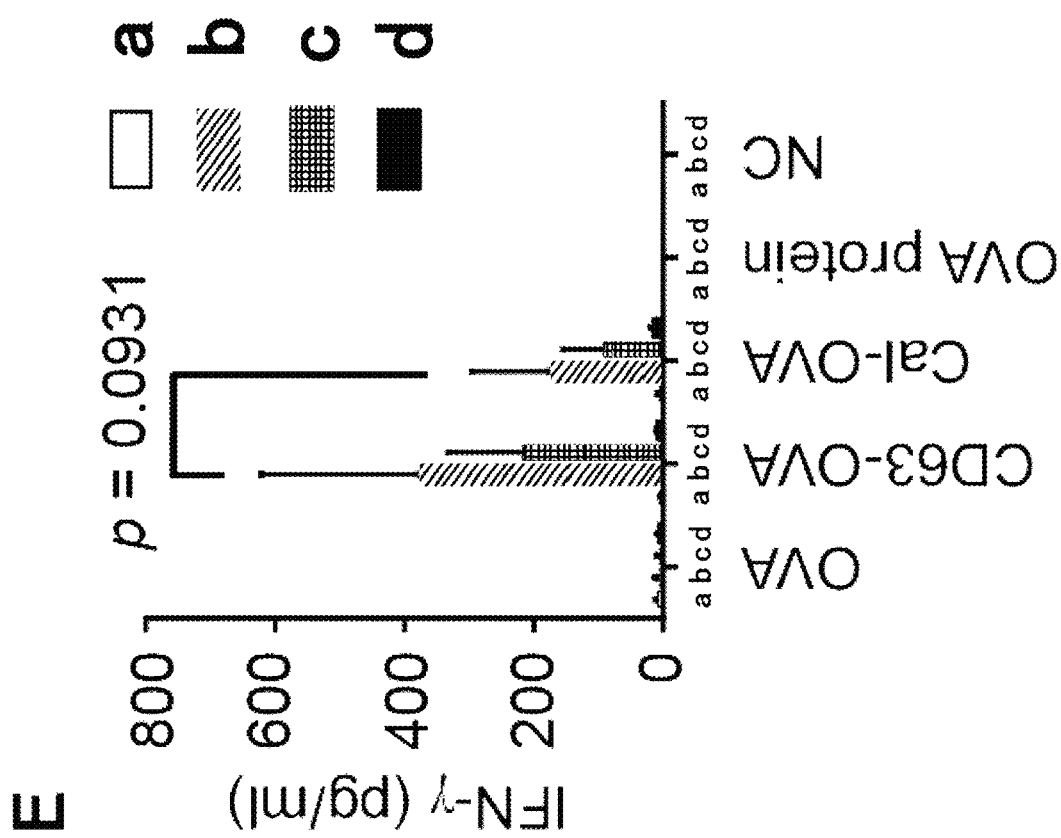
FIG. 1E Evaluation of antigen expressing exosomes as a CTL inducing immunogen. C57BL/6J mice (n=6) were immunized by introducing an OVA protein or purified exosome isolated from pOVA transfected cells, pCD63-OVA transfected cells, or pCal-OVA transfected cells through a transdermal route. On day 14 after immunization on day 0 and day 7, the serum and the spleen were used to measure the IFN-γ level induced in splenocytes by OVA, $OVA_{257-264}$, $OVA_{323-339}$, or a medium. Data represents two independent experiments. The error bar represents the SD. As for the labels of the bars, a indicates the medium, b indicates $OVA_{257-264}$, C indicates $OVA_{323-339}$, and d indicates OVA. As for the horizontal axis labels, OVA, CD63-OVA, and Cal-OVA indicate the use of a purified exosome isolated from, from the left, pOVA transfected cells, pCD63-OVA transfected cells, and pCal-OVA transfected cells, respectively. OVA protein indicates the use of an OVA protein, and NC indicates a negative control.

The inventors then investigated whether a purified exosome derived from serum free cell culture supernatant of cells that were transiently transfected with a CD63-OVA protein acts as a vaccine that induces sufficient OVA specific immune responses. The inventors transfected cells with pOVA, pCD63-OVA, or pCalnexin-OVA and then collected exosomes from the cell culture supernatant, and subcutaneously immunized C57/BL6 naïve mice at the tail base with the purified exosomes. After one week from the primary immunization, both antigen specific humoral and cellular immune responses were evaluated. CD63-OVA containing exosome immunization induced a higher antigen specific antibody than any response other tested immunization (FIG. 1D). More interestingly, immunization with CD63-OVA containing exosomes induced antigen specific IFN-γ acidic CD8$^+$ T cells, but such induction was not observed for other tested immunization (FIGS. 1E and 1F). These results strongly suggest that exosome fraction derived CD63-OVA induce a more potent CD8$^+$ T cell response than exosome fraction derived OVA alone or calnexin-OVA.

The same experiment as FIG. 1F was repeated. In other words, C57BL/6J mice (n=5) were immunized by introducing an OVA protein or a purified exosome isolated from pCD63 transfected cells, pOVA transfected cells, pCD63-OVA transfected cells, or pCalnexin-OVA transfected cells through a transdermal route. FIG. 1G shows the results of measuring the ratio of CD8$^+$ T cells recognized by an OVA$_{257-264}$ specific tetramer using a spleen on day 35 after immunization on day 0, day 14, and day 28. FIG. 1G show the same result as FIG. 1F.

Targeting of Antigen to Exosome Improves Immunogenicity of DNA Vaccine

Figure 2C:
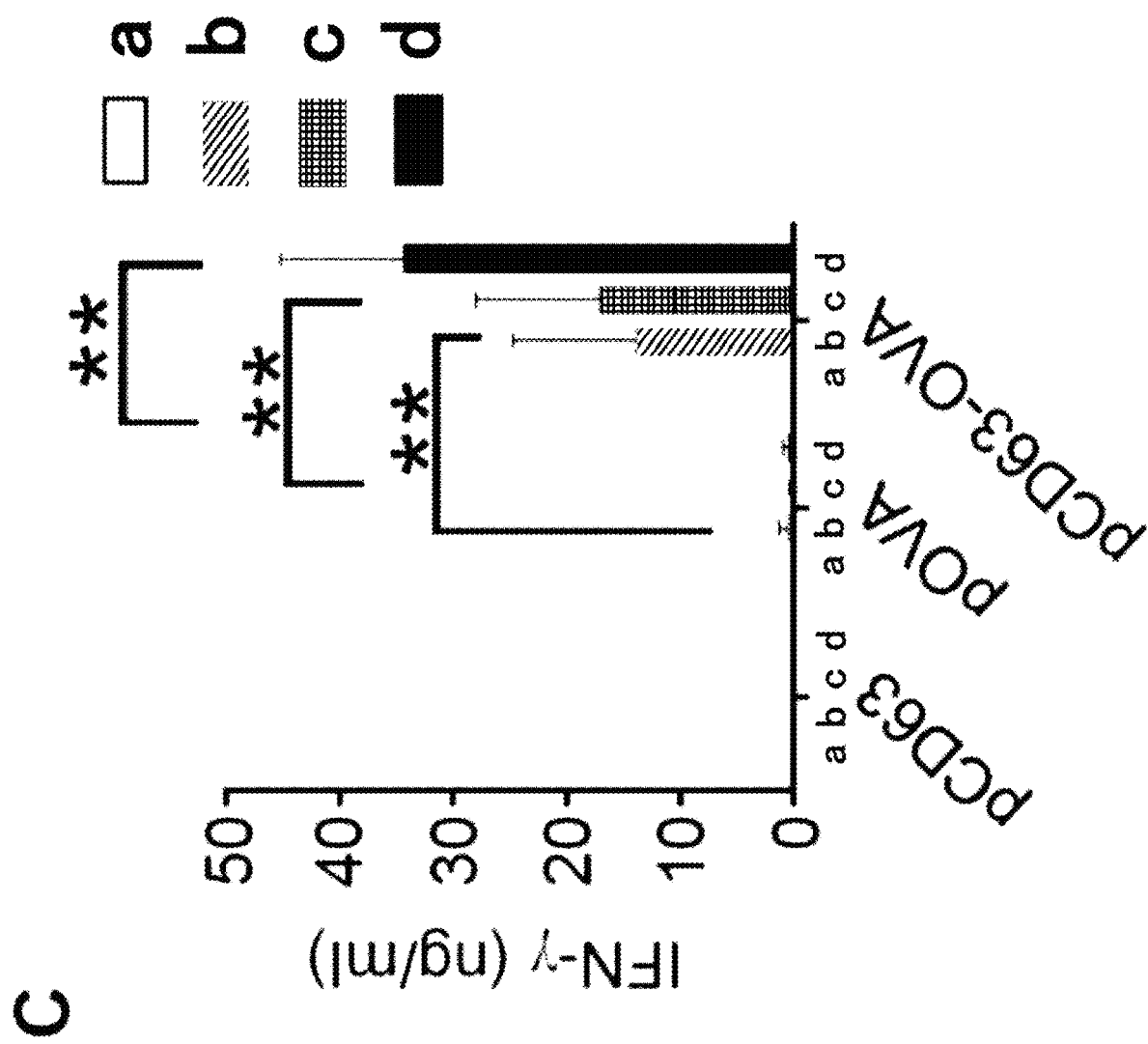
FIG. 2C The effect of antigen targeting to an exosome on immunogenicity of a DNA vaccine. C57BL/6J mice (n=6) were immunized by introducing pOVA, pCD63, or pCD63-OVA by intramuscular electroporation (50 μg/mouse). On day 21 after immunization with these plasmids on day 0 and day 14, the ratio of $CD8^+$ T cells recognized by an $OVA_{257-264}$ specific tetramer (B), and IFN-γ level induced in splenocytes by OVA, $OVA_{257-264}$, $OVA_{323-339}$, or a medium were monitored. Data represents two independent experiments. The error bar represents the SD. * indicates p<0.05 and ** indicates p<0.005 (Mann-Whitney U test). For the bar labels, a, b, c, and d indicate medium, $OVA_{257-264}$, $OVA_{323-339}$, and OVA, respectively.

Based on the above results, the inventors hypothesized that a DNA vaccine with an antigen targeting an exosome incorporated therein would have increased immunogenicity. To investigate whether a DNA vaccine with pCD63-OVA has increased immunogenicity compared to other control DNA vaccines, the inventors immunized mice twice with a plasmid DNA using imEPT to induce efficient transfection in vivo. After 1 week from booster immunization, pCD63-OVA immunized mice had significantly lower serum anti-OVA IgG1 titer than pOVA immunized mice, but there was no difference in anti-OVA total IgG and IgG2c between the two groups (FIG. 2A). If the anti-OVA IgG2c/G1 ratios of the pCD63-OVA and pOVA are compared, a higher value of anti-OVA IgG2c/G1 was observed in pCD63-OVA immunized mice relative to pOVA (FIG. 2A). The inventors then studied the frequency of OVA$_{257-264}$ specific tetramer$^+$CD44$^+$CD8$^+$ T cells in these immunized mice. A high of OVA$_{257-264}$ specific tetramer$^+$CD44$^+$CD8$^+$ T cells was observed in pCD63-OVA immunized mice relative to pOVA immunized mice (FIG. 2B). The inventors also stimulated splenocytes with either class I (OVA$_{257-264}$) or class II (OVA$_{323-333}$) OVA peptide ex vivo and then measured cytokine production from the splenocytes by ELISA. A significantly higher level of IFN-γ production was detected for each peptide stimulation with pCD63-OVA vaccination relative to pOVA (FIG. 2C).

In addition to CD63-based fusion proteins, the inventors also prepared plasmid DNA encoding a CD9-OVA (pCD9-OVA) or CD81-OVA (pCD81-OVA) fusion protein. These plasmid DNAs also target the encoded antigen to exosomes (Thery, C., L. Zitvogel, and S. Amigorena. 2002. Nat Rev Immunol 2:569-579) (Fujita, Y., N. Kosaka, J. Araya, K. Kuwano, and T. Ochiya. 2015. Trends in molecular medicine.) The inventors confirmed that both CD9-OVA proteins and CD81-OVA proteins are expressed in exosomes (FIGS. 6A and 6B). DNA vaccine inoculation with pCD9-OVA or pCD81-OVA resulted in a higher anti-OVA IgG2c/G1 ratio than vaccination with control pOVA. Furthermore, antigen specific CD8$^+$ T cell responses also increased, and the level thereof was equivalent to that of pCD63-OVA vaccination (FIGS. 6C to 6E).

The results indicate that antigen targeting to exosomes in DNA vaccine inoculation improves immunogenicity of a DNA vaccine, especially the CD8$^+$ T cell responses.

Figure 2D:
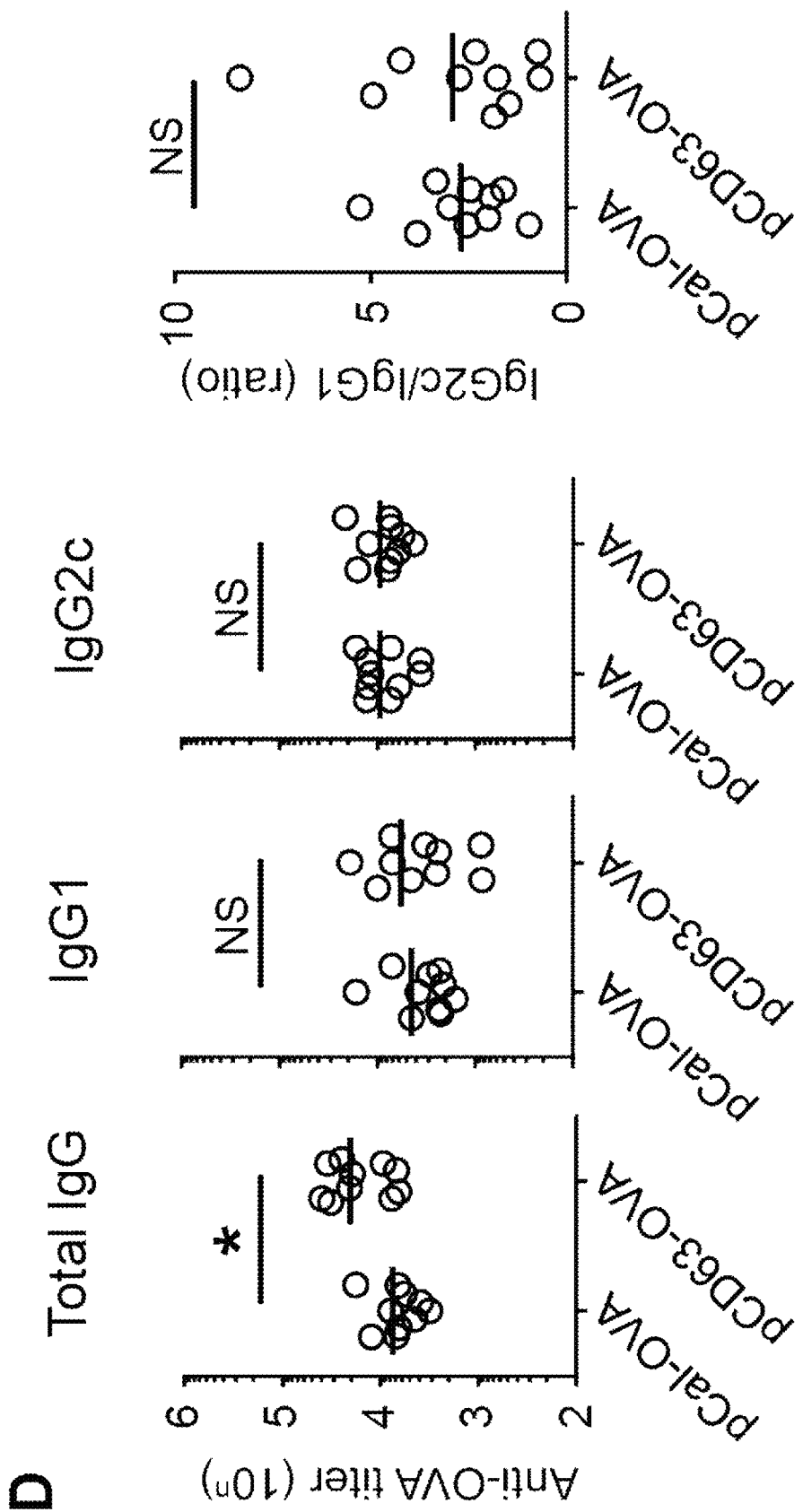
FIG. 2D The effect of antigen targeting to an exosome on immunogenicity of a DNA vaccine. C57BL/6J mice (n=10)

Exosome Targeting of Antigen is Important for Improving Immunogenicity of a DNA Vaccine Next, the inventors investigated whether the strategy to target the encoded antigen to exosomes is advantageous over an alternative strategy to promote T cell activation by DNA vaccine inoculation (e.g., targeting of an antigen to another plasma membrane such as endoplasmic reticulum). For this objective, the inventors compared the scale and type of immunogenicity of two plasmid DNAs encoding different fusion proteins: pCD63-OVA targeting exosomes and pCal-OVA targeting ER. Mice subjected to two DNA vaccine inoculations through imEPT by pCD63-OVA or pCal-OVA exhibited similar anti-OVA Ab titer and anti-OVA IgG2c/G1 ratio (FIG. 2D). However, mice that have been vaccinated with pCal-OVA exhibited higher frequency of OVA$_{257-264}$ specific tetramer$^+$CD44$^+$CD8$^+$ T cells than mice that have been vaccinated with pCD63-OVA (FIG. 2E). In addition, pCD63-OVA vaccinated mouse derived splenocytes produced a significantly higher amount of IFN-γ upon stimulation relative to pCal-OVA immunized mouse derived splenocytes (FIG. 2F). The results indicate that targeting of an antigen to the exosome membrane, not other membranes, is sufficient to improve the immunogenicity of a DNA vaccine.

CD63 Does Not Act as a Genetic Adjuvant for Co-Administered DNA Vaccine

Since pCD63-OVA vaccines induce a potent CD8$^+$ T cell response (FIG. 2), the inventors investigated whether a plasmid DNA expressing CD63 acts as a genetic adjuvant for a DNA vaccine expressing OVA. In order to evaluate the potential adjuvant effect of CD63, mice were immunized with pOVA, pCD63, mixture of pOVA and pCD63, or pCD63-OVA. After 1 week from secondary immunization, OVA specific CD4$^+$ and CD8$^+$ T cell responses were not promoted in mice subjected to pCD63 together with pOVA relative to mice subjected to pOVA alone. However, mice that were vaccinated with pCD63-OVA exhibited a significant increase in OVA specific CD4$^+$ and CD8$^+$ T cell responses (FIGS. 3A and 3B). These results indicate that CD63 itself does not function as a genetic adjuvant unless conjugated to an OVA antigen as a fusion protein. Therefore, delivery of an antigen into or on an exosome can improve the immunogenicity of a DNA vaccine.

Targeting of an Antigen to an Exosome is Useful in a Tumor Vaccine

Lastly, the inventors investigated whether a pCD63-OVA vaccine is applicable to a cancer vaccine and/or immunotherapy. Since a CTL response is important for the efficacy of a cancer vaccine, an in vivo CTL cytotoxicity assay was conducted to evaluate the level of functional CD8$^+$ T cell activity. Immunization of mice with pCD63-OVA significantly increased the OVA specific CD8$^+$ T cell mediated functional cytotoxicity relative to that induced by immunization with pOVA alone (FIG. 4A). In order to investigate whether pCD63-OVA can suppress tumor growth, explant syngeneic tumor models having E.G-7 cells, which are OVA overexpressing mouse lymphoma cells, were used. Mice were immunized with pCD63-OVA or another control plasmid DNA vaccine before seeding E.G-7 tumor cells. After seeding of tumor, tumor growth was suppressed significantly more in pCD63-OVA immunized mice compared to the control plasmid DNA immunized mice (FIG. 4B).

In order to further evaluate the potential ability of pCD63-OVA to act as a therapeutic vaccine, mice were immunized with a DNA vaccine after 10 days from tumor seeding in the same E.G-7 tumor model. Mice immunized with pCD63-OVA exhibited significantly lower tumor growth than mice in other DNA vaccine inoculation groups (FIG. 4C). There was no statistically significant difference between pOVA and pCD63-OVA vaccination from the viewpoint of tumor suppression (p=0.0749), but a better tendency of controlled tumor growth can be clearly observed with pCD63-OVA vaccination relative to pOVA vaccination. The OVA specific CD8$^+$ T cell count increased by pCD63-OVA vaccination (FIG. 4D). These results indicate that targeting of an antigen an to exosome during DNA immunization can be a novel strategy for eliciting an antigen specific CD8$^+$ T cell response. In addition, this strategy can also be applicable for use in cancer vaccines.

(Discussion)

Both humoral and cell-mediated immune responses were induced by DNA vaccine inoculation in animal models. However, an immunological response to a DNA vaccine is often weaker than expected in humans. The study of the inventors demonstrated the efficacy of pCD63-OVA DNA vaccine inoculation and suggested that immunogenicity of a DNA vaccine can be improved by targeting an antigen to an exosome. The results in this Example suggest that: 1) pCD63-OVA vaccination successfully targets the encoded OVA antigen to a secreted exosome; 2) pCD63-OVA vaccination induces a potent type I immune response such as an antigen specific and functionally cytotoxic CD8$^+$ T cell response in vivo; and 3) pCD63-OVA vaccination suppresses explant syngeneic E.G-7 cell derived tumor growth in both prophylactic and therapeutic manner.

After DNA vaccine inoculation, stroma cells and DC at the injection site were directly transfected with a plasmid DNA (Herrada, A. A., et al., 2012. Hum Vaccin Immunother 8:1682-1693.). The transfected cells then transcribed and translated the encoded antigen. The antigen was subsequently presented to T cells directly by DC or indirectly through stroma cells. This results in not only induction of CD4$^+$ Th1 cells specific to the encoded antigen, but also induction of CD8$^+$ T cells through an indirect mechanism of cross-presentation (Liu, M. A. 2003. 253:402-410.) At the same time, a plasmid DNA is detected by an intracellular DNA sensor and acts as an exogenous adjuvant for DNA vaccine induced humoral and cell-mediated immune responses to an encoded antigen (Thery, C., et al., 2002. Nat Immunol 3:1156-1162. , Zitvogel, L., et al., 1998. Nat Med 4:594-600.) Both the cellular immunological mechanism of DNA vaccine inoculation and immunological function of exosomes have been extensively studied in recent years (Gentili, M., et al. 2015. Science (New York, N.Y.) 349: 1232-1236.), while the role of exosomes in DNA vaccine induced immune responses have not been sufficiently studied. There are several previous reports of investigating the role of exosomes in immune response induction (Qazi, K. R., et al., 2009. Blood 113:2673-2683. , Cheng, Y., and J. S. Schorey. 2013. Eur J Immunol 43:3279-3290), but the data of the inventors clearly demonstrated for the first time that a plasmid DNA encoding an antigen protein fused with CD63 increases the immunogenicity of a vaccine.

The most noteworthy feature of a plasmid DNA encoding a CD63-OVA fusion protein antigen is the ability to induce a potent CD8$^+$ T cell response. The increased CD8$^+$ T cell response to the encoded antigen can be attributed to exosome targeting of the encoded antigen via CD63. However, further research is required to confirm whether cross presentation of an antigen to a CD8$^+$ T cell via an exosome is present and whether this is important for a DNA vaccine induced CD8$^+$ T cell response. It is also conceivable that CD63 and other tested tetraspanins do not exclusively target exosomes, but similarly direct the encoded antigen to other plasma membranes. More evidence is required to elucidate the detailed mechanism of cross presentation that is required for a DNA vaccine to induce a CD8$^+$ T cell response.

E.G-7 tumor cells that express OVA proteins as a tumor antigen were used in the tumor model of the inventors. Previous reports suggested that growth of tumor cells expressing OVA is reduced by immunization with an OVA protein and an adjuvant or a DNA vaccine comprised of an OVA expressing plasmid DNA (Chamoto, K., et al., 2006. Cancer Res 66:1809-1817. , Teramoto, K., et al., 2003. Cancer Res 63:7920-7925.) Other reports have already shown that exosomes can mediate CD4$^+$ and CD8$^+$ T cell dependent antitumor effects (Wolfers, J., et al., 2001. Nat Med 7:297-303.) Meanwhile, the results of the inventors confirm these findings and demonstrate, for the first time as far as the inventors are aware, that growth of E.G-7 tumor cells can be further suppressed by DNA vaccine inoculation with pCD63-OVA targeting an encoded antigen to an exosome.

The OVA-specific tetramer$^+$CD8$^+$ T cell count in tumor transplanted mice significantly increased with DNA vaccine inoculation with pCD63-OVA (FIG. 4D). This indicates that it can be possible to overcome the resistance or depletion of tumor antigen specific CD8$^+$ T cells by vaccination with a DNA encoding a fusion protein of a tumor antigen and an exosome targeting molecule such as CD63, CD9, or CD81. However, it should be noted that these tetraspanin exosome marker proteins are also expressed in other plasma membranes. Therefore, potential contribution of other plasma membranes to the increased immunogenicity cannot be excluded. Since the low endosome specificity can also lead to an off-target effect from a fusion protein with tetraspanin, there are concerns about safety in clinical application.

DNA vaccines are approved and used in veterinary applications (Redding, L., and D. B. Weiner. 2009. Expert review of vaccines 8:1251-1276.). In humans, DNA vaccines for many infectious diseases or cancer therapy are currently in clinical trials (Escudier, B., et al., 2005. J Transl Med 3:10. ; Morse, M. A., et al., 2005. J Transl Med 3:9. ; Viaud, S., et al., 2009. DPLoS One 4: e4942. ; Viaud, S., et al., 2010. Cancer Res 70:1281-1285. 38-41). These vaccines and vaccine candidates utilize various strategies for improving the low immunogenicity of DNA vaccines. The results of the inventors suggest that strategies for targeting an encoded antigen to an exosome through fusion of an antigen and an exosome marker (e.g., CD63) can be another feasible method for improving the immunogenicity of a DNA vaccine. This strategy is suitable especially for increasing the CD8$^+$ T cell response to an encoded antigen. The finding of the inventors provides insight into how the immunogenicity and efficacy of DNA vaccines can be improved. The findings of the inventors also improves the biological and immunological understanding of how an antigen encoded in DNA in a DNA vaccine is delivered/processed by the immune system to provide an antigen specific immune response.

CONCLUSION

In view of the above, the nucleic acid construct of the invention was shown to be able to improve immunogenicity of a vaccine DNA, enhance immune responses, enhance T cell responses, and achieve an effect of treating or preventing cancer and the like.

Example 2: Formulation Example

A formulation can be manufactured by the following manufacturing methods.

(Ex. 1) A suitable volume of saline can be directly added to a suitable amount of lyophilized vaccine DNA to prepare an injectable solution formulation.

(Ex. 2) A suitable volume of isotonizing solution/5% glucose solution can be added to a suitable amount of lyophilized vaccine DNA to prepare an injectable solution formulation.

(Ex. 3) A suitable volume of electrolyte corrective solution/Otsuka sodium chloride injection 10% and the like are added to a suitable amount of vaccine DNA dissolved in water to prepare an injectable solution formulation adjusted to a 0.9% NaCl concentration.

(Ex. 4) A suitable amount of vaccine DNA dissolved in water can be lyophilized to prepare a lyophilized formulation of vaccine DNA sodium salt.

Ex. 1, 3, and 4 are preferred. Ex. 2 can also be used depending on the administration method.

REFERENCE DOCUMENTS

The following are documents referenced in the Examples. The list of the following document does not constitute acquiescence that they are prior art to the present invention.
1. Donnelly, J. J., B. Wahren, and M. A. Liu. 2005. J Immunol 175:633-639.
2. Gurunathan, S., D. M. Klinman, and R. A. Seder. 2000. Annual review of immunology 18:927-974.
3. Kutzler, M. A., and D. B. Weiner. 2008. Nat Rev Genet 9:776-788.
4. Ulmer, J. B., R. R. Deck, C. M. DeWitt, A. Friedman, J. J. Donnelly, and M. A. Liu. 1994. Vaccine 12:1541-1544.
5. Tang, D. C., M. DeVit, and S. A. Johnston. 1992. Nature 356:152-154.
6. Reed, S. G., M. T. Orr, and C. B. Fox. 2013. Nat Med 19:1597-1608.
7. Thery, C., L. Zitvogel, and S. Amigorena. 2002. Nat Rev Immunol 2:569-579.
8. Simons, M., and G. Raposo. 2009. Curr Opin Cell Biol 21:575-581.
9. Milane, L., A. Singh, G. Mattheolabakis, M. Suresh, and M. M. Amiji. 2015. official journal of the Controlled Release Society.
10. Poutsiaka, D. D., D. D. Taylor, E. M. Levy, and P. H. Black. 1985. J Immunol 134:145-150.
11. Robbins, P. D., and A. E. Morelli. 2014. Nat Rev Immunol 14:195-208.
12. Bobrie, A., M. Colombo, G. Raposo, and C. Thery. 2011. Traffic 12:1659-1668.
13. Montecalvo, A., A. T. Larregina, W. J. Shufesky, D. B. Stolz, M. L. Sullivan, J. M. Karlsson, C. J. Baty, G. A. Gibson, G. Erdos, Z. Wang, J. Milosevic, O. A. Tkacheva, S. J. Divito, R. Jordan, J. Lyons-Weiler, S. C. Watkins, and A. E. Morelli. 2012. Blood 119:756-766.
14. Raposo, G., H. W. Nijman, W. Stoorvogel, R. Liejendekker, C. V. Harding, C. J. Melief, and H. J. Geuze. 1996. J Exp Med 183:1161-1172.
15. Jounai, N., K. Kobiyama, M. Shiina, K. Ogata, K. J. Ishii, and F. Takeshita. 2011. J Immunol 186:1646-1655.
16. Nagata, T., T. Higashi, T. Aoshi, M. Suzuki, M. Uchijima, and Y. Koide. 2001. Vaccine 20:105-114.
17. Thery, C., S. Amigorena, G. Raposo, and A. Clayton. 2006. Current protocols in cell biology/editorial board, Juan S. Bonifacino . . . [et al.] Chapter 3: Unit 3.22.
18. van der Vlist, E. J., E. N. Nolte-'t Hoen, W. Stoorvogel, G. J. Arkesteijn, and M. H. Wauben. 2012. Nature protocols 7:1311-1326.
19. Takeshita, F., T. Tanaka, T. Matsuda, M. Tozuka, K. Kobiyama, S. Saha, K. Matsui, K. J. Ishii, J Virol 80:6218-6224.
20. Onishi, M., K. Ozasa, K. Kobiyama, K. Ohata, M. Kitano, K. Taniguchi, T. Homma, M. Kobayashi, A. Sato, Y. Katakai, Y. Yasutomi, E. Wijaya, Y. Igarashi, N. Nakatsu, W. Ise, T. Inoue, H. Yamada, A. Vandenbon, D. M. Standley, T. Kurosaki, C. Coban, T. Aoshi, E. Kuroda, and K. J. Ishii. 2015. J Immunol 194:2673-2682.
21. Kobiyama, K., T. Aoshi, H. Narita, E. Kuroda, M. Hayashi, K. Tetsutani, S. Koyama, S. Mochizuki, K. Sakurai, Y. Katakai, Y. Yasutomi, S. Saijo, Y. Iwakura, S. Akira, C. Coban, and K. J. Ishii. 2014. Proc Natl Acad Sci USA 111:3086-3091.
22. Wolfers, J., A. Lozier, G. Raposo, A. Regnault, C. Thery, C. Masurier, C. Flament, S. Pouzieux, F. Faure, T. Tursz, E. Angevin, S. Amigorena, and L. Zitvogel. 2001. Nat Med 7:297-303.
23. Qazi, K. R., U. Gehrmann, E. Domange Jordo, M. C. Karlsson, and S. Gabrielsson. 2009. Blood 113:2673-2683.
24. Pols, M. S., and J. Klumperman. 2009. Experimental cell research 315:1584-1592.
25. Baietti, M. F., Z. Zhang, E. Mortier, A. Melchior, G. Degeest, A. Geeraerts, Y. Ivarsson, F. Depoortere, C. Coomans, E. Vermeiren, P. Zimmermann, and G. David. 2012. Nat Cell Biol 14:677-685.
26. Gross, J. C., V. Chaudhary, K. Bartscherer, and M. Boutros. 2012. Nat Cell Biol 14:1036-1045.
27. Lasser, C., V. S. Alikhani, K. Ekstrom, M. Eldh, P. T. Paredes, A. Bossios, M. Sjostrand, S. Gabrielsson, J. Lotvall, and H. Valadi. 2011. J Transl Med 9:9.
28. Fujita, Y., N. Kosaka, J. Araya, K. Kuwano, and T. Ochiya. 2015. Trends in molecular medicine.
29. Herrada, A. A., N. Rojas-Colonelli, P. Gonzalez-Figueroa, J. Roco, C. Oyarce, M. A. Ligtenberg, and A. Lladser. 2012. Hum Vaccin Immunother 8:1682-1693.
30. Liu, M. A. 2003. Journal of internal medicine 253:402-410.
31. Thery, C., L. Duban, E. Segura, P. Veron, O. Lantz, and S. Amigorena. 2002. Nat Immunol 3:1156-1162.
32. Zitvogel, L., A. Regnault, A. Lozier, J. Wolfers, C. Flament, D. Tenza, P. Ricciardi-Castagnoli, G. Raposo, and S. Amigorena. 1998. Nat Med 4:594-600.
33. Gentili, M., J. Kowal, M. Tkach, T. Satoh, X. Lahaye, C. Conrad, M. Boyron, B. Lombard, S. Durand, G. Kroemer, D. Loew, M. Dalod, C. Thery, and N. Manel. 2015. Science (New York, N.Y.) 349:1232-1236.
34. Cheng, Y., and J. S. Schorey. 2013. Mycobacterium tuberculosis infection. Eur J Immunol 43:3279-3290.
35. Chamoto, K., D. Wakita, Y. Narita, Y. Zhang, D. Noguchi, H. Ohnishi, T. Iguchi, T. Sakai, H. Ikeda, and T. Nishimura. 2006. Cancer Res 66:1809-1817.
36. Teramoto, K., K. Kontani, Y. Ozaki, S. Sawai, N. Tezuka, T. Nagata, S. Fujino, Y. Itoh, O. Taguchi, Y. Koide, T. Asai, I. Ohkubo, and K. Ogasawara. 2003. Cancer Res 63:7920-7925.
37. Redding, L., and D. B. Weiner. 2009. Expert review of vaccines 8:1251-1276.
38. Escudier, B., T. Dorval, N. Chaput, F. Andre, M. P. Caby, S. Novault, C. Flament, C. Leboulaire, C. Borg, S. Amigorena, C. Boccaccio, C. Bonnerot, O. Dhellin, M. Movassagh, S. Piperno, C. Robert, V. Serra, N. Valente, J. B. Le Pecq, A. Spatz, O. Lantz, T. Tursz, E. Angevin, and L. Zitvogel. 2005. J Transl Med 3:10.
39. Morse, M. A., J. Garst, T. Osada, S. Khan, A. Hobeika, T. M. Clay, N. Valente, R. Shreeniwas, M. A. Sutton, A. Delcayre, D. H. Hsu, J. B. Le Pecq, and H. K. Lyerly. 2005. J Transl Med 3:9.
40. Viaud, S., M. Terme, C. Flament, J. Taieb, F. Andre, S. Novault, B. Escudier, C. Robert, S. Caillat-Zucman, T. Tursz, L. Zitvogel, and N. Chaput. 2009. PLOS One 4: e4942.
41. Viaud, S., C. Thery, S. Ploix, T. Tursz, V. Lapierre, O. Lantz, L. Zitvogel, and N. Chaput. 2010. Cancer Res 70:1281-1285.

(Note)

As disclosed above, the present invention is exemplified by the use of its preferred embodiments. However, it is understood that the scope of the present invention should be interpreted solely based on the Claims. It is also understood d that any patent, any patent application, and any references cited herein should be incorporated herein by reference in the same manner as the contents are specifically described herein.

INDUSTRIAL APPLICABILITY

The present invention can be utilized in any industry that is associated with DNA vaccines, such as the vaccine industry and pharmaceutical industry.

SEQUENCE LISTING FREE TEXT

SEQ ID NO: 1: nucleic acid sequence of human CD63, NM_001040034

SEQ ID NO: 2: amino acid sequence of human CD63, NP_001244318

SEQ ID NO: 3: nucleic acid sequence of mouse CD63, NM_001042580

SEQ ID NO: 4: amino acid sequence of mouse CD63, NP_001036045

SEQ ID NO: 5: nucleic acid sequence of human CD9, NM_001769

SEQ ID NO: 6: amino acid sequence of human CD9, NP_001760

SEQ ID NO: 7: nucleic acid sequence of mouse CD9, NM_007657

SEQ ID NO: 8: amino acid sequence of mouse CD9, NP_031683

SEQ ID NO: 9: nucleic acid sequence of human CD81, NM_001297649

SEQ ID NO: 10: amino acid sequence of human CD81, NP_001284578

SEQ ID NO: 11: nucleic acid sequence of mouse CD81, NM_133655

SEQ ID NO: 12: amino acid sequence of mouse CD81, NP_598416

SEQ ID NO: 13: nucleic acid sequence of calnexin used in the Examples (mouse)

SEQ ID NO: 14: amino acid sequence of calnexin used in the Examples (mouse)

SEQ ID NO: 15: nucleic acid sequence of OVA used in the Examples, V00383.1

SEQ ID NO: 16: amino acid sequence of OVA used in the Examples, CAA23682.1

The invention claimed is:

1. A nucleic acid construct comprising a nucleic acid sequence encoding an exosome marker protein and a nucleic acid sequence encoding a vaccine antigen, wherein the exosome marker protein and the vaccine antigen are expressed in a fused form.

2. The nucleic acid construct of claim 1, wherein the exosome marker protein is a protein that is present in a membrane of an exosome.

3. The nucleic acid construct of claim 1, wherein the exosome marker protein belongs to the tetraspanin family.

4. The nucleic acid construct of claim 1, wherein the exosome marker protein is selected from the group consisting of CD63, CD81, CD9, CD31, HLA-G, TSG101, Rab5b, and ALIX.

5. The nucleic acid construct of claim 1, wherein the exosome marker protein is selected from the group consisting of CD63, CD81, and CD9.

6. The nucleic acid construct of claim 1, wherein the antigen is of a pathogen.

7. The nucleic acid construct of claim 1, wherein the nucleic acid construct is a plasmid DNA.

8. The nucleic acid construct of claim 1, wherein the expressed protein is present in an exosome.

9. A protein in a form of a vaccine antigen protein fused with an exosome marker protein.

10. The protein of claim 9, wherein the exosome marker protein is a protein that is present in a membrane of an exosome.

11. The protein of claim 9, wherein the exosome marker protein belongs to the tetraspanin family.

12. The protein of claim 9, wherein the exosome marker protein is selected from the group consisting of CD63, CD81, CD9, CD31, HLA-G, TSG101, Rab5b, and ALIX.

13. The protein of claim 9, wherein the exosome marker protein is selected from the group consisting of CD63, CD81, and CD9.

14. The protein of claim 9, wherein the antigen is of a pathogen.

15. An exosome comprising a vaccine antigen protein and an exosome marker protein in a fused form.

16. The exosome of claim 15, wherein the exosome marker protein is a protein that is present in a membrane of an exosome.

17. The exosome of claim 15, wherein the exosome marker protein belongs to the tetraspanin family.

18. The exosome of claim 15, wherein the exosome marker protein is selected from the group consisting of CD63, CD81, CD9, CD31, HLA-G, TSG101, Rab5b, and ALIX.

19. The exosome of claim 15, wherein the exosome marker protein is selected from the group consisting of CD63, CD81, and CD9.

20. The exosome of claim 15, wherein the antigen is of a pathogen.

* * * * *